(12) United States Patent
Frey et al.

(10) Patent No.: US 9,861,096 B2
(45) Date of Patent: Jan. 9, 2018

(54) BIODEGRADABLE CHEMICAL DELIVERY SYSTEM

(75) Inventors: Margaret W. Frey, Ithaca, NY (US); Chunhui Xiang, Beijing (CN); Michael P. Hoffmann, Ithaca, NY (US); Alan G. Taylor, Geneva, NY (US); Jeffrey Gardner, Hector, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/122,072

(22) PCT Filed: Sep. 30, 2009

(86) PCT No.: PCT/US2009/059076
§ 371 (c)(1),
(2), (4) Date: Jul. 25, 2011

(87) PCT Pub. No.: WO2010/039865
PCT Pub. Date: Apr. 8, 2010

(65) Prior Publication Data
US 2011/0275520 A1  Nov. 10, 2011

Related U.S. Application Data

(60) Provisional application No. 61/166,995, filed on Apr. 6, 2009, provisional application No. 61/101,915, filed on Oct. 1, 2008.

(51) Int. Cl.
| | |
|---|---|
| *A01N 25/10* | (2006.01) |
| *A01N 25/34* | (2006.01) |
| *C05G 3/00* | (2006.01) |
| *C08J 3/21* | (2006.01) |
| *C08L 1/02* | (2006.01) |
| *C08L 3/02* | (2006.01) |
| *C08L 67/02* | (2006.01) |
| *C08L 67/04* | (2006.01) |
| *C08L 89/00* | (2006.01) |
| *C08L 97/00* | (2006.01) |
| *C08L 101/16* | (2006.01) |
| *D01F 6/62* | (2006.01) |
| *C08L 89/04* | (2006.01) |
| *D01F 1/10* | (2006.01) |
| *D01F 6/82* | (2006.01) |
| *D01F 6/88* | (2006.01) |

(52) U.S. Cl.
CPC ............ *A01N 25/10* (2013.01); *A01N 25/34* (2013.01); *C05G 3/0029* (2013.01); *C08J 3/21* (2013.01); *C08L 1/02* (2013.01); *C08L 3/02* (2013.01); *C08L 67/02* (2013.01); *C08L 67/04* (2013.01); *C08L 89/00* (2013.01); *C08L 89/04* (2013.01); *C08L 97/005* (2013.01); *C08L 101/16* (2013.01); *D01F 1/10* (2013.01); *D01F 6/625* (2013.01); *D01F 6/82* (2013.01); *D01F 6/88* (2013.01); *C08L 2205/16* (2013.01); *C08L 2205/18* (2013.01)

(58) Field of Classification Search
CPC .......... C08L 67/04; C08L 101/16; C08L 1/02; C08L 2205/16; C08L 3/02; A01N 25/34; A01N 25/10; A01G 9/1086; C05G 3/0029
See application file for complete search history.

(56) References Cited

U.S. PATENT DOCUMENTS

| | | | | |
|---|---|---|---|---|
| 5,470,944 | A | * | 11/1995 | Bonsignore ............... A61L 2/26 424/423 |
| 5,578,325 | A | * | 11/1996 | Domb et al. ................... 424/501 |
| 5,603,744 | A | * | 2/1997 | K urner .................. C05B 17/00 71/13 |
| 2006/0263417 | A1 | * | 11/2006 | Lelkes et al. .................. 424/443 |
| 2008/0131395 | A1 | * | 6/2008 | Wellinghoff et al. ........ 424/76.3 |
| 2009/0326128 | A1 | * | 12/2009 | Macossay-Torres ... B82Y 30/00 524/413 |

FOREIGN PATENT DOCUMENTS

| | | |
|---|---|---|
| KR | 10-0362798 | 1/2005 |
| KR | 10-0515064 A | 9/2005 |
| KR | 10-0572711 | 4/2006 |

OTHER PUBLICATIONS

Ke et al. (Starch, Poly(lactic acid) and Poly(vinyl alcohol) Blends, Jan. 2003, Journal of Polymers and the Environment, vol. 11, pp. 7-14).*
Masaki et al (Cutinase-Like Enzyme from the Yeast *Cryptococcus* sp. Strain S-2 Hydrolyzes Polylactic Acid and Other Biodegradable Plastics, Nov. 2005, Applied and Environmental Microbiology, vol. 71, pp. 7548-7550).*
Guohua et al (Water Resistance, mechanical properties and biodegradability of methylated-cornstarch/poly(vinyl alcohol) blend film, Apr. 2006, Polymer Degradation and Stability, vol. 91, pp. 703-711).*

(Continued)

*Primary Examiner* — Mark V Stevens
(74) *Attorney, Agent, or Firm* — Clark & Elbing LLP

(57) ABSTRACT

Polymeric materials are provided that are produced from a blend of hydrophilic and hydrophobic biodegradable polymers. The polymeric materials can form fibers, nonwoven fabrics, films, coatings, etc. A compound can be incorporated in the polymeric materials. The delivery of the compound can be controlled by diffusion of the compound from the polymeric material and during biodegradation of the polymeric material. The release rate is controlled by varying the composition of the polymeric material to control diffusion rates of the compound and/or biodegradation rate of the polymeric material. This technology provides methods for delivering and controlling release rates of pesticides and related compounds in agricultural and non-agricultural settings. When adhered to plants or plant parts, the polymeric materials can provide protection from insect and disease pests. In pellet or capsule form, pesticides can be delivered into seed furrows along with crop seeds, providing similar protection.

27 Claims, 18 Drawing Sheets

(56) References Cited

OTHER PUBLICATIONS

Khalikova et al (Microbial Dextran-Hydrolyzing Enzymes: Fundamentals and Applications, Jun. 2005, Microbiology and Molecular Biology Reviews, vol. 69, pp. 306-325).*
Clapier et al (Annual Reviews of Biochemistry, 2009, vol. 78, pp. 273-304).*
Cornell University (Agronomy Fact Sheet Series, Magnesium for Field Crops, 2011, fact sheet 59, pp. 1-2).*
Zhou et al (InTech, 2012, Chapter 6).*
Kenawy et al (Journal of Controlled Release, 2002, vol. 81, pp. 57-64).*
Kim et al (Polymer, 2006, vol. 47, pp. 5097-5107).*
Anastassopoulou et al (Critical Reviews in Oncology/Hematology, 2002, vol. 42, pp. 79-91).*
Thunwall, et al (Journal of Applied Polymer Science, First published Sep. 2007, vol. 107, pp. 918-929).*
NatureWorks (Technology Focus Report: Polylactic acid containing fillers and fibers, Feb. 19, 2007).*
Notification Concerning Transmittal of International Preliminary Report on Patentability and International Preliminary Report on Patentability (Chapter I of the PCT) for International Application No. PCT/US09/59076 dated Apr. 14, 2011 (7 pages).
International Searching Authority, Patent Cooperation Treaty Office, Notification of Transmittal of the International Search Report and the Written Opinion of the International Searching Authority along with International Search Report and Written Opinion of corresponding PCT Patent Application No. PCT/US2009/059076, dated Apr. 29, 2010 (12 pgs.).
Cook et al., "Polypeptides for controlled release applications: Synthesis and preliminary characterization and release studies," Int J Pharma. 159:197-206 (1997).
Deitzel et al., "The effect of processing variables on the morphology of electrospun nanofibers and textiles," Polymer 42:261-272 (2001).
Franson et al., "Influence of copolymer composition on non-fickian water transport through glassy copolymers," J App Poly Sci. 28:1299-1310 (1983).
Funabashi et al., "Biodegradable composites of poly(lactic acid) with cellulose fibers polymerized by aluminum triflate," Macromol Symp. 224:309-321 (2005).
Huang et al., "Degradation of porous poly($_{D,L}$-lactic-co-glycolic acid) films based on water diffusion," J Biomed Mater Res A. 80A:909-915 (2007).
Kenawy et al., "Release of tetracycline hydrochloride from electrospun poly(ethylene-co-vinylacetate), poly(lactic acid), and a blend," J Control Release. 81:57-64 (2002).
Kim et al., "Control of degradation rate and hydrophilicity in electrospun non-woven poly(D,L-lactide) nanofiber scaffolds for biomedical applications," Biomaterials. 24:4977-4985 (2003).
Marcovich et al., "Cellulose micro/nanocrystals reinforced polyurethane," J Mater Res. 21:870-881 (2006).
Markland et al., "Modified polypeptides containing [gamma]-benzyl glutamic acid as drug delivery platforms," Int J Pharma. 178:183-192 (1999).
Orts et al., "Enhanced ordering of liquid crystalline suspensions of cellulose microfibrils: A small angle neutron scattering study," Macromolecules. 31:5717-5725 (1998).
Tuovinen et al., "Drug release from starch-acetate films," J Control Release. 91:345-354 (2003).
Xiang et al., "Nanocomposite fibers electrospun from poly(lactic acid)/cellulose nanocrystals," J Biobased Materials and Bioenerg. 3:1-9 (2009).
Xiang et al., "Selective chemical absorbance in electrospun non-wovens," J App Poly Sci. 106:2363-2370 (2007).
Zeng et al., "Influence of the drug compatibility with polymer solution on the release kinetics of electrospun fiber formulation," J Control Release. 105:43-51 (2005).
Zeng et al., "Biodegradable electrospun fibers for drug delivery," J Control Release. 92:227-231 (2003).

* cited by examiner (a)

(b)

BIODEGRADABLE CHEMICAL DELIVERY SYSTEM

CROSS-REFERENCE TO RELATED APPLICATIONS

This application is a national stage application under 35 U.S.C. §371 of PCT Application No. PCT/US2009/059076, filed Sep. 30, 2009, which claims priority to and the benefit of U.S. provisional patent application Ser. No. 61/101,915, entitled Controlled Release Agricultural Chemical Delivery System, filed Oct. 1, 2008 and Ser. No. 61/166,995, entitled Controlled Release Agricultural Chemical Delivery System, filed Apr. 6, 2009, each of which is incorporated herein by reference in its entirety.

STATEMENT REGARDING FEDERALLY SPONSORED RESEARCH OR DEVELOPMENT

The disclosed invention was made with government support under USDA—HATCH project no. 3110006036 NYC-329415 from the Cornell University Agricultural Experiment Station federal formula funds, Cooperative State Research, Education, and Extension Service, U.S. Department of Agriculture. The government has rights in this invention.

TECHNICAL FIELD

The present invention relates to biodegradable polymeric materials and methods for making them. The invention also relates to polymeric materials for controlled release of substances of interest and methods for making them.

BACKGROUND OF THE INVENTION

Polylactic Acid (PLA) as a Biodegradable Polymer

Advanced technology in petrochemical based polymers has brought many benefits to mankind (Ray, S. S., Yamada, K., Okamoto, M., Ueda, K., Control of biodegradability of polylactide via nanocomposite technology. Macromolecular Materials and Engineering, 2003. 288(3): p. 203-208). However, it has become evident that the ecosystem is disturbed as a result of the use of non-degradable plastic materials for disposable items. The environmental impact of persistent plastic wastes is a growing global concern, and alternative disposal methods are limited. Since the petroleum resources are finite there is an urgent need to develop renewable source based environmentally benign polymeric materials, especially in short-term packaging and disposable applications, which do not involve the use of toxic or noxious components in their manufacture, and can be composted to biodegradable products.

Polylactic acid (PLA) is a highly versatile, biodegradable, aliphatic polyester that can be derived from 100% renewable resources, such as corn and sugar beets. Cargill Dow LLC has developed a patented, low-cost continuous process for the production of lactic acid-based polymers (Drumright, R. E., P. R. Gruber, and D. E. Henton, Polylactic acid technology. Advanced Materials, 2000. 12(23): p. 1841-1846). This low-cost biodegradable PLA increases the range of controlled-release options for agricultural utility.

PLA is well-known as a biodegradable polymer in nature or compost. However, PLA is not easily biodegraded by microorganisms or enzymes in soil or water in nature, unless the period exceeds two years. This degradation rate is not sufficiently fast for applications where degradation times of a few months are desired (Funabashi, M. and M. Kunioka, Biodegradable composites of poly(lactic acid) with cellulose fibers polymerized by aluminum triflate. Macromolecular Symposia, 2005. 224: p. 309-321).

The environmental degradation of PLA occurs by a two-step process. During the initial phase of degradation, the high molecular weight polyester chains hydrolyze to lower molecular weight oligomers. This reaction can be accelerated by acids or bases and is affected by both temperature and moisture levels. Embrittlement of the plastic occurs during this step at a point where the molecular number (Mn) decreases to less than about 40000. At about this same Mn, microorganisms in the environment continue the degradation process by converting these lower molecular weight components to carbon dioxide, water, and humus. The structural integrity of molded PLA particles decreases as the molecular weight drops and eventually the particle disintegrates. A microstructure or morphology related to the hydrophilicity of PLA is very important for controlling the hydrodegradation rate. Funabashi et al. (Masahiro Funabashi, M. K., Biodegradable Composites of Poly(lactic acid) with Cellulose Fibers Polymerized by Aluminum Triflate. Macromolecular Symposia, 2005. 224(1): p. 309-321) reported that the biodegradability of PLA composites was accelerated by the existence of paper fibers or cotton fibers.

PLA is of increasing commercial interest since it can be made from completely renewable agricultural products, has comparable properties to many petroleum-based plastics and is readily biodegradable (Drumright, R. E., P. R. Gruber, and D. E. Henton, Polylactic acid technology. Advanced Materials, 2000. 12(23): p. 1841-1846; Tsuji, H. and Y. Ikada, Blends of aliphatic polyesters.2. Hydrolysis of solution-cast blends from poly(L-lactide) and poly(epsilon-caprolactone) in phosphate-buffered solution. Journal of Applied Polymer Science, 1998. 67(3): p. 405-415). High molecular weight PLA is generally produced by the ring opening polymerization of lactide monomer, which in turn is obtained from the fermentation of sugar feed stocks, corn, etc. (Lunt, J., Large-scale production, properties and commercial applications of polylactic acid polymers. Polymer Degradation and Stability, 1998. 59(1-3): p. 145-1524). Even when burned PLA produces no nitrogen oxide gases, only one-third of the combustible heat generated by polyolefins, and does not damage the incinerator thus, providing a significant energy savings (Ray, S. S., Yamada, K., Okamoto, M., Ueda, K., Control of biodegradability of polylactide via nanocomposite technology. Macromolecular Materials and Engineering, 2003. 288(3): p. 203-208).

PLA has been widely used in various biomedical applications due to its biodegradability, biocompatibility, good mechanical properties and solubility in common solvents for processing (Kim, K., Yu, M., Zong, X. H., Chiu, J., Fang, D. F., Seo, Y. S., Hsiao, B. S., Chu, B., Hadjiargyrou, M., Control of degradation rate and hydrophilicity in electrospun non-woven poly(D,L-lactide) nanofiber scaffolds for biomedical applications. Biomaterials, 2003. 24(27): p. 4977-4985). However, PLA has a slow biodegradation rate even in the non-crystalline form of poly(D,L-lactide) as well as in enantiomeric semicrystalline forms of poly(D-lactide) and poly(L-lactide). Thus degradation of PLA-based materials may take too long for many biomedical applications.

The degradation of aliphatic polyester is based on a hydrolytic reaction (Kim, K., Yu, M., Zong, X. H., Chiu, J., Fang, D. F., Seo, Y. S., Hsiao, B. S., Chu, B., Hadjiargyrou, M., Control of degradation rate and hydrophilicity in electrospun non-woven poly(D,L-lactide) nanofiber scaffolds for biomedical applications. Biomaterials, 2003. 24(27): p.

4977-4985). When water molecules attack ester bonds in the polymer chains, the average length of the degraded chains decreases. Eventually, the process results in short fragments of chains with carboxyl end groups that become soluble in water. Very often, the molecular weights of some fragments are still relatively large so that the corresponding diffusion rates are slow. As a result, the remaining oligomers will lower the local pH value, catalyze the hydrolysis of other ester bonds and speed up the degradation process. This mechanism is termed autocatalysis, and is frequently observed in thick biodegradable implants. However, if the dimension of the implant is small and the diffusion path is short, the hydrophilic oligomers can quickly escape from the surface. This is the case with electrospun scaffolds, in which the dimension of the nanofibers is small and the diffusion length for the degraded byproducts (hydrophilic oligomers) is short. As a result, the possibility of autocatalysis in electrospun scaffolds is very limited (Kim, K., Yu, M., Zong, X. H., Chiu, J., Fang, D. F., Seo, Y. S., Hsiao, B. S., Chu, B., Hadjiargyrou, M., Control of degradation rate and hydrophilicity in electrospun non-woven poly(D,L-lactide) nanofiber scaffolds for biomedical applications. Biomaterials, 2003. 24(27): p. 4977-4985).

The degradation of PLA is primarily due to hydrolysis of the ester linkages, which occurs more or less randomly along the backbone of the polymer. Hydrolysis requires the presence of water according to the following reaction: (David E. Henton, P. G., Jim Lunt, and Jed Randall, Polylactic Acid Technology, in Natural Fibers, Biopolymers, and Biocomposites, M. M. Amar K. Mohanty, and Lawrence T. Drzal, Editor. 2005, CRC Press. p. 528-569).

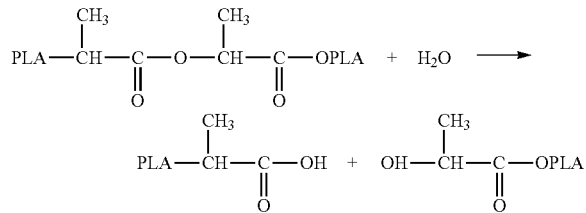

The rate of hydrolysis is determined by its intrinsic rate constant, water concentration, acid or base catalysis, temperature, and morphology (David E. Henton, P. G., Jim Lunt, and Jed Randall, Polylactic Acid Technology, in Natural Fibers, Biopolymers, and Biocomposites, M. M. Amar K. Mohanty, and Lawrence T. Drzal, Editor. 2005, CRC Press. p. 528-569). Two major challenges to the stabilization of PLA with regard to hydrolysis are the fact that it is quite permeable in water and that the hydrolysis reaction is autocatalytic. The autocatalytic hydrolysis reaction is as follows:

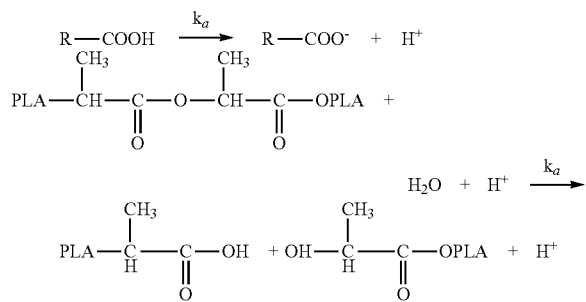

The following equation describes the decrease in ester concentration [E] over time:

$$\frac{d[E]}{dt} = k[-COOH][H_2O] = \frac{d(1/Mn)}{dt} \quad (1)$$

For a random chain scission, $[-COOH] \propto 1/M_n$ and the product $[H_2O][E]$ is constant. Rearranging to $$M_n d(1/M_n) = k dt \quad (2)$$

the integrated form becomes $$Ln\ M_{n,t} = Ln\ M_{n,0} - kt \quad (3)$$

where $M_{n,t}$=number average molecular weight at time t, $M_{n,0}$=number average molecular weight at time zero, and k is the hydrolysis rate constant. The kinetics were derived by Pitt et al. (Pitt, C. G., Jeffcoat, A. R., Zweidinger, R. A., Schindler, A., Sustained Drug Delivery Systems.1. Permeability of Poly(Epsilon-Caprolactone), Poly(Dl-Lactic Acid), and Their Copolymers. Journal of Biomedical Materials Research, 1979. 13(3): p. 497-507), and were again supported by Tsuji (Tsuji, H., Polylactides. 4 ed. Biopolymer, ed. A. Steinbüchel. 2001, Weinheim: Chichester: Wiley-VCH. 129-177).

The morphology of PLA (i.e., size and shape) plays an important role in its hydrolytic degradation (Li, S., Hydrolytic Degradation Characteristics of Aliphatic Polyesters Derived from Lactic and Glycolic Acids. Journal of Biomedical Materials Research Part B: Applied Biomaterials, 1999. 48(3): p. 342-353). If the size is very small as in the case of micro-particles, slim fibers, or thin films, the degradation should be slower than for large-sized materials because in the former case, no autocatalytic degradation occurs because of the easier diffusion of oligomers and the neutralization of carboxyl end groups (Li, S., Hydrolytic Degradation Characteristics of Aliphatic Polyesters Derived from Lactic and Glycolic Acids. Journal of Biomedical Materials Research Part B: Applied Biomaterials, 1999. 48(3): p. 342-353).

Controlled Release of Pesticides

The coating of pesticides using a polymer, a form of microencapsulation technology, has significant commercial value for improved resistance of pesticides to photolytic degradation and runoff. The coating can be a single polymer film completely entrapping the pesticide (such as single-core microcapsule) or it can be blended with the pesticide such that the pesticide is homogeneously distributed as a distinct second phase throughout the polymer continuous phase (commonly described as microsphere or multicore particle). If the polymer and pesticide are miscible and solidification occurs above ambient temperature, then films can be prepared.

Microencapsulation is not widely used because of the perceived hurdles associated with the cost. Low-cost biodegradable polymers with possible agricultural utility have been developed and commercialized. The range of physical properties of the polymers and their varied degradation rates permit the selection of a polymer to match a customized release rate.

There is therefore a need in the art for biodegradable polymers that hydrolyze quickly in the environment. There is also a need for polymer coatings for controlled release of pesticides into the environment for agricultural applications.

Citation or identification of any reference in Section 2, or in any other section of this application, shall not be considered an admission that such reference is available as prior art to the present invention.

SUMMARY OF THE INVENTION

A polymeric material is provided for release of a compound of interest comprising a polymeric matrix material; a second polymeric material incorporated in the polymeric matrix material; and the compound of interest incorporated in the polymeric matrix material; wherein the polymeric matrix material is a hydrophobic polymeric material and the incorporated second polymeric material is a hydrophilic polymeric material, or the polymeric matrix material is a hydrophilic polymeric material and the incorporated second polymeric material is a hydrophobic polymeric material.

In one embodiment, the content loading of the incorporated second polymeric material is in the range of 0.0001%-50% of the weight of the matrix material. In another embodiment, the content loading of the incorporated second polymeric material is in the range of 0%-50% of the weight of the matrix material. Thus in some embodiments, the second polymeric material can be omitted and the polymeric material comprise the polymeric matrix material and the compound of interest.

In another embodiment, the incorporated second polymeric material is covalently associated with or mechanically entrapped within the matrix material.

In another embodiment, release of the compound of interest is controlled release.

In another embodiment, the polymeric material is biodegradable. In preferred embodiments, the entire polymeric material is biodegradable. In other, less preferred embodiments, one or more components may not be biodegradable.

In another embodiment, the hydrophobic polymeric material is lipophilic or lipophobic.

In another embodiment, the hydrophobic polymeric matrix material and the incorporated hydrophilic polymeric material form nanocomposite fibers.

In another embodiment, the polymeric material is in the form of a fiber, filament, nonwoven fabric, film, coating, pellet, capsule, plastic shape, powder, granule, gel, droplet or other suitable shape known in the art.

In another embodiment, the hydrophobic polymeric matrix material can be, but is not limited to, poly(lactic acid) (PLA), poly α hydroxyl acid, poly glycolic acid (PGA), poly(lactic acid) (PLA, PLLA, PDLA, or poly lactide), poly ε caprolactone (PCL), polybutylene succinate (PBSU), polyethylene succinate (PESU), polyesteramides (PEA) or polyhydroxybutylvalerate In another embodiment, the hydrophilic polymeric material can be, but is not limited to, cellulose, starch, lignin, keratin, fibroin, polysaccharides, proteins, polyvinylalcohol (PVOH) or polyvinylacetate (PVA).

In another embodiment, the incorporated polymeric material has the form of nanofibrils, nanocrystals, nanoparticles, droplets or phase-separated domains within the polymeric matrix material.

In a specific embodiment, the hydrophobic matrix material is PLA and the hydrophilic second polymeric material is cellulose.

In another embodiment, the polymeric matrix material is PLA and is hydrophobic, the incorporated polymeric material is cellulose and is hydrophilic, the cellulose forms nanofibrils and the polymeric material is in the form of a fiber.

In another embodiment, the polymeric material is a fiber, film or powder, and the water contact angle of the fiber, film or powder is 0-140°.

In another embodiment, the polymeric material is a non-woven fabric, and the water absorbance of the fabric is 0-30 times the fabric weight.

In another embodiment, the polymeric material has a hydrolytic degradation rate that increases with increased proportion of the hydrophilic polymeric material.

In another embodiment, the degradation is enzymatic, microbial or photolytic.

In another embodiment, a biodegradable polymeric material for release of a compound of interest is provided comprising a polymeric matrix material and the compound of interest incorporated in the polymeric matrix material. In certain embodiments, the biodegradable polymeric material can comprise a second polymeric material incorporated in the matrix material.

A chemical delivery system for controlled delivery of a compound of interest is also provided, wherein the chemical delivery system comprises the polymeric material.

In one embodiment, the release rate of the compound of interest is controlled by varying the composition of hydrophilic polymeric material to hydrophobic polymeric material.

In another embodiment, the compound of interest can be, but is not limited to, a fertilizer, nutrient, soil amendment, mineral, plant growth regulator (e.g., plant growth hormone or phytohormone), pheromone, kairomone, allomone, repellent or pesticide.

In another embodiment, the pesticide can be, but is not limited to, an acaricide, algicide, avicide, bactericide, fungicide, herbicide, insecticide, mating disrupter, molluscicide, nematicide, rodenticide or virucide.

In another embodiment, the chemical delivery system is a non-woven fabric. A method for preparing a polymeric material for release of a compound of interest is also provided, wherein the polymeric material comprises a polymeric matrix material and the compound of interest. The method can comprise: (a) preparing a solution of the polymeric matrix material; (b) suspending or dissolving the second polymeric material in the solution; (c) suspending or dissolving the compound of interest in the solution; and (d) preparing polymeric material, wherein the step of preparing the polymeric material comprises subjecting the solution comprising the polymeric matrix material, the suspended or dissolved second polymeric material and the suspended or dissolved compound of interest to electrospinning, wet spinning, dry spinning, dry-jet wet spinning, melt spinning, gel spinning, electrospraying, casting, spray draying, aerosolizing, atomizing, monodispersing, melt blowing, molding, pressing, curing, or extruding.

In one embodiment, the polymeric material is in the form of a fiber, filament, nonwoven fabric, film, coating, pellet, capsule, plastic shape, powder, granule, gel, droplet or other suitable shape known in the art.

In another embodiment, the compound of interest is dispersed throughout the polymeric material.

A method for protecting a plant or a portion thereof from infestation by a pest or disease species is also provided. The method can comprise the step of adhering the polymeric material to the plant or portion thereof, wherein the polymeric material comprises a compound of interest that can be, but is not limited to, a pheromone, allomone, kairomone, repellent or pesticide.

Use of this method for remediating existing infestation of the plant or portion thereof is also provided.

Use of this method for protecting or remediating an infestation of fungus by a pest or disease species is also provided.

In one embodiment, the pesticide can be, but is not limited to, an acaricide, algicide, avicide, bactericide, fungicide, insecticide, mating disrupter, molluscicide, nematicide, rodenticide or virucide.

In another embodiment, the portion of the plant can be, but is not limited to, a root, seed, bulb, corm, rhizome, tuber, leaf, flower, fruit, reproductive structures, bud, stem, bark or foliage.

In another embodiment, the polymeric material is applied directly to the plant surface.

A method for protecting a plant or a portion thereof from infestation by a pest or disease species is also provided. The method can comprise the step of applying the polymeric material directly onto or into the substrate in which the plant or portion thereof is disposed, wherein the polymeric material comprises a compound of interest can be, but is not limited to, a pheromone, allomone, kairomone, repellent or pesticide.

Use of this method for remediating existing infestation of the plant or portion thereof is also provided.

Use of this method for protecting or remediating an infestation of fungus by a pest or disease species is also provided.

In one embodiment, the pesticide can be, but is not limited to, an acaricide, algicide, avicide, bactericide, fungicide, insecticide, mating disrupter, molluscicide, nematicide, rodenticide or virucide.

In another embodiment, the portion of the plant can be, but is not limited to, a root, seed, bulb, corm, rhizome, tuber, leaf, flower, fruit, reproductive structures, bud, stem, bark or foliage.

In another embodiment, the substrate can be soil, a soilless substrate (e.g., potting soil, rock wool, perlite, vermiculite, etc.), or other agricultural substrate or substrate for growing plants.

A method for controlled release of a compound of interest into a desired location is also provided. The method can comprise the step of contacting the polymeric material to the desired location.

In one embodiment, the desired location is soil or a soilless substrate.

In another embodiment, the desired location is a body of water (e.g., for application of an aquatic herbicide).

In another embodiment, the method comprises the step of applying the polymeric material to a substrate associated with the desired location.

In another embodiment, the substrate associated with the desired location is a plant or portion thereof.

In another embodiment, the portion of the plant can be, but is not limited to, a root, seed, bulb, corm, rhizome, tuber, leaf, flower, fruit, reproductive structures, bud, stem, bark or foliage.

In another embodiment, the compound of interest can be, but is not limited to, a fertilizer, nutrient, soil amendment, mineral, plant growth hormone, plant growth regulator, pheromone, kairomone, allomone, repellent or pesticide.

A method for regulating plant growth is also provided. The method can comprise applying the polymeric material onto the plant or a portion thereof, wherein the polymeric material comprises a compound of interest that is a plant growth regulator (e.g., a phytohormone).

In one embodiment, the portion of the plant can be, but is not limited to, a root, seed, bulb, corm, rhizome, tuber, leaf, flower, fruit, reproductive structures, bud, stem, bark or foliage.

In another embodiment, the polymeric material is applied directly to the surface of the plant or portion thereof.

In another embodiment, the regulating of plant growth is promoting rate of growth, inhibiting rate of growth, inhibiting maturation, enhancing competition against weeds, or stimulating germination.

A method for destroying a plant or a portion thereof is also provided. The method can comprise applying the polymeric material to the plant or portion thereof, wherein the polymeric material comprises a compound of interest that is an herbicide.

BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

DETAILED DESCRIPTION OF THE INVENTION

Figure 1:
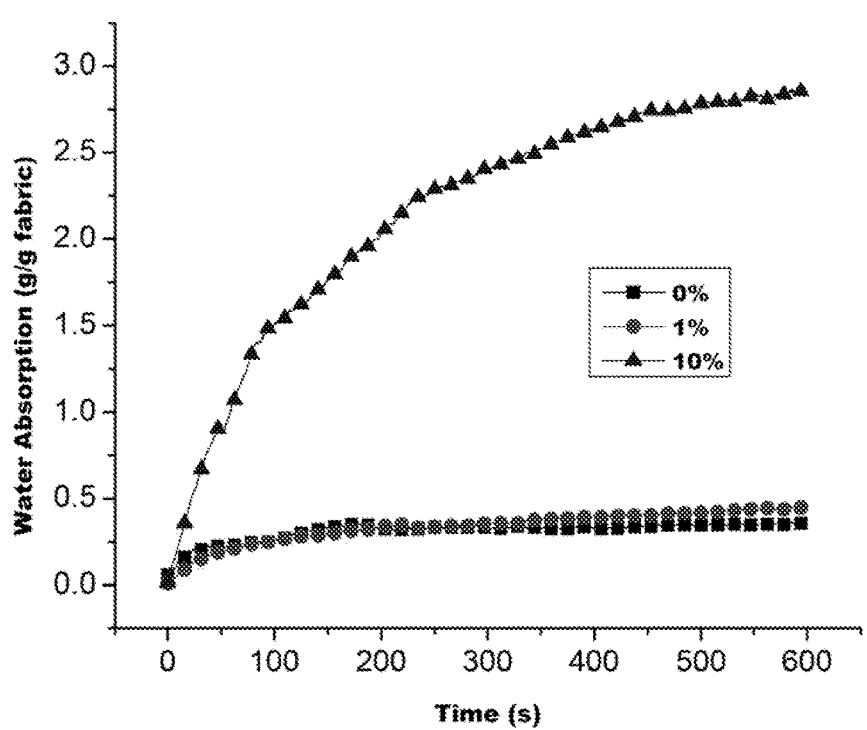
FIG. 1. Water absorption of the electrospun PLA/cellulose non-woven fabrics with different cellulose nanofibril content as a function of time. See Section 6.1 for details.

Fibers or other shapes are produced from either a blend of hydrophilic and hydrophobic biodegradable polymeric materials or a single polymer. These polymeric materials can be collected in the form of a non-woven fabric, singulated filaments, pellets, beads, beadlike chains or combinations of shapes. A compound (or substance of interest) can be incorporated inside the individual polymeric materials or by absorption into non-woven fabric. The compound of interest can then be delivered in a timed release fashion by diffusion of the compound from the polymeric material, during biodegradation or hydrolysis of the polymeric material, or by polymer softening. In another embodiment, the compound of interest can be delivered in a non-timed release delivery, e.g., an ingested or dermal toxicant. The release rate of the compound of interest is controlled by varying the composition of the polymeric material to control both diffusion rate of the compound of interest and biodegradation rate of the fiber. In other embodiments, the hydrophilic/hydrophobic biodegradable polymeric material can be in the form of a film, pellet, capsule or other suitable shape known in the art.

Regardless of form, this technology provides a new method to deliver and control the release rate of pesticides and related compounds in agricultural and non-agricultural settings. When adhered to plants or plant parts, polymeric materials incorporating pesticides can protect plants (e.g., young plants) or portions thereof (e.g., root, seed, bulb, corm, rhizome, tuber, leaf, flower, fruit, reproductive structures, bud, stem, bark or foliage) from insect and disease pests, or enhance germination and seedling establishment. In pellet or capsule form, pesticides can be delivered into seed furrows along with crop seeds, providing similar protection.

For clarity of disclosure, and not by way of limitation, the detailed description of the invention is divided into the subsections set forth below.

5.1. Hydrophilic/Hydrophobic Composite Polymeric Materials

A polymeric material is provided for release of a compound of interest. In one embodiment, the polymeric material comprises a polymeric matrix material, a second polymeric material incorporated in the polymeric matrix material, and the compound of interest incorporated in the polymeric matrix material. The polymeric matrix material can be a hydrophobic polymeric material and the incorporated second polymeric material can be a hydrophilic polymeric material, or the polymeric matrix material can be a hydrophilic polymeric material and the incorporated second polymeric material can be a hydrophobic polymeric material. In preferred embodiments, the entire polymeric material is biodegradable. In other, less preferred embodiments, one or more components may not be biodegradable.

In another embodiment, a biodegradable polymeric material for release of a compound of interest is provided comprising a polymeric matrix material and the compound of interest incorporated in the polymeric matrix material. In certain embodiments, the biodegradable polymeric material can comprise a second polymeric material incorporated in the matrix material.

The content loading of the incorporated second polymeric material can be in the range of 0%-50% of the weight of the matrix material. In other words, in some embodiments, the polymeric material comprises the polymeric matrix material and the compound of interest, but no second polymeric material is incorporated in the polymeric matrix material. In other embodiments, the content loading of the incorporated material can be in the range 010.0001%-50% of the weight of the matrix material. In a specific embodiment, the content loading of the hydrophilic polymeric material is in the range of 0-50% of the weight of the hydrophobic matrix material.

The incorporated polymeric material can be covalently associated with or mechanically entrapped within the matrix material. By varying the ratio of hydrophobic:hydrophilic components of the polymeric material, the rate of release of the compound of interest can be controlled.

In one embodiment, the release of the compound of interest is controlled release, e.g., the release of an entire desired amount of the compound at time 0 or a controlled rate of release of a desired amount of the compound over time. The hydrophilic/hydrophobic composite polymeric material can be formed into a fiber, non-woven fabric, film, coating, capsule, pellet, or other shape, or a powder, granule or gel using methods known in the art.

The hydrophobic polymeric matrix material can be, but is not limited to, poly(lactic acid) (PLA), poly α hydroxyl acid, poly glycolic acid (PGA), poly(lactic acid) (PLA, PLLA, PDLA, or poly lactide), poly ε caprolactone (PCL), polybutylene succinate (PBSU), polyethylene succinate (PESU), polyesteramides (PEA) or polyhydroxybutylvalerate (PHBV). The hydrophobic polymeric material can be lipophilic or lipophobic.

The hydrophilic polymeric material can be a natural material, e.g., cellulose, starch, lignin, keratin, fibroin, polysaccharides or proteins, or it can be a synthetic material, e.g., polyvinylalcohol (PVOH), and polyvinylacetate (PVA).

The incorporated polymeric material can have the form of nanofibrils, nanocrystals, nanoparticles, droplets or phase-separated domains within the polymeric matrix material. The hydrophilic polymeric material can be covalently associated with or mechanically entrapped within the hydrophobic polymeric matrix material.

The second polymeric material can be incorporated throughout the polymeric matrix material, and the portion of the incorporated polymeric material disposed on the surface of the polymeric material influences the hydrophilicity of the polymeric material, which in turn influences release rates of the compound of interest. Release rate can also be controlled by varying the form and/or diameter of the polymeric material, e.g., a fiber, pellet, etc. or by other methods well known in the art.

The polymeric material can be in the form of a fiber, filament, nonwoven fabric, film, coating, pellet, capsule, plastic shape, powder, granule, gel droplet or other suitable shape known in the art.

The incorporated polymeric material can have the form of nanofibrils, nanocrystals, nanoparticles, droplets or phase-separated domains within the polymeric matrix material.

In a specific embodiment, the polymeric material is in the form of a fiber wherein the polymeric matrix material is PLA and is hydrophobic, the incorporated second polymeric material is cellulose and is hydrophilic, and the cellulose forms nanofibrils.

The second polymeric material can be incorporated throughout the polymeric matrix material, and the portion of the incorporated polymeric material disposed on the surface of the polymeric material influences the hydrophilicity of the polymeric material, which in turn influences release rates of the compound of interest. Release rate can also be controlled by varying the form and/or diameter of the polymeric material, e.g., a fiber, pellet, etc. or by other methods well known in the art.

The polymeric material can comprise a compound of interest, wherein the compound of interest is incorporated in the polymeric material. In certain embodiments, the compound of interest can be, but is not limited to, a fertilizer, nutrient, soil amendment, mineral, plant growth hormone, plant growth regulator, pheromone, kairomone, allomone, repellent and pesticide. The pesticide can be any pesticide known in the art, e.g., acaricide, algicide, avicide, bactericide, fungicide, herbicide, insecticide, mating disrupter, molluscicide, nematicide, rodenticide or virucide.

In embodiments in which the polymeric material is a fiber, film or powder, the water contact angle of the fiber, film or powder can be 0-140°.

In embodiments in which the polymeric material is a nonwoven fabric, the water absorbance of the fabric can be 0-30 times the fabric weight.

The polymeric material can have a hydrolytic degradation rate that increases with increased proportion of the hydrophilic polymeric material. The degradation can be enzymatic, microbial or photolytic.

The Young's Modulus of the polymeric material can be 10-300 MPa.

5.2 Methods for Making Polymeric Materials

A method for preparing a polymeric material for release of a compound of interest is also provided, wherein the polymeric material comprises a polymeric matrix material, a second polymeric material incorporated in the polymeric matrix material, and the compound of interest incorporated in the polymeric material. The polymeric material can be according to any of the embodiments described above in Section 5.1. The polymeric matrix material can be a hydrophobic polymeric material and the incorporated second polymeric material can be a hydrophilic polymeric material, or the polymeric matrix material can be a hydrophilic polymeric material and the incorporated second polymeric material can be a hydrophobic polymeric material.

In one embodiment, the method can comprise: (a) preparing a solution of the polymeric matrix material; (b) suspending or dissolving the second polymeric material in the solution; (c) suspending or dissolving the compound of interest in the solution; and (d) preparing polymeric material.

In one embodiment, the step of preparing the polymeric material comprises subjecting the solution comprising the polymeric matrix material, the suspended or dissolved second polymeric material and the suspended or dissolved compound of interest to electrospinning, wet spinning, dry spinning, dry-jet wet spinning, melt spinning, gel spinning, electrospraying, casting, spray draying, aerosolizing, atomizing, monodispersing, melt blowing, molding, pressing, curing or extruding. In another embodiment, a powder can be prepared (e.g., by grinding or pulverizing) the polymeric material prepared in bulk by one of the above methods.

The polymeric material for release of a compound of interest can be made using any method known in the art that results in a roughly homogenous distribution of polymeric matrix material and the second polymeric material incorporated in the polymeric matrix material.

Electrospinning methods are well known in the art. Electrostatic fiber spinning or 'electrospinning' is an art-known method for forming fibers with submicron scale diameters through electrostatic forces. When an electrical force is applied at the interface of a liquid polymer, a charged jet is ejected. The jet initially extends in a straight line, then moves into a whipping motion caused by the electrohydrodynamic instability at the tip. As the solvent evaporates, the polymer is collected, e.g. onto a grounded piece of aluminum foil as a nonwoven mat (Kim, C. K., D S. Kim, S Y. Kang, M Marquez, and Y L. Joo, "Structural Studies of Electrospun Cellulose Nanofibers." Polymer, 2006. 47(14): p. 5097-5107).

Other art-known fiber manufacturing methods such as wet spinning, dry spinning, dry-jet wet spinning, melt spinning or gel spinning or electrospraying or spray-drying could also be used. The skilled practitioner will recognize that these techniques are suitable for forming many types of polymeric components into desired forms or shapes Dry spinning is an art-known technique commonly used to spin cellulose acetate fibers, and is a common industrial spinning method. The dope solution is composed of a cellulose acetate-acetone mixture containing approximately 15-30 wt % polymer. The dope solution is extruded from a spinneret, and the solution is drawn down to a roller at the bottom of the spinning column (Sano, Y., Drying Behavior of Acetate Filament in Dry Spinning. Drying Technology, 2001. 19(7): p. 1335-1359).

Preparation of solutions for the above spinning methods and other methods for polymer shaping can be carried out using methods known in the art.

In certain embodiments, the second polymeric material can be omitted and the polymeric material comprises the polymeric matrix material and the compound of interest.

The polymeric material can form a fiber, filament, nonwoven fabric, film, coating, pellet, capsule, plastic shape, powder, granule, gel, droplet or other suitable shape known in the art.

The compound of interest can be dispersed throughout the polymeric material.

In a specific embodiment (see also Section 6.1), the polymeric material comprises PLA as the hydrophobic polymeric matrix material and cellulose as the hydrophilic polymeric material.

Cellulose Nanofibrils

Preparation of hydrophilic polymeric nanofibrils can be carried out using methods known in the art. The starting material to produce cellulose nanofibrils, for example, can be microcrystalline cellulose (MCC) powder, which is treated by acid hydrolysis in a concentrated sulfuric acid solution. After hydrolysis, the cellulose suspension can be further dispersed by ultrasound treatment. The hydrolyzed cellulose can be separated from the suspension by centrifugation, dialyzed against distilled and deionized water with ion-exchange. The final aqueous suspension can be centrifuged and freeze-dried.

In one embodiment cellulose nanofibrils can be prepared by sulfuric acid hydrolysis and incorporated into PLA/DMF solutions by ultrasonication before electrospinning. For example, freeze-dried cellulose nanofibrils can be re-dispersed by ultrasonication in DMF. PLA powders are then added to the cellulose/DMF suspension and the mixture dissolved in DMF. Any PLA known in the art can be used, e.g., PLA 6201 D (MW=143,000, PDI=1.8) and PLA 4042 D (MW=211,332, PDI=1.9). Cellulose nanofibrils (e.g., 1-10% on the weight of PLA) can be added to the PLA/DMF solution (e.g., 20-25% PLA in DMF). During electrospinning, the suspension temperature in the syringe and needle can be controlled using methods known in the art.

Fiber morphology can be optimized using methods known in the art by molecular weight of PLA, polymer concentration in DMF, syringe temperature, needle size and high voltage. After the optimal conditions are found, the effects of the cellulose nanofibril content on the physical properties of the electrospun nanocomposite fibers can be characterized using methods known in the art (see Section 5.3).

5.3 Methods for Characterizing Polymeric Materials

Surface elemental composition analysis can be conducted to study the presence of cellulose nanofibrils at the surface of PLA nanocomposite fibers. Crystallinity of the electrospun PLA/cellulose nanocomposite fibers can be investigated by methods known in the art, for example, by differential scanning calorimetry (DSC) or wide angle X-ray diffraction (WAXD).

The influence of cellulose nanofibril content on the hydrophilicity of the electrospun non-woven fabrics can be studied by measuring water absorption. Mechanical properties of the electrospun PLA/cellulose non-woven fabrics can be investigated.

Characterization of Hydrophilic/Hydrophobic Nanocomposite Polymeric Fibers

Hydrophilic/hydrophobic nanocomposite fibers can be characterized using methods known in the art. The morphology of hydrophilic/hydrophobic nanocomposite fibers can be evaluated, for example, by transmission electron microscopy (TEM).

The surface composition of the hydrophilic/hydrophobic nanocomposite fibers s can be evaluated by X-ray photoelectron spectroscopy (XPS).

Hydrophilicity of the hydrophilic/hydrophobic nanocomposite fibers can be evaluated by measuring water absorption of the fibers or non-woven fabrics firmed from the fibers. The water absorption can be studied, for example, through the measurement of the weight change with time when hydrophilic/hydrophobic non-woven fabrics are in contact with water using a wettability apparatus.

The water contact angle of hydrophilic/hydrophobic nanocomposite fibers can be measured by the sessile drop method using a contact angle analyzer.

Wide angle X-ray diffraction (WAXD) can be conducted to qualitatively analyze the crystallization of the hydrophilic/hydrophobic nanocomposite fibers.

Thermal properties of the hydrophilic/hydrophobic nanocomposite fibers can be investigated by differential scanning calorimetry (DSC).

Mechanical properties of hydrophilic/hydrophobic nanocomposite fibers in non-woven fabrics can be studied, e.g., with a universal testing machine.

The presence and quantity of hydrophilic nanocrystals (e.g., cellulose) at the surface of the hydrophilic/hydrophobic nanocomposite fibers can be characterized. The influence of hydrophilic nanoctystal content on the hydrophilicity of non-woven fabrics formed from the hydrophilic/hydrophobic nanocomposite fibers can be studied by measuring the water absorption and water contact angle of the non-woven fabrics. The hydrolytic degradation behaviors of the hydrophilic/hydrophobic nanocomposite fibers, spun from solutions containing e.g., 1%-10% suspended hydrophilic nanocrystals in phosphate buffer solution (PBS pH 7.4) can be investigated and compared with controls.

Degraded nanocomposite fibers can be evaluated. The morphological changes of hydrophilic/hydrophobic nanocomposite fibers can be observed by field emission scanning electron microscopy.

The molecular weight of the hydrophobic polymeric matrix material from the nanocomposite fibers can be determined during hydrolytic degradation by size exclusive chromatography (SEC).

5.4 Chemical Delivery System for Controlled Release Delivery of a Compound of Interest A chemical delivery system for controlled release delivery of a compound (or substance) of interest is also provided. A chemical delivery system for controlled delivery of a compound of interest comprising the polymeric material and the compound of interest, wherein the compound of interest is incorporated in the polymeric material. The release rate of the compound of interest is controlled by varying the ratio of hydrophilic polymeric material to hydrophobic polymeric material to control both diffusion rate of the compound of interest and biodegradation rate of the polymeric material.

The compound of interest can be any substance for which delivery is desired, e.g., a fertilizer, nutrient, soil amendment, mineral, plant growth hormone, plant growth regulator, pheromone, kairomone, allomone, repellent or pesticide. The pesticide can be, but is not limited to, an acaricide, algicide, avicide, bactericide, fungicide, herbicide, insecticide, mating disrupter, molluscicide, nematicide, rodenticide or virucide.

The chemical delivery system can comprise polymeric material in the form of a fiber, film, coating, pellet, capsule, or other shape, or a powder, granule or gel. In a specific embodiment, the chemical delivery system comprises a non-woven polymeric fabric. Regardless of form, this technology can be used to deliver and control the release rate of pesticides and related compounds in agricultural and non-agricultural settings.

In a specific embodiment, the chemical delivery system delivers an agricultural chemical, for example, a fertilizer, nutrient, soil amendment, mineral, plant growth regulator (e.g., plant growth hormone or phytohormone), pheromone, kairomone, allomone, repellent and pesticide.

When adhered to seeds, for example, fibers or powder or film coatings with an agricultural chemical such as a pesticide or seed growth stimulant can protect seeds and young plants from insect and disease pests or enhance their germination and establishment. In pellet or capsule form, the agricultural chemical can be delivered into seed furrows along with crop seeds, providing similar protection. In other embodiments, the agricultural chemical can be a nutrient or fertilizer that can be delivered into seed furrows along with crop seeds to promote growth.

The compound of interest can be incorporated into a nanocomposite polymeric material, e.g., fibers spun from a suspension of hydrophilic/hydrophobic polymeric materials as described above. Hydrophilic nanocrystals or nanofibrils can be dispersed in a solvent known in the art, such as dimethyl formamide (DMF), and then hydrophobic polymeric matrix material and the compound of interest can be added. The suspension can be heated to dissolve the hydrophobic polymeric matrix material in the solvent and spun to produce nanocomposite fibers. Section 6.3 sets forth the details of one method for incorporating a compound of interest into PLA/cellulose nanocomposite fibers.

Alternatively, the suspension can be coated, formed, pressed or shaped into various films, coatings, pellets, capsules or other plastic or moldable shapes.

Release of the compound of interest from the hydrophilic/hydrophobic nanocomposite polymeric fibers can be characterized using methods known in the art, e.g., diffusion studies. Hydrophilic/hydrophobic nanocomposite polymeric fibers can be identified with desired release rates.

The concentration of the compound of interest in the hydrophilic/hydrophobic nanocomposite polymeric fibers can be characterized using methods known in the art, e.g., Liquid Chromatography/Mass Spectroscopy (LC/MS). The compound of interest can be further identified using mass spectroscopy.

The thermal properties of the polymeric matrix material from hydrophilic/hydrophobic nanocomposite polymeric fibers containing the compound of interest can be determined using methods known in the art, e.g., DSC studies.

In one embodiment, hydrophilic/hydrophobic nanocomposite polymeric fibers form a non-woven fabric. Production of non-woven fabrics from spun (e.g., electrospun) fibers is well known in the art. The surface chemistry of the non-woven fabrics can be controlled by controlling the ratio of hydrophilic to hydrophobic (or lipophilic) fibers. Porosity and pore size within the non-woven fabrics can be controlled by the spinning process, using methods well known in the art.

Non-woven fabrics with controlled structure and surface chemistry can be produced by controlling polymer solution properties and spinning conditions.

Compounds of interest can be selectively included within the fibers forming the non-woven fabrics by dissolving those chemicals with the polymers before spinning or by selective adsorption after spinning.

Performance of non-woven fabrics in adsorption and desorption of agricultural chemicals can be modeled using dyes with known $K_{ow}$ values.

Non-woven fabrics composed of biodegradable polymers can biodegrade in aerobic and anaerobic environments and the biodegradation process can be studied, e.g., the release of any adsorbed chemicals not released via desorption/diffusion phenomena.

Models developed statistically from experimental data (using methods known in the art) and mechanistically (from desorption, diffusion and biodegradation kinetics) can be used to predict the optimum non-woven fabric structure and surface chemistry for timed release delivery of the compound of interest. Bioassays known in the art can be used to confirm the accuracy of the models.

A method for protecting a plant or a portion thereof from infestation by a pest or disease species is also provided. The method can comprise the step of adhering the polymeric material to the plant or portion thereof, wherein the polymeric material comprises a compound of interest selected from the group consisting of pheromone, allomone, kairomone, repellent and pesticide.

Use of this method for remediating existing infestation of the plant or portion thereof is also provided.

Use of this method for protecting or remediating an infestation of a fungus (rather than a plant), e.g., mushrooms or other commercially grown fungi, by a pest or disease species is also provided.

In one embodiment, the pesticide is selected from the group consisting of acaricide, algicide, avicide, bactericide, fungicide, insecticide, mating disrupter, molluscicide, nematicide, rodenticide and virucide.

In another embodiment, the portion of the plant is selected from the group consisting of root, seed, bulb, corm, rhizome, tuber, leaf, flower, fruit, reproductive structures, bud, stem, bark and foliage.

In another embodiment, the polymeric material is applied directly to the plant surface.

A method for protecting a plant or a portion thereof from infestation by a pest or disease species is also provided. The method can comprise the step of applying the polymeric material directly onto or into the substrate in which the plant or portion thereof is disposed, wherein the polymeric material comprises a compound of interest selected from the group consisting of pheromone, allomone, kairomone, repellent and pesticide.

Use of this method for remediating existing infestation of the plant or portion thereof is also provided.

Use of this method for protecting or remediating an infestation of a fungus (rather than a plant), e.g., mushrooms or other commercially grown fungi, by a pest or disease species is also provided.

In one embodiment, the pesticide is selected from the group consisting of acaricide, algicide, avicide, bactericide, fungicide, insecticide, mating disrupter, molluscicide, nematicide, rodenticide and virucide.

In another embodiment, the portion of the plant is selected from the group consisting of root, seed, bulb, corm, rhizome, tuber, leaf, flower, fruit, reproductive structures, bud, stem, bark and foliage.

In another embodiment, the substrate is a substrate for growing a plant, e.g., an agricultural substrate such as soil or a soilless substrate (e.g., potting soil, rock wool, perlite, vermiculite, etc.).

A method for controlled release of a compound of interest into a desired location is also provided. The method can comprise the step of contacting the polymeric material to the desired location.

In one embodiment, the desired location is a substrate for growing a plant, e.g., an agricultural substrate such as soil or a soilless substrate (e.g., potting soil, rock wool, perlite, vermiculite, etc.).

In another embodiment, the desired location is a body of water (e.g., for application of an aquatic herbicide).

In another embodiment, the method comprises the step of applying the polymeric material to a substrate associated with the desired location.

In another embodiment, the substrate associated with the desired location is a plant or portion thereof.

In another embodiment, the portion of the plant is selected from the group consisting of root, seed, bulb, corm, rhizome, tuber, leaf, flower, fruit, reproductive structures, bud, stem, bark and foliage.

In another embodiment, the compound of interest is selected from the group consisting of fertilizer, nutrient, soil amendment, mineral, plant growth hormone, plant growth regulator, pheromone, kairomone, allomone, repellent and pesticide.

A method for regulating plant growth is also provided. The method can comprise applying the polymeric material onto the plant or a portion thereof, wherein the polymeric material comprises a compound of interest that is a plant growth regulator (e.g., a phytohormone).

In one embodiment, the portion of the plant is selected from the group consisting of root, seed, bulb, corm, rhizome, tuber, leaf, flower, fruit, reproductive structures, bud, stem, bark and foliage.

In another embodiment, the polymeric material is applied directly to the surface of the plant or portion thereof.

In another embodiment, the regulating of plant growth is promoting rate of growth, inhibiting rate of growth, inhibiting maturation, enhancing competition against weeds, or stimulating germination.

A method for destroying a plant or a portion thereof is also provided. The method can comprise applying the polymeric material to the plant or portion thereof, wherein the polymeric material comprises a compound of interest that is an herbicide.

The following examples are offered by way of illustration and not by way of limitation.

EXAMPLES 6.1 Example 1: Nanocomposite Fibers Electrospun from Poly(Lactic Acid)/Cellulose Abstract This example demonstrates the electrospinning of PLA/cellulose nanocomposite fibers at elevated temperature from Poly(lactic acid) (PLA) in dimethylformamide (DMF) solutions containing suspended cellulose nanofibrils. Cellulose nanofibrils were prepared by sulfuric acid hydrolysis. The rod-like morphology of cellulose nanofibrils was studied by transmission electron microscopy (TEM). Electrospinning conditions were optimized to form PLA/cellulose nanocomposite fibers with uniform diameters and smooth morphology at cellulose nanofibril content loadings of 0%, 1 wt % and 10 wt % (on the weight of PLA). Surface elemental composition analysis confirmed the presence of cellulose nanofibrils at the surface of PLA nanocomposite fibers. Incorporation of cellulose nanofibrils increased PLA crystallinity in the resulting nanocomposite fibers. As the cellulose nanofibril content increased, the electrospun non-woven fabrics became increasingly hydrophilic. The strength of the electrospun non-woven fabrics was improved by the incorporation of cellulose nanofibrils into PLA. The elongation of the electrospun non-woven fabrics was decreased as the cellulose nanofibrils incorporated into PLA.

Introduction

Electrospinning provides a method to produce nanofibers with minute diameter and large surface to mass ratio. Moreover, a significant implication of the mechanism of electrospinning is that it allows a bicomponent system to have properties from each of the polymeric components. In this example, one of the polymers (PLA) contributed to hydrophobicity while the other (cellulose) enhanced the hydrophilicity of the resulting nanocomposite fibers.

Poly(lactic acid) (PLA) is a highly versatile, biodegradable, aliphatic polyester that can be derived from 100% renewable resources, such as corn and sugar beets. Several researchers have reported successful submicron PLA fibers formation via electrospinning (Fong, H. D. H. R., Electrospinning and the Formation of Nanofibers, in Structure Formation in Polymeric Fibers, D. R. Salem, Editor. 2000, Hanser Gardner Publications, Inc: Cincinnati. p. 225-246; Kim, K. W., Y. L. Joo, and E. P. Giannelis, Effects of Nanoclay on Molecular Structures of Poly(L-lactic) Acid in Electrospinning. Symposium on Polymeric Nanofibers, ACS Fall Meeting, 2003; Zeng, J., et al., Enzymatic degradation of poly(L-lactide) and poly(epsilon-caprolactone) electrospun fibers. Macromolecular Bioscience, 2004. 4(12): p. 1118-1125). Additionally, a wide variety of materials have been incorporated into electrospun PLA fibers to tailor the fibers for particular end uses. Biotin has been incorporated into PLA through electrospinning to prepare membrane substrates for biosensors (Li, D. P., M. W. Frey, and A. J. Baeumner, Electrospun polylactic acid nanofiber membranes as substrates for biosensor assemblies. Journal of Membrane Science, 2006. 279(1-2): p. 354-363). Carbon nanotubes have been incorporated into electrospun PLA fibers for potential use as bone graft materials (Khan, S. S., Carbon nanotube based nanocomposite fibril for cartilage regeneration. 2003, Drexel University). Kenawy et al. (Kenawy, E. R., et al., Release of tetracycline hydrochloride from electrospun poly(ethylene-co-vinylacetate), poly(lactic acid), and a blend. Journal of Controlled Release, 2002. 81(1-2): p. 57-64) have incorporated tetracycline hydrochloride in electrospun non-woven fabrics of PLA and poly(ethylene-co-vinylacetate) for controlled release delivery. Zhou et al. (H. Zhou, K. W. K., E. P. Giannelis, Y. L. Joo, Chapter 16. Nanofibers from Poly (L-Lactic) Acid Nanocomposites: Effects of Nanoclay on Molecular Structures. Polymeric Nanofibers, ACS Symposium Series Book, ed. D. H. Reneker and H. Fong. Vol. 918. 2006, Washington, D.C.: American Chemical Society. 217-230) reported that inclusion of nanoclay enhanced the formation of oriented structures in electrospun PLA fibers, which gave rise to substantial cold crystallization. Electrospinning induced PLA crystal structure with a fibrillar morphology and the addition of nanoclay enhanced the formation of crystal structure, and hence significantly increased the mechanical properties of the electrospun fibers mats and influenced the biodegradability.

Cellulose in the form of nanofibrils is the load-bearing constituent in plants. Cellulose nanofibrils are arranged in bundles of 10-50 nm in width, which have fine diameter, large aspect ratio (fiber length divided by diameter), biocompatibility, high strength and modulus as well as other favorable physical properties associated with the highly crystalline extended chain conformation (W. J. Orts, L. G., R. H. Marchessault, J. F. Revol, Enhanced Ordering of Liquid Crystalline Suspensions of Cellulose Microfibrils: A Small Angle Neutron Scattering Study. Macromolecules, 1998. 31: p. 5717-5725). In recent years, the mechanical properties of cellulose crystals have attracted attention for application as reinforcing fillers in polymer nanocomposites (Roman, M. and W. T. Winter, Effect of sulfate groups from sulfuric acid hydrolysis on the thermal degradation behavior of bacterial cellulose. Biomacromolecules, 2004. 5(5): p. 1671-1677). Samir et al. (Samir, M., et al., Cellulose nanocrystals reinforced poly(oxyethylene). Polymer, 2004. 45(12): p. 4149-4157) used cellulose nanocrystals as reinforcement for poly(oxyethylene) (POE) nanocomposite materials. They reported that the glass-rubber transition temperature, melting temperature, and degree of crystallinity of POE were not influenced significantly by the cellulosic filler when the cellulose nanocrystal content was below 10 wt %. Researchers have successfully produced cellulose nanofibrils with an average length smaller than 200 nm (Dong, X. M., J. F. Revol, and D. G. Gray, Effect of microcrystallite preparation conditions on the formation of colloid crystals of cellulose. Cellulose, 1998. 5(1): p. 19-32). However, once the nano-fibrillated cellulose is dried, it is very difficult to disperse and keep into individual nano-shape since hydrogen bonds cause strong adhesion between the individual nanofibrils. Marcovich et al. (Marcovich, N. E., et al., Cellulose micro/nanocrystals reinforced polyurethane. Journal of Materials Research, 2006. 21(4): p. 870-881) reported that a stable suspension of cellulose nanocrystals was obtained in DMF. After the hydrolysis treatment, the cellulose nanocrystals were freeze-dried and re-dispersed by ultrasonic agitation in DMF.

In this example, PLA/cellulose nanocomposite fibers were electrospun at elevated temperature from PLA/DMF solutions containing suspended cellulose nanofibrils and collected as randomly oriented non-woven fabrics. Cellulose nanofibrils were prepared by sulfuric acid hydrolysis and incorporated into PLA/DMF solutions by ultrasonication before electrospinning. Fiber morphology was optimized by molecular weight of PLA, polymer concentration in DMF, syringe temperature, needle size and high voltage. After the optimal conditions were found, the effects of the cellulose nanofibril content on the physical properties of the electrospun nanocomposite fibers were studied. Surface elemental composition analysis was conducted to study the presence of cellulose nanofibrils at the surface of PLA nanocomposite fibers. Crystallinity of the electrospun PLA/cellulose nanocomposite fibers was investigated by differential scanning calorimetry (DSC) and wide angle X-ray diffraction (WAXD). Influence of cellulose nanofibril content on the hydrophilicity of the electrospun non-woven fabrics was studied by measuring the water absorption. Mechanical properties of the electrospun PLA/cellulose non-woven fabrics were investigated.

Materials

Microcrystalline cellulose powder (MCC, extra pure, average particle size 90 µm) was purchased from Acros Organics (Geel, Belgium). PLA 6201 D (Mw=143,000, PDI=1.8) and PLA 4042 D (Mw=211,332, PDI=1.9) were supplied by Cargill Dow (Minnetonka, Minn.). Ion exchange Rexyn 1-300 (H—OH) was purchased from Acros Organics (Geel, Belgium). Sulfuric acid (96.1%, density=1.84 g/cm$^3$) was purchased from J. T. Baker (Phillipsburg, N.J.). N,N-dimethylformamide (DMF) was purchased from Mallinckrodt Laboratory Chemicals (Phillipsburg, N.J.). All regents were used without further purification.

Methods and Techniques

Preparation of Cellulose Nanofibrils

The preparation of cellulose nanofibrils was carried out using methods modified after Roman et al. (Roman, M. and W. T. Winter, Effect of sulfate groups from sulfuric acid hydrolysis on the thermal degradation behavior of bacterial cellulose. Biomacromolecules, 2004. 5(5): p. 1671-1677) and Dong et al. (Dong, X. M., J. F. Revol, and D. G. Gray, Effect of microcrystallite preparation conditions on the formation of colloid crystals of cellulose. Cellulose, 1998. 5(1): p. 19-32). The starting material to produce cellulose nanofibrils was microcrystalline cellulose (MCC) powder. The MCC was treated by acid hydrolysis in a concentrated sulfuric acid solution (64 wt % sulfuric acid in water). The ratio of MCC to acid solution was 1 gram to 8.75 ml. The treatment was conducted at 45° C. for 1 hr under strong stirring. After the hydrolysis treatment, the cellulose suspension was further dispersed by an ultrasound treatment (10 min at full power) with an ultrasonic liquid processor (Misonix Sonicator® 3000) in an ice bath. The hydrolyzed cellulose was rinsed three times with distilled and deionized water, and separated from the suspension by centrifugation (13500 rpm, 10 min) after each wash. The hydrolyzed cellulose was then dialyzed against distilled and deionized water with ion-exchange (Rexyn 1-300 (H—OH)) for 3 days with 12K-14K molecular weight cutoff dialysis tubing. The final aqueous suspension was centrifuged and freeze-dried (Labconco Freeze Dry System/Freezone® 4.5) to avoid re-agglomeration of the cellulose crystals. The final supernatant of the cellulose suspension was neutral.

Preparation of Electrospinning Suspensions and Nanocomposite Fibers

The freeze-dried cellulose nanofibrils were re-dispersed by ultrasonication in DMF. PLA powders were then added to the cellulose/DMF suspension and the mixture was brought to 70° C. for fully dissolution of PLA in DME Two types of PLA were used: PLA 6201 D (Mw=143,000, PDI=1.8) and PLA 4042 D (Mw=211,332, PDI=1.9). 0.1 wt %, and 10 wt % cellulose nanofibrils (on the weight of PLA) were added to 22 wt % PLA 6201 D/DMF solutions and 22 wt % and 25 wt % of PLA 4042 D/DMF solutions. During electrospinning, the suspension temperature in the syringe and needle was controlled by a shielded heating unit pre-heated to the temperature and controlled to ±5° C. with a Watlow controller (St. Louis, Mo.) (Joo, Y. L. and H. Zhou, Apparatus and method for elevated temperature electrospinning, in US Patent. 2004, Ser. No. 10/965,813). All samples were collected for five hours.

Microscopy

One drop (8 µL) of approximately 0.1 wt % cellulose nanofibrils in DMF was allowed to dry on a Formvar and carbon coated grid (200 mesh). The dried cellulose nanofibrils were stained with ruthenium tetra oxide (RuO$_4$) vapor on the TEM grids. TEM images were taken at 120 kV with a Technai T12 transmission electron microscope (TEM). The morphology of electrospun nanocomposite fibers was examined with Leica 440 scanning electron microscopy (SEM) after being coated with Au—Pd. The distribution of cellulose nanofibrils in PLA/cellulose nanocomposite fibers was examined with Technai T12 TEM. The nanocomposite fibers were directly collected on the TEM grids for about 2 seconds and then stained with RuO$_4$ before TEM study.

Surface Composition

The surface composition of the electrospun PLA/cellulose nanocomposite fibers was evaluated by X-ray photoelectron spectroscopy (XPS) (Surface Science Instruments, Model SSX100). Al Kα X-rays were used as the source. The carbon and oxygen scans were high resolution with pass energy of 50V. The survey scan had pass energy of 150V. Data were collected at 55° take-off angle (TOA). Overlapping peaks were resolved into their individual components by using a curve-fitting program (CasaXPS v.2.3.12).

Water Contact Angle Measurement

Hydrophilicity of the electrospun PLA/cellulose nanocomposite fibers was studied by measuring the water absorption of the electrospun non-woven fabrics. The water absorption was studied through the measurement of the weight change with time when the electrospun PLA/cellulose non-woven fabrics were in contact with water using a Sigma 700 (KSV Instruments) wettability apparatus. The electrospun non-woven fabrics cut into 0.5 cm×3 cm rectangles were attached to small copper-wire hooks with an adhesive and allowed to dry at room temperature at least 12 hrs. Four specimens were tested for each sample.

The water contact angle of the electrospun PLA/cellulose nanocomposite fibers was measured by the sessile drop method (Owens, D. K. and R. C. Wendt, Estimation of Surface Free Energy of Polymers. Journal of Applied Polymer Science, 1969. 13(8): p. 1741) using a contact angle analyzer (Imass, Model CAA2). Ten specimens were tested for each sample.

Wide Angle X-Ray Diffraction (WAXD)

Wide angle X-ray diffraction (WAXD) was conducted with a Scintag PADX diffractometer using an incident X-ray wavelength of 1.542 Å. Samples were scanned in the range of 2θ from 2° to 39.98° at a step rate of 0.03° to qualitatively analyze the crystallization of the electrospun PLA/cellulose nanocomposite fibers. The resulting plot of X-ray intensity versus 2θ was analyzed by the profile fitting program DMSNT ThermoARL.

Differential Scanning Calorimetry (DSC)

Thermal properties of the electrospun PLA/cellulose nanocomposite fibers were investigated by Differential scanning calorimetry (DSC) (DSC 2920, TA Instruments Inc.). Approximately 10 mg of samples were loaded and heated in a nitrogen atmosphere at a rate of 10° C./min from 0° C. to 200° C.

Tensile Test

Mechanical properties of the electrospun PLA/cellulose non-woven fabrics were studied with a universal testing machine (INSTRON 5566) under a crosshead speed of 20 mm/min at room temperature. All samples were prepared in the form of standard dumb-bell shape according to ASTM D638-02a by die cutting from the electrospun non-woven fabrics. Ten specimens for each sample were tested.

Results and Discussion

Characterization of Cellulose Nanofibrils

The sulfuric acid hydrolysis of MCC caused the breakdown of cellulose microcrystals into rod-like fragments. The average length (L) and width (W) of cellulose nanofibrils are 124±35 nm and 9±2 nm respectively by measuring 50 single cellulose nanofibrils from the TEM images. The aspect ratio (L/W) of the cellulose nanofibrils is 14. These results are in agreement with the results reported in the literature (Marcovich, N. E., et al., Cellulose micro/nanocrystals reinforced polyurethane. Journal of Materials Research, 2006. 21(4): p. 870-881).The TEM images confirmed that cellulose nanofibrils can be re-dispersed into DMF by ultrasonication after freeze-dried, which is very favorable to the subsequent incorporation into PLA/DMF solution to form nanocomposite fibers.

Optimization of Electrospun Nanocomposite Fiber Morphology and Uniformity

The electrospinning conditions of 22 wt % PLA 6201 D in DMF with different cellulose nanofibril contents are shown in Table 1. Table 2 shows the electrospinning conditions of 22 wt % and 25 wt % PLA 4042 D in DMF with different cellulose nanofibril contents. The electrospun fiber samples are named as 22%-L-0%, 22%-L-1%, 22%-L-10%; 22%-H-0%, 22%-H-1%, 22%-H-10%; and 25%-H-0%, 25%-H-1%, 25%-H-10%,with 22% and 25% denoting the PLA concentration in PLA/DMF solutions, L denoting the lower molecular weight PLA 6201 D, H denoting the higher molecular weight PLA 4042 D, 0%, 1% and 10% denoting the cellulose nanofibril contents relative to the weight of PLA. To obtain continuously electrospinning, for the 22%-L and 25%-H suspension systems, the syringe temperature, needle size and high voltage had to be varied. While for the 22%-H, the electrospinning conditions could keep constantly and did not change with the increase of cellulose nanofibril contents. For parallel experiments, the suspension composition for electrospinning was optimized by the 22%-H system.

TABLE 1

The electrospinning conditions of 22 wt % PLA 6201 (Low Mw).

| | PLA/DMF Concentration (Mw = 143,000) 22 wt % | | |
|---|---|---|---|
| Cellulose % (w/w PLA) | 0 | 1 | 10 |
| Syringe T(° C.) | 70 ± 5 | 80 ± 5 | 90 ± 5 |
| Needle T(° C.) | 70 ± 5 | 70 ± 5 | 70 ± 5 |
| Needle Size (I.D.) (mm) | 0.31 | 0.6 | 0.6 |
| High Voltage (Kv) | 15 | 15 | 20 |
| Feed Rate (μl/min) | 10 | 10 | 10 |
| Distance (cm) | 10 | 10 | 10 |

TABLE 2

The electrospinning conditions of PLA 4042D (High Mw).

| | PLA/DMF Concentration (Mw = 211,332) | | | | | |
|---|---|---|---|---|---|---|
| | 22 wt % | | | 25 wt % | | |
| | Cellulose % (w/w PLA) | | | | | |
| | 0 | 1 | 10 | 0 | 1 | 10 |
| Syringe T (° C.) | 70 ± 5 | 70 ± 5 | 70 ± 5 | 70 ± 5 | 80 ± 5 | 80 ± 5 |
| Needle T (° C.) | 70 ± 5 | 70 ± 5 | 70 ± 5 | 70 ± 5 | 70 ± 5 | 70 ± 5 |
| Needle Size (I.D.) (mm) | 0.6 | 0.6 | 0.6 | 0.31 | 0.6 | 0.6 |
| High Voltage (Kv) | 15 | 15 | 15 | 15 | 15 | 20 |
| Feed Rate (μl/min) | 10 | 10 | 10 | 10 | 20 | 20 |
| Ground Distance (cm) | 10 | 10 | 10 | 10 | 10 | 10 |

The morphology of the PLA/cellulose nanocomposites fibers electrospun from PLA/DMF solutions with different cellulose nanofibril contents was observed. For the 22%-L suspensions, as the cellulose nanofibril contents increased, big agglomerates were found on the surface of the electrospun non-woven fabrics. For the 25%-H suspensions, the average fiber diameter of the electrospun nanocomposite fibers was increased compared to the 22%-L system.

The PLA/cellulose nanocomposite fibers electrospun from 22%-L suspensions had a smaller average fiber diameter than the 25%-H suspension system. But the nanocomposite fibers electrospun from 25%-H suspensions had more uniform fiber morphology. The PLA/cellulose nanocomposite fibers electrospun from 22%-H had a smaller average fiber diameter with respect to fibers electrospun from the 25%-H suspensions, while they had a relatively more uniform fibers than fibers electrospun 22%-L suspensions. Therefore, 22%-H system was the optimal condition. All the nanocomposite fibers for the following characterization were electrospun from the 22%-H suspensions. The incorporation of cellulose nanofibrils into the electrospun PLA nanofibers decreased the average fiber diameter under the same processing conditions. Zhou et al. (H. Zhou, K. W. K., E. P. Giannelis, Y. L. Joo, Chapter 16. Nanofibers from Poly(L-Lactic) Acid Nanocomposites: Effects of Nanoclay on Molecular Structures. Polymeric Nanofibers, ACS Symposium Series Book, ed. D. H. Reneker and H. Fong. Vol. 918. 2006, Washington, D.C.: American Chemical Society. 217-230) reported the same phenomena that the addition of nanoclay to PLA decreased fiber diameter. One possible reason is that the incorporation of cellulose nanofibrils affected the charge density of suspensions.

The presence of cellulose nanofibrils on the surface of the electrospun nanocomposite fibers were confirmed by transmission electron microscopy (TEM) and surface elemental analysis.

Surface Composition

The surface elemental composition of pure electrospun PLA nanofibers (control) and the PLA/cellulose nanocomposite fibers was evaluated from information in the $C_{1s}$ regions of the spectra. Peaks from segments between 278 eV and 296 eV were found. Curve-fitting analysis (data not shown) evidenced the presence of five peaks centered at 285.0 eV (C—C/C—H), 287.1 eV (C—O), 288.0 eV (O—C—O), 289.1 eV (O—C=O), and 292.3 eV (R—O—C=O), respectively. For pure electrospun PLA fibers, the binding energy ratio of C—O to C—C/C—H is 0.37, while for PLA/cellulose nanocomposite fibers, the ratio is 3.38. The binding energy of O—C—O for pure PLA is zero, while for PLA/cellulose nanocomposite fibers, it is 31.1 eV. The elemental composition data for various binding energies confirmed the presence of cellulose nanofibrils at the surface of PLA fibers.

Water Contact Angle

Wetting is the interaction between a liquid and a solid and is most often described by resting a drop of liquid on a smooth surface. Wettability is commonly measure by contact angle. Considered a liquid drop on a solid surface, if the liquid is very strongly attracted to the solid surface (for example water on a strongly hydrophilic solid) the droplet will completely spread out on the solid surface and the contact angle will be close to 0°. Less strongly hydrophilic solids will have a contact angle up to 90°. On many highly hydrophilic surfaces, water droplets will exhibit contact angles of 0° to 30°. If the solid surface is hydrophobic, the contact angle will be larger than 90°. On highly hydrophobic surfaces, water droplets simply rest on the surface, without actually wetting to any significant extent (Degennes, P. G., Wetting—Statics and Dynamics. Reviews of Modern Physics, 1985. 57(3): p. 827-863).

The water contact angle of the electrospun non-woven fabrics is shown in Table 3.

TABLE 3

Water contact angle (°) of electrospun PLA/cellulose non-woven fabrics using the water drop method.

| | Water Contact Angle (°) |
|---|---|
| 0% cellulose PLA | 128 ± 2 |
| 1% cellulose PLA | 127 ± 2 |
| 10% cellulose PLA | 115 ± 3 |

As the cellulose nanofibril content increased, the water contact angle of the electrospun non-woven fabrics decreased. The lower the water contact angle, the higher the hydrophilicity. Therefore, the water contact angle confirmed the increase hydrophilicity of the electrospun non-woven fabrics. The improvement of hydrophilicity of the electrospun PLA/cellulose non-woven fabrics is also shown in FIG. 1. FIG. 1 shows the water absorption of the electrospun PLA/cellulose non-woven fabrics with different cellulose nanofibril content as a function of time.

The electrospun PLA/cellulose non-woven fabrics containing 10 wt % cellulose nanofibrils absorbed more water than PLA containing 0% and 1 wt % cellulose nanofibrils. The electrospun non-woven fabrics had typical wicking behavior, with initial rapid absorbance followed by slower absorbance which is in agreement with the earlier reported results (Xiang, C. H., et al., Selective chemical absorbance in electrospun nonwovens. Journal of Applied Polymer Science, 2007. 106(4): p. 2363-2370).The incorporation of 1 wt % cellulose nanofibrils did not change the hydrophilicity of the electrospun non-woven fabrics significantly. But there is an obvious improvement of hydrophilicity as 10 wt % cellulose nanofibrils added into the electrospun PLA/cellulose nanocomposite. Nanocomposite fibers containing 10% cellulose nanofibrils were able to absorb three times of water relative to fiber weight, which is about 30% water absorbance of the 100% commercial cotton woven fabrics (Xiang, C. H., et al., Selective chemical absorbance in electrospun nonwovens. Journal of Applied Polymer Science, 2007. 106(4): p. 2363-2370).

Thermal Properties of Electrospun Nanocomposite Fibers

PLA fibers electrospun from solutions usually exhibit a cold crystallization peak through DSC analysis (Zhou, H. J., T. B. Green, and Y. L. Joo, The thermal effects on electrospinning of polylactic acid melts. Polymer, 2006. 47(21): p. 7497-7505). DSC thermographs were obtained for the electrospun nanocomposite fibers with varying cellulose nanofibril contents (data not shown). For all the nanocomposite fibers, a cold crystallization peak around 100° C. is observed. Both the crystallization temperature corresponding to the peak of the crystallization exotherm and the temperature associated with the beginning of the crystallization process decreased as the cellulose nanofibril content increased, which indicated that the cellulose nanofibrils acted as nucleating agents for the PLA crystallization. No significant influence of the cellulose nanofibril content on Tg is reported and its value is around 58° C.

The degree of crystallinity and the temperature of major peaks from DSC thermographs of various nanocomposite fibers are summarized in Table 4.

TABLE 4

Summary of DSC curves for different PLA/cellulose nanocomposite fibers.

| Cellulose Content (wt %) | Tg (° C.) | Tc (° C.) | Tm (° C.) | ΔHm (J/g) | $\chi_c$(%) | $\chi_p$(%) |
|---|---|---|---|---|---|---|
| 0 | 58.2 | 90.7 | 149.6 | 5.9 | 6.0 | 6.0 |
| 1 | 58.6 | 83.8 | 150.2 | 18.8 | 20.0 | 20.0 |
| 10 | 58.7 | 75.7 | 151.4 | 17.3 | 19.0 | 21.0 |

$\chi_c$ corresponds to the apparent degree of crystallinity of the electrospun nanocomposite fibers calculated from the enthalpy of fusion per gram of composite fiber, whereas $\chi_p$ was obtained from the heat of fusion per gram of PLA in the nanocomposite fibers. The apparent degree of crystallinity was calculated based on the following equation:

$$\chi_c = \frac{\Delta H_f - \Delta H_c}{\Delta H_f^0} \times 100\% \qquad (1)$$

where $\Delta H_f$ is the heat of fusion, $\Delta H_c$ is the heat of cold crystallization and $\Delta H_f^o$ is the heat of fusion for 100% crystalline PLA, 93 J/g (Migliaresi, C., et al., Dynamic Mechanical And calorimetric Analysis Of Compression-Molded Plla Of Different Molecular-Weights—Effect Of Thermal Treatments. Journal Of Applied Polymer Science, 1991. 43(1): p. 83-95).

$$\chi_p = \chi_c / W \qquad (2)$$

where w is the weight fraction of PLA in the nanocomposite fibers. Equation (2) above normalizes for the amount of matrix material (PLA) versus cellulose (incorporated material) in the fiber, i.e., not including cellulose in the calculation.

According to Table 4, the incorporation of cellulose nanofibrils to PLA increased the crystallinity of the electrospun nanocomposite fibers. Cellulose nanofibrils acted as nucleating agents for the crystallization of PLA.

Wide Angle X-Ray Diffraction of the Electrospun Non-Woven Fabrics

Wide angle X-ray diffraction studies were carried out for the electrospun PLA/cellulose nanocomposite fibers (data not shown). The electrospun PLA/cellulose nanocomposite fibers clearly exhibit a strong peak at 2θ equal to 16.7° and a small peak at 2θ equal to 19°, while only a broad peak is observed for the pure electrospun PLA non-woven fabrics. Electropinning is a process of quick stretching driven by a high electric field. The rapid solidification and short residence time during electrospinning may be attributed to the low crystallinity of the pure electrospun PLA fibers. Both the WXAD data and the DSC results show the low crystallinity of the pure electrospun PLA fibers and the increase of crystallinity by the addition of cellulose nanofibrils into PLA nanocomposite fibers.

Tensile Testing

Table 5 shows the mechanical properties of the electrospun PLA/cellulose non-woven fabrics. The addition of cellulose increased the Young's modulus, maximum tensile stress, and the tensile stress at break of the electrospun non-woven fabrics.

TABLE 5

Mechanical properties of the electrospun PLA/cellulose non-woven fabrics.

| | Cellulose Concentration wt % (on the weight of PLA) | | |
|---|---|---|---|
| | 0% | 1% | 10% |
| Modulus (Young's) (MPa) | 24.6 ± 10.9 | 33.7 ± 7.7 | 31.7 ± 8.6 |
| Maximum Tensile Stress (MPa) | 4.3 ± 0.6 | 5.6 ± 0.6 | 4.6 ± 0.7 |
| Tensile Stress at Break (Cursor) (MPa) | 3.6 ± 0.9 | 4.8 ± 0.6 | 3.9 ± 0.6 |
| Tensile Strain at Break (Cursor) (%) | 65.6 ± 10.2 | 64.7 ± 6.2 | 58.2 ± 7.6 |
| Tensile Strain at Maximum Tensile Stress (%) | 59.6 ± 11.5 | 59.5 ± 6.3 | 54.1 ± 7.4 |

The mechanical properties were also normalized by the weight of each specimen (Table 6):

TABLE 6

Normalized mechanical properties of the electrospun PLA/cellulose non-woven fabrics.

| | Cellulose Concentration wt % (on the weight of PLA) | | |
|---|---|---|---|
| | 0% | 1% | 10% |
| Modulus (Automatic) (Mpa) | 8.2 ± 3.3 | 11.9 ± 2.7 | 10.5 ± 3.4 |
| Maximum Tensile Stress (MPa) | 1.4 ± 0.2 | 2.0 ± 0.2 | 1.5 ± 0.2 |
| Tensile Stress at Break (Cursor) (MPa) | 1.2 ± 0.3 | 1.7 ± 0.2 | 1.3 ± 0.2 |
| Tensile Strain at Break (Cursor) (%) | 22.3 ± 4.9 | 22.9 ± 3.4 | 19.4 ± 5.4 |
| Tensile Strain at Maximum Tensile Stress (%) | 20.3 ± 4.9 | 21.1 ± 3.4 | 18.0 ± 5.3 |

The Young's modulus, maximum tensile stress, and the tensile stress at break of the PLA/cellulose non-woven fabrics containing 1 wt % cellulose nanofibrils improved 37%, 31%, 34% respectively compared to the pure electrospun PLA non-woven fabrics, and those containing 10 wt % cellulose nanofibrils improved 29%, 7%, and 9% respectively than those of the pure PLA electrospun non-woven fabrics.

On one hand, not only the electrospun fiber itself, but the interaction between fibers in the electrospun non-woven fabrics contributed to the mechanical properties of the non-woven fabrics. The PLA/cellulose nanocomposite fibers electrospun exhibited finer fiber sizes and provided more contacts between the fibers and thus strong cohesion among fibers. Therefore, the non-woven fabrics formed by PLA/cellulose nanocomposite fibers were stiffer and stronger than the pure electrospun PLA non-woven fabrics. On the other hand, the increase of crystallinity of the electrospun PLA/cellulose nanocomposite fibers contributed to the increase of stiffness and strength of nanocomposite fibers.

The elongation of the electrospun PLA/cellulose non-woven fabrics containing 1 wt % cellulose did not change significantly compared to that of the pure PLA non-woven fabrics. While the elongation of those containing 10 wt % cellulose content decreased about 10% compared to that of the pure PLA non-woven fabrics. The crystallinity of the electrospun non-woven fabrics can explain this. Nanocomposite fibers containing 1 wt % cellulose nanofibrils had perfect crystal matrix. While as the cellulose nanofibril content increased to 10%, there were too many nucleating agents for PLA crystallization, defects occurred, which caused the decrease of the elongation of the nanocomposite fibers.

Conclusion

Cellulose nanofibrils were successfully produced by hydrolysis. PLA/cellulose nanocomposite fibers were successfully produced by elevated temperature electrospinning. The electrospinning conditions were optimized by PLA molecular weight, polymer concentration, syringe temperature, needle size and high voltage. Average fiber diameter was not significantly affected by the addition of cellulose nanofibrils. Surface elemental composition analysis confirmed the presence of cellulose nanofibrils at the surface of PLA fibers. The strength of the electrospun non-woven fabrics was improved by the incorporation of cellulose nanofibrils into PLA. Elongation of electrospun non-woven fabrics was decreased by the incorporation of cellulose nanofibrils into PLA. The degree of crystallinity of the electrospun PLA/cellulose nanocomposite fibers was increased by the incorporation of cellulose nanofibrils, which indicated that cellulose nanofibrils acted as nucleating agent of PLA crystallization. As the cellulose nanofibril content increased, the electrospun PLA/cellulose nanocomposite fibers became increasingly hydrophilic.

6.2 Example 2: Hydrolytic Degradation of Nanocomposite Fibers Electrospun from Poly(Lactic Acid)/Cellulose Nanocrystals Summary The influence of cellulose nanocrystals on the hydrolytic degradation of electrospun PLA/cellulose nanocomposite fibers was investigated. As the cellulose nanocrystal content increased, the electrospun non-woven fabrics became increasingly hydrophilic. Hydrolytic degradation of the nanocomposite fibers was conducted in phosphate buffer solution (PBS, pH 7.4, 37° C.) with constant shaking. The electrospun PLA/cellulose nanocomposite fibers became rougher and swelled during hydrolytic degradation. The apparent degradation rates based on the molecular weight of PLA were calculated to be 0.0068, 0.0084, and 0.0128 lgM/week for the electrospun PLA/cellulose nanocomposite fibers spun from PLA solutions containing 0.1%, and 10% cellulose nanocrystals, respectively. A linear relationship between lgM and the degradation time suggests that the hydrolytic degradation of the electrospun PLA/cellulose nanocomposite fibers in PBS occurred via a random chain scission reaction. Polydispersity indices of PLA did not change significantly during hydrolytic degradation. The constant polydispersity indices of PLA further confirmed a random chain scission degradation mechanism. No autocatalytic degradation occurred during the hydrolytic degradation of electrospun PLA/cellulose nanocomposite fibers.

Introduction

This example investigated the influence of cellulose nanocrystals on the hydrolytic degradation of electrospun PLA/cellulose nanocomposite fibers. Cellulose nanocrystals occur naturally in the cell wall of plants and have been shown to increase the crystallinity of PLA when incorporated in PLA/cellulose nanocomposite fibers (Xiang, C. J., Yong L; Frey Margaret W, Nanocomposite Fibers Electrospun from Poly(lactic acid)/Cellulose Nanocrystals. Journal of Biobased Materials and Bioenergy, 2009. 3(2): p. 147-155). The presence of cellulose nanocrystals at the surface of the electrospun PLA fibers was confirmed and the quantity of cellulose available at the surface was enriched compared to the bulk composition. Cellulose nanocrystals acted as nucleation sites during the electrospinning process resulting in increased crystallinity of electrospun PLA nanocomposite fibers influence of cellulose nanocrystal content on the hydrophilicity of the electrospun non-woven fabrics was studied by measuring the water absorption and water contact angle of PLA/cellulose non-woven fabrics. The hydrolytic degradation behaviors of the electrospun PLA/cellulose nanocomposite fibers, spun from solutions containing 0.1%, and 10% suspended cellulose nanocrystals in phosphate buffer solution (PBS pH 7.4) at 37° C. were investigated and the degraded nanocomposite fibers were examined. The morphological changes of the electrospun PLA/cellulose nanocomposite fibers were observed by field emission scanning electron microscopy (Keck SEM). And the molecular weight of PLA from the nanocomposite fibers during hydrolytic degradation was investigated by size exclusive chromatography (SEC).

Materials

Microcrystalline cellulose powder (MCC, extra pure, average particle size 90 μm) was purchased from Acros Organics (Geel, Belgium). Poly(lactic acid) (PLA) (Mw=211,000 Da, Mn=109,000 Da) was supplied by Cargill Dow (Minnetonka, Minn.) and phosphate buffered saline (PBS) (p-5368, pH 7.4) was purchased from Sigma-Aldrich (St. Louis, Mo.). N,N-dimethyl formamide (DMF) was purchased from Mallinckrodt Laboratory Chemicals (Phillipsburg, N.J.). Cellulose nanocrystals were prepared from microcrystalline cellulose by acid hydrolysis (Xiang, C. J., Yong L; Frey Margaret W, Nanocomposite Fibers Electrospun from Poly(lactic acid)/Cellulose Nanocrystals. Journal of Biobased Materials and Bioenergy, 2009. 3(2): p. 147-155). All other reagents were used without further purification.

Methods and Techniques

Elevated Temperature Electrospinning Processing

Polymer suspensions, consisting of PLA and cellulose nanocrystals, were prepared in DMF solvent. The concentration of the final suspension used for electrospinning was 22 wt % PLA in DMF containing cellulose nanocrystals contents of 0%, 1%, and 10% based on the weight of PLA. The suspensions were then electrospun at 70° C. During electrospinning, the polymer suspension was introduced into a 5 mL glass syringe (VWR Scientific, West Chester, Pa.). The syringe was attached with a metal needle (ID=0.60 mm) and put into a shielded heating unit that was pre-heated to 70±5° C. and controlled by a Watlow controller (St. Louis, Mo.). After about 10 minutes thermal equilibration, electrospinning was started at 15 kV which was supplied by a high voltage supply (Gamma High Voltage Research Inc., FL) and at 10 μL/min feed rate driven by a programmable syringe micropump (Harvard Apparatus, MA). A rotating aluminum plate (Diameter=20 cm) covered with aluminum foil was used to collect nanocomposite fibers at a 10 cm distance away from the needle tip. Each sample was collected for five hours.

Water Contact Angle Measurements

The contact angle of water on the electrospun PLA/cellulose non-woven fabrics was measured by the sessile drop method (Owens, D. K. and R. C. Wendt, Estimation of Surface Free Energy of Polymers. Journal of Applied Polymer Science, 1969. 13(8): p. 1741-&) using a contact angle analyzer (Imass, Model CAA2). Smooth surface (spin-coated) films were cast from PLA/DMF solution with 0%, 1% and 10% cellulose nanocrystals suspended with a spin processor (Model Ws-650sx—6NPP/A1/AR1Laurell Technologies Corporation) at a speed of 500 rpm. The contact angle of water on the spin-coated films was measured with the same method as the electrospun non-woven fabrics. The final result for each sample was obtained by averaging at least ten separate measurements.

The hydrophilicity of the electrospun PLA/cellulose nanocomposite fibers was studied by measuring the water absorption of the electrospun non-woven fabrics. The water absorption was investigated by measuring the weight change with time when the electrospun PLA/cellulose non-woven fabrics were in contact with water using a Sigma 700 (KSV Instruments) wettability apparatus. The electrospun non-woven fabrics cut into 0.5 cm×3 cm rectangles were attached to small copper-wire hooks with an adhesive and allowed to dry at room temperature for at least 12 hours. Four specimens were tested for each sample. The pore size of the electrospun non-woven fabrics cut into two-inch-diameter circles was measured with an 1100-AEHXL capillary flow porometer (Porous Media, Inc.). Three specimens for each sample were measured.

Hydrolytic Degradation of Electrospun Nanocomposite Fibers

The hydrolytic degradation of the electrospun PLA/cellulose nanocomposite fibers was conducted following the method by Tarvainen et al. (Tarvainen, T., Degradaton of and drug release from a novel 2,2-bis(2-oxazoline) linked poly(lactic acid) polymer. Journal of Controlled Release, 2002. 81: p. 251-261). The electrospun non-woven fabrics (30×30 mm$^2$) were immersed in 10 ml PBS (pH 7.4) in closed bottles and shaken constantly (100 rpm) in a water bath at 37° C. The hydrolytic degradation procedure was set to 15 weeks. One specimen was withdrawn at each week (per week). The degraded electrospun PLA/cellulose nanocomposite fibers were vacuum dried at 25° C. for a week before being subjected to various analyses.

Microscopy

The morphology of the electrospun PLA/cellulose nanocomposite fibers during hydrolytic degradation was observed with a field emission scanning electron microscope (FESEM, LEO 1550). The fibers were sputter-coated with a 2-3 nm layer of gold and palladium for imaging using a Desk II cold sputter/etch unit (Edwards S150 Sputter Coater). The fiber diameters were determined using image processing and analysis in Java software (ImageJ). The structural study of PLA nanocomposite fibers spun from solutions containing 10% cellulose nanocrystals was performed through transition transmission electron microscopy (TEM, Technai T12). In the TEM study, to obtain a sectional image, the electrospun fibers were microtomed at room temperature using a diamond knife; to get whole fiber morphology, the nanocomposite fibers were directly collected on the TEM grids for about 2 seconds. The TEM grids with nanocomposite fibers were stained with ruthenium tetraoxide (RuO$_4$) vapors overnight before TEM observation to improve contrast between PLA and cellulose nanocrystals. TEM images of the fibers were taken using Technai T12 at an accelerating voltage of 120 kV.

Size Exclusion Chromatography (SEC)

The molecular weight of PLA samples (as-received samples and hydrolytically degraded PLA) was determined by size exclusion chromatography (SEC) (a Waters 486 UV detector and a Waters 2410 differential refractive index detector, Waters Corporation), using polystyrene standards for calibration and tetrahydrofuran (THF) as the carrier solvent at 40° C. with a flow rate of 0.5 ml/min. For SEC measurements, the electrospun PLA/cellulose nanocomposite fibers were dissolved in THF. Cellulose nanocrystals were removed by filtration (pore size: 0.45 μm, Millipore) prior to the molecular weight measurements.

Thermogravimetric Analysis (TGA)

Thermogravimetric measurements were carried out with a thermogravimetric analyzer (TGA 2050, TA Instruments Inc.). The temperature range was 25° C. to 600° C. at 10° C./min ramp under nitrogen flow.

Results and Discussion

Figure 2:
FIG. 2. TEM images of the electrospun PLA/cellulose nanocomposite fibers spun from solutions containing 10% cellulose nanocrystals. (a) Whole fiber morphology. (b) Sectional structure of the nanocomposite fiber. See Section 6.2 for details.
Figure 2:
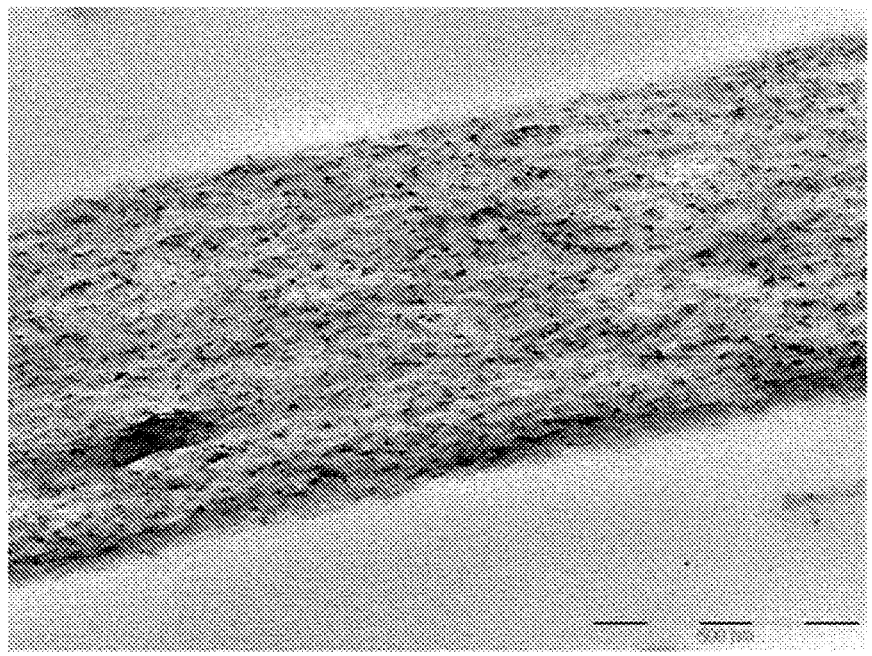

Distribution of Cellulose Nanocrystals in the Electrospun PLA/Cellulose Nanocomposite Fibers The morphology of the electrospun PLA nanocomposite fibers spun from solutions containing 10% cellulose nanocrystals is shown in FIG. 2(a). The distribution of cellulose nanocrystals within the PLA/cellulose nanocomposite is shown in FIG. 2(b). Darker portions in both photomicrographs are identified as cellulose nanocrystals which have been stained with RuO$_4$ for contrast. Cellulose nanocrystals appear to be well dispersed within the PLA fibers, however, the apparent size of cellulose nanocrystals at the surface and in the interior of the fibers is much shorter than the 100 nm length measured for the original nanocrystals (Xiang, C. J., Yong L; Frey Margaret W, Nanocomposite Fibers Electrospun from Poly(lactic acid)/Cellulose Nanocrystals. Journal of Biobased Materials and Bioenergy, 2009. 3(2): p. 147-155). Although cellulose nanocrystals are reported to have high modulus (Noorani, S., J. Simonsen, and S. Atre, Nano-enabled microtechnology: polysulfone nanocomposites incorporating cellulose nanocrystals. Cellulose, 2007. 14(6): p. 577-584), flexibility of these crystals is low. During the course of the stretching and whipping processes occurring during electrospinning, the cellulose nanocrystals appear to have fractured into shorter lengths. For the purposes of this study, the quantity of cellulose in the fibers is more critical than the fiber length. Incorporation of cellulose has been confirmed earlier via X-ray photoelectron spectroscopy (Xiang, C. J., Yong L; Frey Margaret W, Nanocomposite Fibers Electrospun from Poly(lactic acid)/Cellulose Nanocrystals. Journal of Biobased Materials and Bioenergy, 2009. 3(2): p. 147-155) and was further confirmed by TGA below.

Thermogravimetric Analysis of Electrospun PLA/Cellulose Nanocomposite Fiber

TGA measurements were obtained of nanocomposite fibers electrospun from PLA spun from solutions containing 0, 1%, and 10% cellulose nanocrystals (data not shown). The lack of mass loss at temperatures below 200° C. confirms that samples were well dried. At 1% cellulose nanocrystal loadings, no obvious degradation was observed at about 250° C. The 10% cellulose nanocrystal loadings showed a bimodal distribution with the expected ~250° C. cellulose nanocrystal degradation step and the ~350° C. PLA step occurring relatively independently at degradation temperatures expected for the pure components. Cellulose nanocrystals degraded at a relatively low temperature for pure cellulose material due to residual acidity from the acid hydrolysis nanocrystal preparation method (Roman, M. and W. T. Winter, Effect of sulfate groups from sulfuric acid hydrolysis on the thermal degradation behavior of bacterial cellulose. Biomacromolecules, 2004. 5(5): p. 1671-1677; Li, R. J., et al., Cellulose whiskers extracted from mulberry: A novel biomass production. Carbohydrate Polymers, 2009. 76(1): p. 94-99). Additionally, cellulose nanocrystals have been shown to leave approximately 30% of their mass as ash after hydrolysis. Based on the weight loss percentage from each degradation step and the mass after incineration relative to the original nanocomposite fiber mass, the 1% and 10% cellulose nanocrystals incorporated into the electrospun PLA nanocomposite fibers were confirmed.

Hydrophobicity/Hydrophilicity of Electrospun Non-Woven Fabrics

A nanocomposite fiber combining hydrophobic (PLA) and hydrophilic (cellulose nanocrystals) components is expected to have wetting and water absorbance (wicking) behavior intermittent between the two components. Wettability is commonly measure by contact angle. A water drop on a solid surface will completely spread out on a hydrophilic surface and the contact angle will be close to 0°. Less strongly hydrophilic solids will have a contact angle of up to 90°. If the solid surface is hydrophobic, the contact angle will be larger than 90° (Degennes, P. G., Wetting—Statics and Dynamics. Reviews of Modern Physics, 1985. 57(3): p. 827-863). The surface in these experiments is a non-woven mesh of multiple fibers which is both rough and porous. In the case of a hydrophobic sample, surface roughness is expected to increase the observed contact angle (Lee, H. J., Michielsen, S., Preparation of a superhydrophobic rough surface. Journal of Polymer Science Part B—Polymer Physics, 2007. 45(3): p. 253-261; Michielsen, S. and H. J. Lee, Design of a superhydrophobic surface using woven structures. Langmuir, 2007. 23(11): p. 6004-6010). A hydrophilic material will rapidly absorb the applied droplet.

Generally, surface chemistry and the surface roughness affect contact angle (Nakajima, A., Hashimoto, K., Watanabe, T., Recent studies on super-hydrophobic films. Monatshefte Fur Chemie, 2001. 132(1): p. 31-41; Quéré, D., Rough ideas on wetting. Physica A: Statistical Mechanics and its Applications, 2002. 313(1-2): p. 32-46). Namely, the contact angle increases as the surface roughness increases (Ma, M. L., Mao, Y., Gupta, M., Gleason, K. K., Rutledge, G. C., Superhydrophobic fabrics produced by electrospinning and chemical vapor deposition. Macromolecules, 2005. 38(23): p. 9742-9748) and non-woven fabrics comprised of small fibers are more hydrophobic than films prepared from the same polymer. Table 7 shows the initial contact angle of water on the electrospun non-woven fabrics and the spin-coated films. The initial contact angle is defined as the contact angle measured within one minute of placement of the drop on the substrate. As the cellulose nanocrystal content increased, the water contact angle of the electrospun non-woven fabrics and spin coated films decreased. The addition of 1% w/w cellulose did not significantly decrease the contact angle of water on the surface of the non-woven fabrics or spin coated films. When cellulose nanocrystal loading was increased from 0 to 10% w/w, the water contact angle was decreased by more than 10°. The decrease of the initial contact angle of the electrospun non-woven fabrics and spin coated films indicated that the incorporation of cellulose nanocrystals improved the hydrophilicity of PLA.

TABLE 7

The initial water contact angle of electrospun PLA/cellulose non-woven fabrics and PLA/cellulose spin-coated films.

| Water Contact Angle (°) | ES Non-wovens | Spin-Coated Film |
| --- | --- | --- |
| 0% cellulose PLA | 128 ± 2 | 91 ± 2 |
| 1% cellulose PLA | 127 ± 2 | 91 ± 2 |
| 10% cellulose PLA | 115 ± 3 | 77 ± 1 |

The decrease in hydrophobicity of the electrospun PLA/cellulose non-woven fabrics was also measured by rate of water absorption. Again the behavior of the sample spun from solutions containing 1% w/w cellulose nanocrystals was not significantly different from the neat PLA sample. The electrospun PLA/cellulose non-woven fabrics containing 10% w/w cellulose nanocrystals absorbed six times more water than PLA containing 0% and 1% w/w cellulose nanocrystals. The electrospun non-woven fabrics had typical wicking behavior, with initial rapid absorbance followed by slower absorbance (Xiang, C. J., Yong L; Frey Margaret W, Nanocomposite Fibers Electrospun from Poly(lactic acid)/Cellulose Nanocrystals. Journal of Biobased Materials and Bioenergy, 2009. 3(2): p. 147-155).

Overall, the incorporation of 1% w/w cellulose nanocrystals did not decrease the hydrophobicity of the electrospun non-woven fabrics significantly. There was an obvious decrease of hydrophobicity, however, when 10% w/w cellulose nanocrystals were added into the electrospun PLA/cellulose nanocomposite. Nanocomposite fibers spun from solutions containing 10% cellulose nanocrystals absorbed three times the initial sample weight of water. For comparison, 100% cellulose electrospun fabrics have been reported to absorb more than 10 times the initial sample weight of water (Xiang, C. H., Frey, M. W., Taylor, A. G., Rebovich, M. E., Selective chemical absorbance in electrospun non-wovens. Journal of Applied Polymer Science, 2007. 106(4): p. 2363-2370).

During absorption processes, pores act as capillaries, pulling liquid into the fabric via capillary action. The capillary action can be described in the following equation (Miller, B., Experimental Aspects of Fiber Wetting and Liquid Movement Between Fibers, in Absorbency, P. K. Chatterjee, Editor. 1985, Elsevier Science Publishing Company Inc.: New York. p. 121-147):

$$H = 2T \cos \theta / \rho g r \qquad (4)$$

where h is the height (m), T is the surface tension ($J/m^2$ or N/m), $\theta$ is the contact angle, $\rho$ is the density of the liquid ($kg/m^3$), g is the acceleration due to gravity ($m/s^2$), and r is the radius of the tube (m). The pore size corresponds to the radius of the tube, and the compatibility between the liquid and the fiber is expressed as $\cos \theta$. When the liquid wets the fiber surface, $\cos \theta$ will approach 1. A combination of a compatible liquid and a small pore radius is expected to result in increased liquid absorbance. The mean pore size was determined for the electrospun non-woven fabrics of PLA containing 0%, 1%, and 10% cellulose nanocrystals. At a 0.05 significant level, there is no difference in the mean pore size among the non-woven fabrics containing different proportions of cellulose nanocrystals. Hence, there is no significant difference in the effective pore radius (r). Based on equation (4), $\cos \theta$ is the parameter which determines the liquid absorption. The higher the $\cos \theta$, the higher the absorption. Our results showed that the electrospun non-woven fabrics of PLA containing 10% cellulose nanocrystals had the highest $\cos \theta$, and it also had the highest water absorption. The water absorption results are consistent with the predicted results. Based on the contact angle and water absorption results, incorporation of cellulose nanocrystals is expected to increase interaction between water and the PLA/cellulose nanocomposite fibers during the hydrolytic degradation processes.

Figure 3:
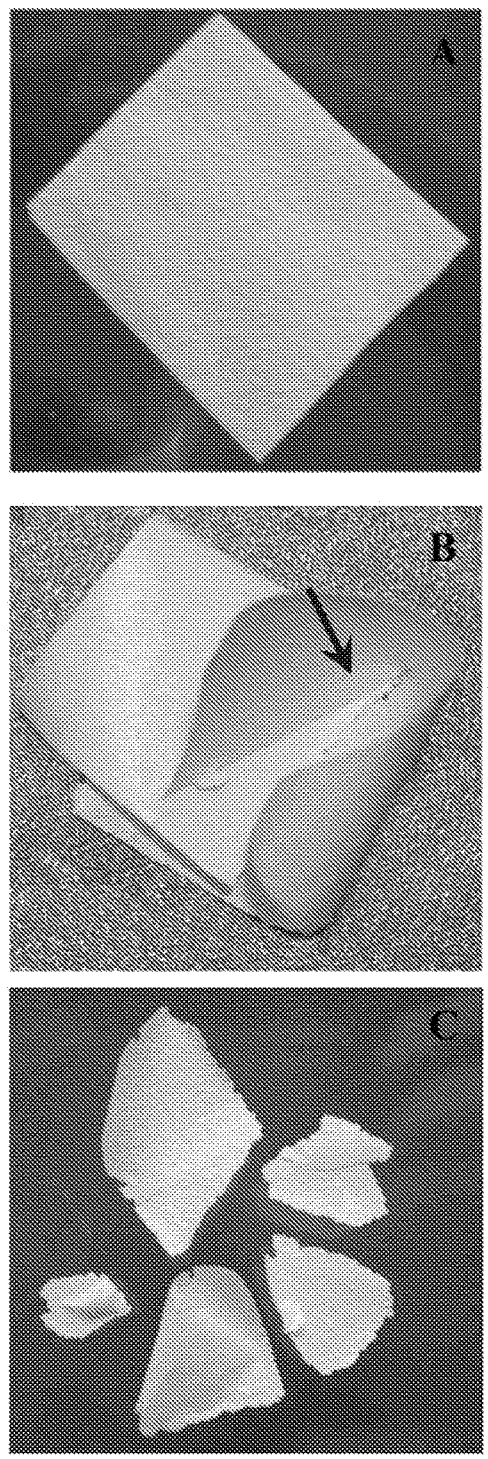
FIG. 3. Digital camera images of the electrospun PLA/cellulose nanocomposite fibers spun from solutions containing 10% cellulose nanocrystals during hydrolytic degradation. (A) Original electrospun non-woven fabrics; (B) degraded for 8 weeks; (C) degraded for 15 weeks. See Section 6.2 for details.

Morphologies of the Electrospun PLA/Cellulose Nanocomposite Fibers During Hydrolytic Degradation Over the course of the hydrolytic degradation study the bulk morphology of the electrospun PLA non-woven fabrics deteriorates. Digital camera images of the electrospun non-woven fabrics of PLA/cellulose nanocomposite fibers spun from solutions containing 10% cellulose nanocrystals clearly exhibit the effects of degradation (FIG. 3). The original sample was a single piece of non-woven fabric (FIG. 3A). After eight weeks of hydrolytic degradation, the non-woven fabric was broken. There is an obvious embrittlement and cracking on the non-woven fabric (FIG. 3B). The non-woven fabric fell into parts after fifteen weeks of hydrolytic degradation (FIG. 3C). Embrittlement, cracking and general loss of physical properties is frequently associated with degradation of polymeric materials (Su Ming Li, H. G., M. Vert, Structure-property relationships in the case of the degradation of massive aliphatic poly-(α-hydroxy acids) in aqueous media, Part 1: Poly(DL-lactic acid). Journal of Materials Science: Materials in Medicine, 1990. 1(3): p. 123-130) as the polymer molecular weight decreases.

Figure 4:
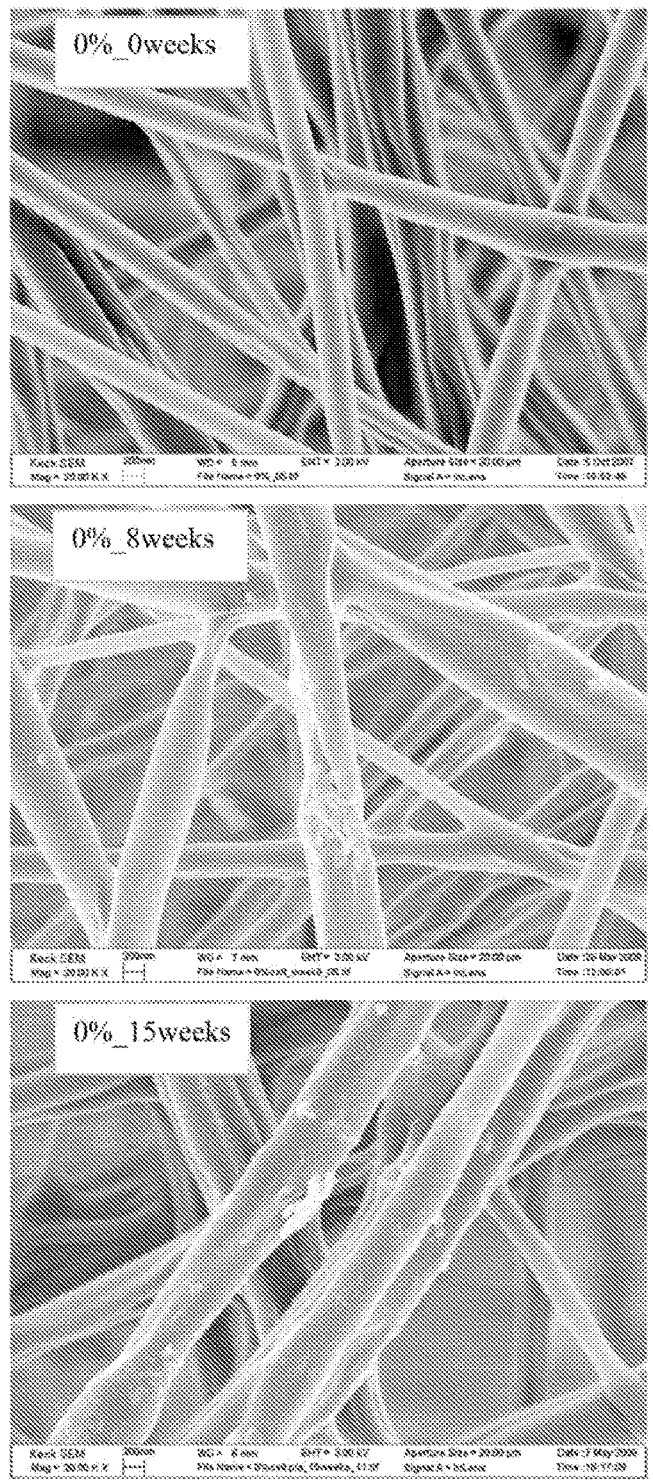
FIG. 4. FESEM images of electrospun PLA nanocomposite fibers spun from solutions containing 0% cellulose nanocrystals during hydrolytic degradation. See Section 6.2 for details.
Figure 5:
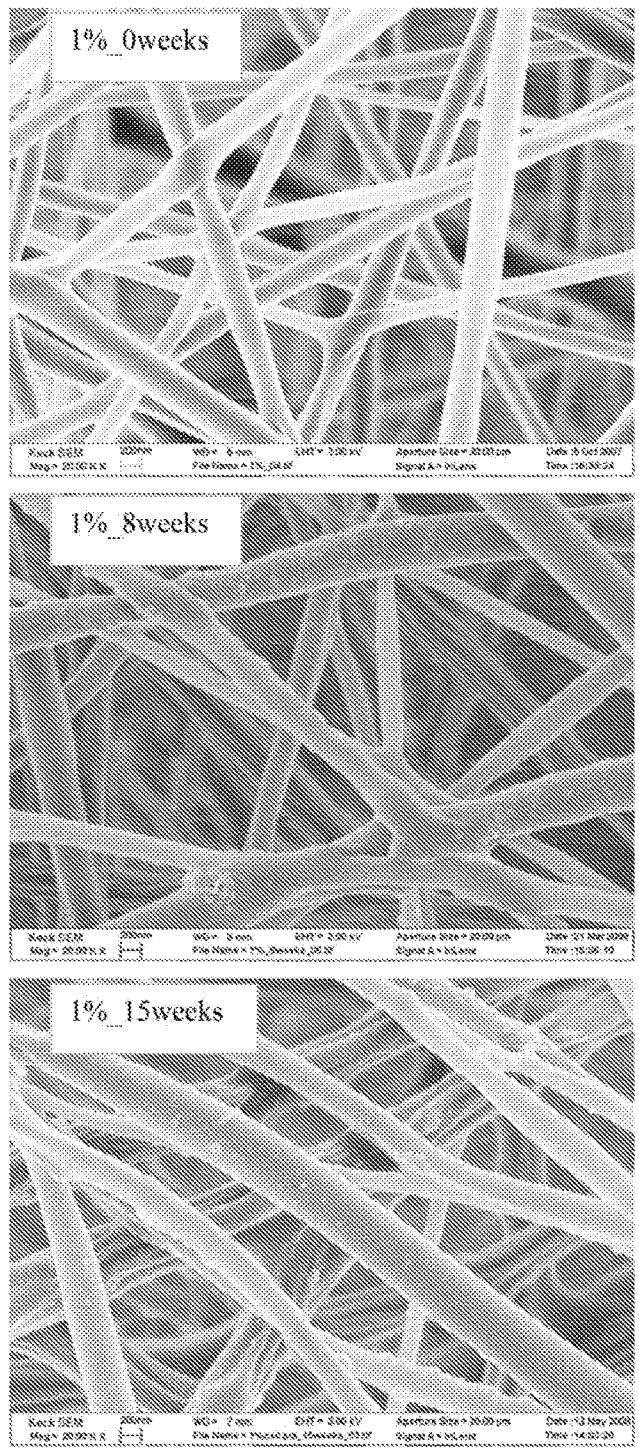
FIG. 5. FESEM images of electrospun PLA/cellulose nanocomposite fibers spun from solutions containing 1% cellulose nanocrystals during hydrolytic degradation. See Section 6.2 for details.
Figure 6:
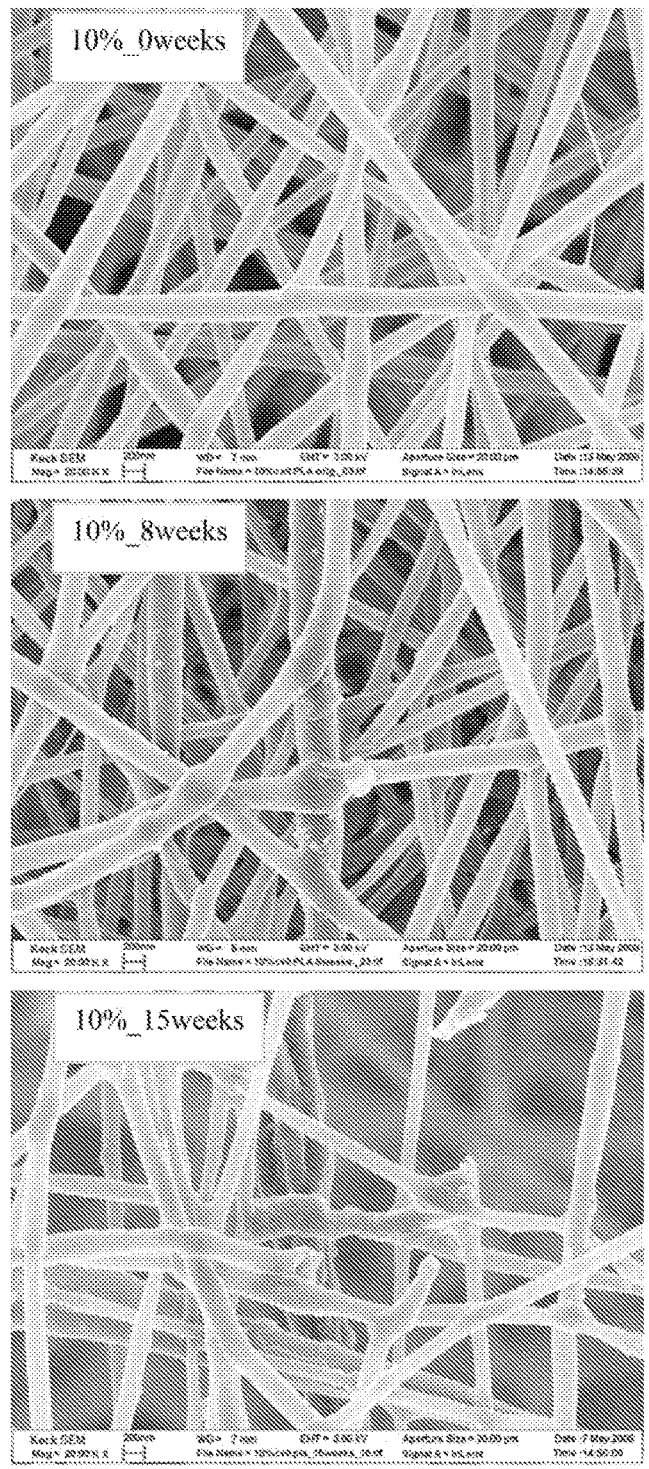
FIG. 6. FESEM images of electrospun PLA/cellulose nanocomposite fibers spun from solutions containing 10% cellulose nanocrystals during hydrolytic degradation. See Section 6.2 for details.

FESEM observations (FIGS. 4-6) revealed that original electrospun PLA/cellulose nanocomposite fibers exhibited smooth surfaces. After eight weeks of hydrolytic degradation, the electrospun PLA/cellulose nanocomposite fibers spun from solutions containing 0%, 1%, and 10% cellulose nanocrystals were still in fiber shape. However, small cracks and white agglomerates were observed at the surface of the fibers. After fifteen weeks of hydrolytic degradation, broken nanocomposite fibers (FIG. 6, 10%_15 weeks) were found in the non-woven fabrics of PLA/cellulose nanocomposite fibers spun from solutions containing 10% cellulose nanocrystals. The morphological changes were greater in PLA/cellulose nanocomposite fibers spun from solutions containing 10% cellulose nanocrystals indicating a greater degree of hydrolytic degradation than apparent for the nanocomposite fibers spun from solutions containing 0% and 1% cellulose nanocrystals. The average fiber diameter of the electrospun nanocomposite fibers increased during the hydrolytic degradation and the fibers swelled. Fiber swelling, however, occurred in all samples regardless of cellulose nanocrystal content.

Figure 7:
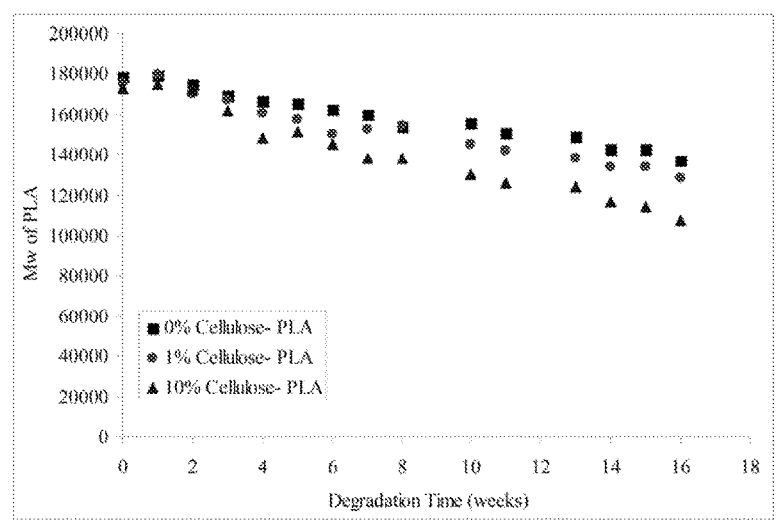
FIG. 7. Molecular weight changes of poly(lactic acid) as a function of degradation time in phosphate buffer solution (pH 7.4) at 37° C. See Section 6.2 for details.

Molecular Weight Change of PLA in the Electrospun Nanocomposite Fibers During Hydrolytic Degradation FIG. 7 shows the changes of molecular weight of PLA from the electrospun PLA/cellulose nanocomposite fibers during hydrolytic degradation. The molecular weight decreased exponentially over the degradation process, indicating almost simultaneous degradation on the surface and in the interior of the material. This is a typical characteristic of bulk degradation mechanism of polymers (Sykes, P., A Guidebook to Mechanism in Organic Chemistry. 5th ed. 1981: London; New York: Longman). The slopes of the curves are considered as the hydrolytic degradation rate. PLA/cellulose nanocomposite fibers spun from solutions containing 10% cellulose nanocrystals degraded faster than the nanocomposite fibers spun from solutions containing 0 and 1% cellulose nanocrystals degraded. Huang et al. (Huang, Y. Y., et al., Degradation of porous poly(D,L-lactic-co-glycolic acid) films based on water diffusion. Journal of Biomedical Materials Research Part A, 2007. 80A(4): p. 909-915) reported that the in vitro degradation of PLA started with the absorption of water, followed by the hydrolytic cleavage of ester bonds, which generates chain fragments with acidic end groups. The absorption of water is the first step and hydrolytic cleavage of ester bonds is second step in polymer degradation. Hydrolytic degradation results follow the same pattern as the contact angle and moisture absorbance results above. Incorporation of 1% wt cellulose did not significantly change the wetting behavior or the degradation behavior of the electrospun PLA/cellulose nanocomposite fibers as compared to the neat PLA fibers. The electrospun PLA/cellulose nanocomposite fibers spun from solutions containing 10 wt % cellulose nanocrystals absorbed more water than nanocomposite fibers spun from solutions containing 0 and 1% cellulose nanocrystals and also degraded at a significantly more rapid rate. Although swelling was observed for all fibers, the addition of cellulose nanocrystals to the electrospun PLA/cellulose nanocomposite fibers accelerated the hydrolytic degradation. If the increased PLA degradation rate is related to residual acidity at the cellulose surface, the well known autocatalytic PLA degradation could be expected for this system. Bimodal profiles of SEC chromatograms of PLA ageing in phosphate buffer evidence the occurrence of autocatalysis (Su Ming Li, H. G., M. Vert, Structure-property relationships in the case of the degradation of massive aliphatic poly-(α-hydroxy acids) in aqueous media, Part 1: Poly(DL-lactic acid). Journal of Materials Science: Materials in Medicine, 1990. 1(3): p. 123-130). Our following monomodal SEC patterns of PLA confirmed that no autocatalysis occurred during hydrolytic degradation of electrospun PLA/cellulose nanocomposite fibers.

There is a linear relationship between lgM and degradation time, which fits Pitt's equation (Pitt, C. G., Jeffcoat, A. R., Zweidinger, R. A., Schindler, A., Sustained Drug Delivery Systems. 1. Permeability of Poly(Epsilon-Caprolactone), Poly(Dl-Lactic Acid), and Their Copolymers. Journal of Biomedical Materials Research, 1979. 13(3): p. 497-507). The linear relationship between LgM and the degradation time suggests that the hydrolytic degradation of the electrospun PLA/cellulose nanocomposite fibers in PBS (pH 7.4) proceeded via a random chain scission reaction. According to the following exponential relationship between molecular weight and degradation time, $$LgM = lgM_0 - Kt \quad (5)$$

the apparent degradation rate, K, can be obtained. The degradation half time, $t_{1/2}$ can further be calculated by equation (6) (Huang, Y. Y., et al., Degradation of porous poly(D,L-lactic-co-glycolic acid) films based on water diffusion. Journal of Biomedical Materials Research Part A, 2007. 80A(4): p. 909-915):

$$t_{1/2} = lg2/K \quad (6)$$

The apparent degradation rates for the electrospun PLA/cellulose nanocomposite fibers without cellulose nanocrystals incorporated in were calculated to be 0.0068 lgM/week ($R^2$=97.77%) based on the weight average molecular weight of PLA, for the electrospun PLA/cellulose nanocomposite fibers spun from solutions containing 1% cellulose nanocrystals were calculated to be 0.0084 lgM/week ($R^2$=96.72%), and for the electrospun PLA/cellulose nanocomposite fibers spun from solutions containing 10% cellulose nanocrystals were calculated to be 0.0128 lgM/week ($R^2$=97.67%). Degradation half times derived from molecular weight of PLA were about 44, 36, and 24 weeks for the electrospun PLA/cellulose nanocomposite fibers spun from solutions containing 0, 1%, and 10% cellulose nanocrystals, respectively. The hydrolytic degradation rate of the electrospun PLA/cellulose nanocomposite fibers spun from solutions containing 10% cellulose nanocrystals was faster than that of nanocomposite fibers spun from solutions containing 0 and 1% cellulose nanocrystals.

The polydispersity indices ($I=M_w/M_n$) of PLA in the electrospun PLA/cellulose nanocomposite fibers were calculated as a function of degradation time in PBS (pH 7.4) at 37° C. The polydispersity indices of PLA did not change significantly during hydrolytic degradation. The molecular weight of PLA decreased with hydrolytic degradation but the polydispersity indices remained nearly unchanged, which suggests a random chain cleavage rather than an unzipping process (Volland, C., M. Wolff, and T. Kissel, The Influence of Terminal Gamma-Sterilization on Captopril Containing Poly(D,L-Lactide-Co-Glycolide) Microspheres. Journal of Controlled Release, 1994. 31(3): p. 293-305). The polydispersity indices of PLA during hydrolytic degradation further confirmed a random chain scission reaction.

The molecular weight distribution (MWD) of PLA containing 0%, 1%, and 10% cellulose nanocrystals were determined via SEC measurement during the hydrolytic degradation. The molecular weight distribution indicated a homogeneously hydrolytic degradation of the electrospun PLA nanocomposite fibers spun from solutions containing 0%, 1%, and 10% cellulose nanocrystals. No autocatalysis was seen in these samples.

Conclusions

Cellulose at the surface of PLA fibers decreased the hydrophobicity of the resulting electrospun non-woven fabrics as evidenced by the water contact angle and water absorption of the fabrics. TGA suggested strong PLA/cellulose nanocrystal interactions at 1% filler loading and agglomeration or poor PLA/cellulose nanocrystal interactions at 10% filler loadings. The electrospun PLA/cellulose nanocomposite fibers became rougher and swelled during hydrolytic degradation in PBS (pH 7.4) at 37° C. changed. The apparent degradation rates based on the molecular weight of PLA were calculated to be 0.0068, 0.0084, and 0.0128 lgM/week for the electrospun PLA/cellulose nanocomposite fibers spun from solutions containing 0, 1%, and 10% cellulose nanocrystals, respectively. Degradation half times derived from molecular weight of PLA are about 44, 36, and 24 weeks for the electrospun PLA/cellulose nanocomposite fibers spun from solutions containing 0, 1%, and 10% cellulose nanocrystals, respectively. Although the addition of 1% cellulose nanocrystals resulted in an insignificant difference in wetting behavior of the resulting non-woven fabric, a significant increase in the hydrolytic degradation rate was achieved. Increasing the cellulose nanocrystal composition from 1% to 10% in the nanocomposite fibers further increased the PLA degradation rate. The increase in degradation rate cannot be explained by the increased interaction between water and PLA alone and may also be attributed to the influence of cellulose nanocrystals on fiber diameter. A linear relationship between lgM and the degradation time suggests that the hydrolytic degradation of electrospun PLA/cellulose nanocomposite fibers in PBS (pH 7.4, 37° C.) were a random chain scission reaction. Polydispersity indices of PLA did not change significantly. The polydispersity indices of PLA during hydrolytic degradation further confirmed a random chain scission degradation mechanism. The molecular weight distribution indicated a homogeneously hydrolytic degradation of the electrospun PLA nanocomposite fibers spun from solutions containing 0%, 1%, and 10% cellulose nanocrystals. No autocatalytic degradation occurred during the hydrolytic degradation of electrospun PLA/cellulose nanocomposite fibers.

6.3 Example 3: Nanocomposite Fibers Electrospun from Poly(Lactic Acid)/Cellulose Nanocrystals for Sustained Release of a Dye that Mimics the Diffusion Characteristics of Several Pesticides Abstract Nanocomposite fibers electrospun from poly(lactic acid) (PLA) containing 0%, 1%, and 10% cellulose nanocrystals were used as chemical delivery systems targeted for controlled release delivery of pesticides. Columbia Blue, a hydrophobic dye with a molecular weight within the pesticide range, was used as a model pesticide for examining release rate profiles of the electrospun nanocomposite fibers. Fifty percent of Columbia Blue (based on the weight of PLA) was incorporated into the nanocomposite fibers during electrospinning. Columbia Blue was released from the electrospun nanocomposite fibers through both diffusion-controlled mechanism and degradation-controlled mechanism. The electrospun nanocomposite fibers containing Columbia Blue formed different crystalline polymorphs than the dye-free nanocomposite fibers. During the release experiments, Columbia Blue was identified by liquid chromatography/mass spectroscopy (LC/MS), and the LC/MS spectrum confirmed that Columbia Blue did not degrade during the 16 week release experiments. Columbia Blue which was released by diffusion-controlled mechanism followed Fickian transport (n=0.5). The release profiles of Columbia Blue by degradation-controlled mechanism followed zero-order, time-independent Case II kinetics (n=1.0). The rate of release by both diffusion controlled and degradation controlled mechanisms increased with increasing cellulose content of the fibers. Degradation of the PLA was confirmed by measured decrease in the molecular weight of PLA during the release experiments.

Introduction

In agriculture, electrospinning has been identified as one of the potential methods of applying fibers to plants or planting sites. The simplicity of the electrospinning process itself, the ability to vary the fiber diameter by changing the solution concentration and/or the surface tension of the liquid, and the ability to incorporate therapeutic compounds into non-woven fabrics during electrospinning afford the prospect of preparing useful polymeric systems for controlled drug delivery. Flat non-woven fabrics that can be either fabricated or cut to almost any size represent an attractive form for topical delivery applications, and other shapes (e. g., tubes) can be constructed using different target geometries. Moreover, a significant implication of the mechanism of electrospinning is that materials derived from polymer blends will not likely be an admixture of two different fibers but rather fibers containing both components, in principle offering another and quite unique means of controlling release rates (Deitzel, J. M., Kleinmeyer, J., Harris, D., Beck Tan, N. C., The effect of processing variables on the morphology of electrospun nanofibers and textiles. Polymer, 2001. 42(1): p. 261-272). The combination of high porosity and nanoscale pores achievable via electrospinning is also unique.

A drug can be released from a biodegradable delivery system by diffusion through a polymer matrix or pores in the matrix and/or after the degradation of the polymer backbone and erosion of the matrix. The drug release may be controlled by diffusion, by a combination of diffusion and erosion, or solely by erosion of the delivery system. Tuovinen et al. (Tuovinen, L., S. Peltonen, and K. Järvinen, Drug release from starch-acetate films. Journal of Controlled Release, 2003. 91(3): p. 345-354) studied the effect of hydrophobicity of a drug on its release from starch based films. They used sotalol and timolol as model drugs to study the effect of hydrophobicity of the drug on its release from the films. These drugs have very similar pKa values and molecular weights, but substantially different partition coefficients. The log $K_{ow}$ (logarithm of partition coefficient, octanol/aqueous pH 7.65) value for sotalol is −0.62 with the corresponding value for timolol being 1.91. The release of sotalol and timolol from the potato starch film was comparable with and without α-amylase. In contrast, the hydrophobicity of the drug affected its release rate from both potato starch acetate films. Sotalol was released faster than the more hydrophobic molecule, timolol, under the same conditions. These results demonstrate the stronger interaction between the starch acetate films and timolol due to the hydrophobic nature.

Kenawy et al. (Kenawy, E.-R., Bowlin, Gary L., Mansfield, Kevin, Layman, John, Simpson, David G., Sanders, Elliot H., Wnek, Gary E., Release of tetracycline hydrochloride from electrospun poly(ethylene-co-vinylacetate), poly (lactic acid), and a blend. Journal of Controlled Release, 2002. 81(1-2): p. 57-64) reported the drug delivery potential of electrospun polymers by spinning poly(ethylene co-vinyl acetate) (PEVA) and poly(lactic acid) (PLA) fibers containing tetracycline hydrochloride as the model drug. They observed that the electrospun PEVA and 50/50 PLA/PEVA non-woven fabrics released tetracycline at a constant rate over a period of five days. These observations stress the importance of electrospun non-woven fabrics in controlled drug delivery systems and other biomedical applications. Kenawy et al. (Kenawy, E.-R., Bowlin, Gary L., Mansfield, Kevin, Layman, John, Simpson, David G., Sanders, Elliot H., Wnek, Gary E., Release of tetracycline hydrochloride from electrospun poly(ethylene-co-vinylacetate), poly(lactic acid), and a blend. Journal of Controlled Release, 2002. 81(1-2): p. 57-64) also reported the release behavior of the tetracycline hydrochloride from PEVA, PLA and a blend. It disclosed that the non-woven fabrics of PLA fibers exhibited some instantaneous release, most probably from tetracycline hydrochloride on the fiber surfaces, but the amount of drug released was negligible over 50 hrs. This was likely due to the partial crystallinity of PLA, which limits the diffusion of the aqueous environment into the inner layers of the polymer and consequently limits the diffusion of the drug from the fibers. They also compared the total percent tetracycline hydrochloride released from cast films and electrospun non-woven fabrics. The total percent released from the cast films was lower than from electrospun non-woven fabrics. The lower total percent release from the films was attributed to their much lower surface area as compared to electrospun non-woven fabrics.

Zeng et al. (Zeng, J., Yang, Lixin, Liang, Qizhi, Zhang, Xuefei, Guan, Huili, Xu, Xiuling, Chen, Xuesi, Jing, Xiabin, Influence of the drug compatibility with polymer solution on the release kinetics of electrospun fiber formulation. Journal of Controlled Release, 2005. 105(1-2): p. 43-51) studied the influence of drug compatibility with polymer solution on the release kinetics of electrospun fiber formulation. Encapsulation of paclitaxel, doxorubicin base and doxorubicin hydrochloride by electrospinning PLA fiber mats was studied. Preferable encapsulation of paclitaxel and doxorubicin base was found to be owing to good compatibility with PLA and solubility in chloroform/acetone solvent system, whereas doxorubicin hydrochloride was observed on or near the surface of PLA fibers. The release of paclitaxel and doxorubicin base from electrospun PLA fiber samples followed nearly zero-order kinetics due to the degradation of the fibers. However, an obvious burst release was found for doxorubicin hydrochloride. In order to encapsulate a majority of the drugs inside the polymer fibers and thus to acquire a constant and stable drug release profile, a hydrophobic polymer was chosen as the fiber material for a hydrophobic drug while a hydrophilic polymer was employed for a hydrophilic drug, and the solvents used should be good for both the drug and the polymer. Otherwise, the drug cannot dissolve in the polymer solution and only disperses in it. After electrospinning the drugs were located on or near the fiber surface and their rapid diffusion into the release media resulted in burst release.

The diffusion of the liquid (or vapor) out of the solid matrix is normally described in terms of Fick's laws. Fick's first law is usually written in terms of the flux through a surface. The flux is assumed to be proportional to the concentration gradient in which the constant of proportionality is known as the diffusion coefficient. Fick's second law relates the concentration change as a function of time to the change in flux with respect to the position. Fickian diffusion predicts that the penetrant is sorbed at a rate proportional to the square root of time. A fundamental criterion for Fickian diffusion is that the surface concentration immediately attains its equilibrium value upon a change in conditions and remains constant through the sorption process, i.e., in a resin matrix system the polymer chain segments in the surface layers must instantaneously equilibrate. Fickian diffusion is rarely observed in the transport of a liquid through glassy polymer (Vrentas J. S., V. C. M., Evaluation of free-volume theories for solvent self-diffusion in polymer-solvent systems. Journal of Polymer Science Part B: Polymer Physics, 1993. 31(1): p. 69-76; Petropoulos, J. H., Sanopoulous, M., Papadokostaki, K. G., Fundamentals of transport phenomena in polymer solution-diffusion membranes, in Surfactant Science Series: Surface chemistry and electrochemistry of membranes, M. D. Torben Smith Sorensen, Editor. 1999. p. 167).

Fickian diffusion (the dynamic dispersion of a concentrated material in a larger medium in which a concentration gradient is the primary driving force) is the most common mathematical model for controlled release (Mary Marshall, S. W., Christopher Brazel, Matthew Alexander, Susumu Akatagawa, Controlled Delivery of Pesticides Through Synthetic Biodegradable Polymer Compositions, in Controlled-release Delivery Systems for Pesticides, H. B. Scher, Editor. 1999, Marcel Dekker, Inc: New York. p. 263-295). A simplified model for fractional release was developed by Ranson and Peppas (Franson, N. M. and N. A. Peppas, Influence of Co-Polymer Composition on Non-Fickian Water Transport through Glassy Co-Polymers. Journal of Applied Polymer Science, 1983. 28(4): p. 1299-1310):

$$M_t/M_\infty = kt^n + C \tag{1}$$

where $M_t$ is the mass of active ingredient released from a controlled release device at any time t, $M_\infty$ is the corresponding mass released at infinite time, and k and n are empirical parameters indicative of the release kinetics. The constant C represents the burst release, or the amount of active ingredient released immediately at time zero. The value of n determines the dependence of the release rate on time (Peppas, N. A. and A. R. Khare, Preparation, structure and diffusional behavior of hydrogels in controlled release. Advanced Drug Delivery Reviews, 1993. 11(1-2): p. 1-35). Time-independent drug release is described by the value of n=1.0. The constant k incorporates characteristics of the macromolecular network/drug system and the dissolution medium.

The four assumptions from this model are: (1) the diffusion medium does not swell or interact with the active ingredient, (2) release occurs when the active ingredient dissolves in a solvent that penetrates the diffusion medium, (3) there is a perfect sink condition at the surface of the controlled-release device (i.e., the concentration of the active ingredient outside the controlled-release device is zero), and (4) all diffusion occurs away from the center of the device (symmetry condition) (Franson, N. M. and N. A. Peppas, Influence of Co-Polymer Composition on Non-Fickian Water Transport through Glassy Co-Polymers. Journal of Applied Polymer Science, 1983. 28(4): p. 1299-1310).

The value of n for Fickian diffusion depends upon the geometry of the system (Mary Marshall, S. W., Christopher Brazel, Matthew Alexander, Susumu Akatagawa, Controlled Delivery of Pesticides Through Synthetic Biodegradable Polymer Compositions, in Controlled-release Delivery Systems for Pesticides, H. B. Scher, Editor. 1999, Marcel Dekker, Inc: New York. p. 263-295). In planar devices, where one-dimensional diffusion occurs, n=0.50 (generally, when the aspect ratio is greater than 10, the one-dimensional diffusion is assumed) (Brazel, C. S., Solute and Water Transport in Polymeric, Swelling-Controlled Release Systems. 1997, Purdue University: West Lafayette, Ind.).

In degradable systems, the protective polymer coating can release the active ingredient by either surface or bulk erosion (especially common in systems that undergo large internal stresses when exposed to the release medium) (Mary Marshall, S. W., Christopher Brazel, Matthew Alexander, Susumu Akatagawa, Controlled Delivery of Pesticides Through Synthetic Biodegradable Polymer Compositions, in Controlled-release Delivery Systems for Pesticides, H. B. Scher, Editor. 1999, Marcel Dekker, Inc: New York. p. 263-295). When surface degradation occurs very rapidly compared to diffusion, the release mechanism will be controlled largely by the geometry of the device (Mary Marshall, S. W., Christopher Brazel, Matthew Alexander, Susumu Akatagawa, Controlled Delivery of Pesticides Through Synthetic Biodegradable Polymer Compositions, in Controlled-release Delivery Systems for Pesticides, H. B. Scher, Editor. 1999, Marcel Dekker, Inc: New York. p. 263-295). In planar systems, the solute release rate should be fairly constant (Case II diffusion with n=1.0) because each successive layer of carrier liberated contains the same concentration of the active ingredient. In spherical systems, the release rate will decrease with time, since the surface area of each successive layer is smaller, as with peeling an onion; so near time zero, n=1.0, it will eventually fall below 0.5. In analyzing the surface erosion release from biodegradable systems using Equation (1) to fit experimental data and determine an "n" value, deviations of n of ~0.05 (assuming a correlation coefficient of 0.99) from the typical Fickian behavior are sufficient to indicate that the degradation process affects the release profile (Mary Marshall, S. W., Christopher Brazel, Matthew Alexander, Susumu Akatagawa, Controlled Delivery of Pesticides Through Synthetic Biodegradable Polymer Compositions, in Controlled-release Delivery Systems for Pesticides, H. B. Scher, Editor. 1999, Marcel Dekker, Inc: New York. p. 263-295).

Previous work (Xiang, C. and M. W. Frey, Hydrolytic Degradation of Nanocomposite Fibers Electrospun from Poly(lactic acid)/Cellulose Nanocrystals. Submitted to Biomacromolecules) showed that the hydrolytic degradation rate of PLA/cellulose nanocomposite fibers increased as the incorporation of cellulose nanocrystals into the electrospun PLA fibers. In the present example, nanocomposite fibers electrospun from PLA containing 0%, 1%, and 10% cellulose nanocrystals were used as pesticide carriers. Columbia Blue, a hydrophobic dye, was used as a model pesticide for examining release profiles of the electrospun nanocomposite fibers. Nanocomposite fibers containing Columbia Blue were characterized using field emission scanning electron microscopy (FESEM) before and after the release experiments. The crystallinity of the nanocomposite fibers containing Columbia Blue was investigated using differential scanning calorimetry (DSC). Columbia Blue was released from the electrospun nanocomposite fibers through both diffusion-controlled mechanism and fiber degradation-controlled mechanism. During the release experiments, Columbia Blue was identified with liquid chromatography/mass spectroscopy (LC/MS). Data was presented as the mean±standard errors of the cumulative percent of Columbia Blue released from triplicate systems.

Materials and Methods

Materials

Microcrystalline cellulose powder (MCC, extra pure, average particle size 90 µm) was purchased from Acros Organics (Geel, Belgium). Cellulose nanocrystals were prepared from the microcrystalline cellulose by acid hydrolysis. Polylactic acid (Mw=211,332 Da, Mn=109,337 Da) was supplied by Cargill Dow (Minnetonka, Minn.) and phosphate buffered saline (PBS) (p-5368, pH 7.4) was purchased from Sigma-Aldrich (St. Louis, Mo.). Columbia Blue was purchased from DayGlo Color Corp. (Cleveland, Ohio). N,N-dimethyl formamide (DMF) and acetonitrile were purchased from Mallinckrodt Laboratory Chemicals (Phillipsburg, N.J.). All the reagents were used without further purification.

Incorporation of Columbia Blue into Nanocomposite Fibers Electrospun from PLA/Cellulose Nanocrystals Based on the weight of the PLA, fifty percent of Columbia Blue was incorporated into the nanocomposite fibers electrospun from PLA containing 0%, 1%, and 10% cellulose nanocrystals. Cellulose nanocrystals were first dispersed in DMF overnight with an ultrasonic liquid processor (Misonix Sonicator® 3000) in a water bath. Then a fixed amount of PLA and Columbia Blue were added. Next, the suspension was heated to about 100° C. for PLA dissolution in DMF under constant stirring. After the PLA was thoroughly dissolved in DMF, the blended mixture was electrospun at 70° C. to produce nanocomposite fibers. During Electrospinning, the polymer suspension was introduced into a 5 mL glass syringe (VWR Scientific, West Chester, Pa.). The syringe was attached with a metal needle (ID=0.60 mm) and put into a shielded heating unit that was pre-heated to 70±5° C. and controlled by a Watlow controller (St. Louis, Mo.). After about 10 minutes of thermal equilibration, electrospinning was started at 15 kV which was supplied by a high voltage supply (Gamma High Voltage Research Inc., FL), and at 10 µL/min feed rate driven by a programmable syringe micropump (Harvard Apparatus, MA). A rotating Aluminum plate (Diameter=20 cm) covered with aluminum foil was used to collect nanocomposite fibers at a 10 cm distance away from the needle tip. Each sample was collected for five hours.

Characterization of Nanocomposite Fibers Electrospun from PLA/Cellulose Nanocrystals Containing Columbia Blue The morphology of the electrospun PLA/cellulose nanocomposite fibers containing Columbia Blue was observed with a LEO 1550 field emission scanning electron microscope (FESEM) at a voltage of 3 kV. The fibers were sputter-coated with a 2-3 nm layer of gold and palladium for imaging using a Desk II cold sputter/etch unit. The thermal properties of the electrospun PLA/cellulose nanocomposite fibers containing Columbia Blue were investigated by Differential Scanning calorimetry (DSC) (DSC 2920, TA Instruments Inc.). Samples of approximately 10 mg were loaded and heated in a nitrogen atmosphere at a rate of 10° C./min from 0° C. to 200° C. The pore size of the electrospun PLA/cellulose non-woven fabrics containing Columbia Blue was measured with an 1100-AEHXL capillary flow porometer (Porous Media, Inc.). The non-woven fabrics were cut into two-inch-diameter circles for the porometry measurement. Three specimens for each sample were measured. The molecular weight of the PLA of the electrospun nanocomposite fibers containing Columbia Blue was determined by Size Exclusion chromatography (SEC) (a Waters 486 UV detector and a Waters 2410 differential refractive index detector, Waters Corporation), using polystyrene standards for calibration and tetrahydrofuran (THF) as the carrier solvent at 40° C. with a flow rate of 0.5 ml/min. For SEC measurements, the electrospun PLA/cellulose nanocomposite fibers were dissolved in THF. The cellulose nanocrystals were removed by syringe filters with a pore size of 0.45 µm (Millipore) and the molecular weight of PLA was measured.

Columbia Blue Release Measurement

Columbia Blue Release from the Nanocomposite Fibers by Diffusion

Approximately 0.2 g electrospun PLA/cellulose non-woven fabrics containing Columbia Blue were immersed in 100 ml distilled and deionized water in closed bottles. Columbia Blue release from the electrospun PLA/cellulose nanocomposite fibers was examined by shaking at 200 rpm using a platform shaker (Innova™ 2300, New Brunswick Scientific)

at room temperature for 48 hrs. At predetermined time intervals, 0.5 hr, 1 hr, 2 hrs, 4 hrs, 6 hrs, 8 hrs, 12 hrs, 16 hrs, 24 hrs, 36 hrs, and 48 hrs, samples of 1 ml were collected. After sampling, 1 ml fresh distilled and deionized water was added. The treatment was performed in triplicate. The 1 ml sample was then mixed with 9 ml DMF for the Columbia Blue concentration measurement.

The concentration of Columbia Blue was determined using Liquid Chromatography/Mass Spectroscopy (LC/MS) (Agilent Technologies 6130 Quadrupole LC/MS), and the Columbia Blue was identified using mass spectroscopy. The column used was a Restek Ultra C18, 5 μm, 250×4.6 mm. The mobile phase consisted of 60% acetonitrile and 40% water at a flow rate of 1.0 ml/min. The concentration was determined using UV detection at a wavelength of 374 nm.

Columbia Blue Release from the Nanocomposite Fibers Via Fiber Hydrolytic Degradation with Diffusion Study After the diffusion study, the electrospun PLA/cellulose nanocomposite fibers were dried at 25° C. under vacuum for a week until a constant weight was achieved. Then release rate experiments were performed by suspending a dye-loaded electrospun non-woven fabric in 100 ml of phosphate buffer saline, pH 7.4, at 37° C. in a shaking (100 rpm) water bath (Julabo SW 23, Seelbach, Germany) for sixteen weeks. After nine weeks, the release media were increased to 200 ml of PBS solutions. Samples of 1 ml were taken from the release medium per week. After sampling, 1 ml fresh PBS solution was added. The release was measured in triplicate. The treatment was performed in triplicate. The 1 ml sample was then mixed with 9 ml DMF for the Columbia Blue concentration measurement. The hydrolytic degradation time of the electrospun nanocomposite fibers was set to be sixteen weeks, which was the same time period as the electrospun nanocomposite fibers without Columbia Blue. As in the diffusion experiment, the concentration of Columbia Blue was measured.

Columbia Blue Release from the Nanocomposite Fibers Via Fiber Hydrolytic Degradation without Diffusion Study The release of Columbia Blue from the nanocomposite fibers electrospun from PLA with 0%, 1%, and 10% cellulose nanocrystals was conducted by suspending about 10 mg dye-loaded electrospun non-woven fabrics in 10 ml of phosphate buffer saline, pH 7.4, at 37° C. in a shaking (100 rpm) water bath (Julabo SW 23, Seelbach, Germany). Samples were removed from the release media and the 10 ml release media were then mixed with 90 ml DMF for Columbia Blue concentration measurement in 4 weeks, 8 weeks, 12 weeks, and 16 weeks. The treatment was performed in triplicate.

Results and Discussion

Identification of Columbia Blue

A model pesticide, Columbia Blue, was chosen following Briggs's "rule of 3" (Briggs, G. G., Uptake of Agrochemicals & Pharmaceuticals 'Predicting uptake & movement of agrochemicals from physical properties', in SCI Meeting. 1997) and Clarke-Delaney's "guide of 2" (Clarke, E. D. and J. S. Delaney, Designing Drugs and Crop Protectants: Processes, Problems and Solutions, ed. D. L. M. Ford, J. Dearden, H. V. de Waterbeemd. 2003: Blackwell Publishing, Malden). During the release measurements, Columbia Blue was identified by the LC/MS. The retention time of Columbia Blue of HPLC spectrum remained unchanged at 9.8 minutes. The mass spectrum of Columbia Blue also did not change. Therefore, Columbia Blue did not degrade in the release media (i.e., water at room temperature, and PBS of pH 7.4 at 37° C.) used in this study.

Figure 8:
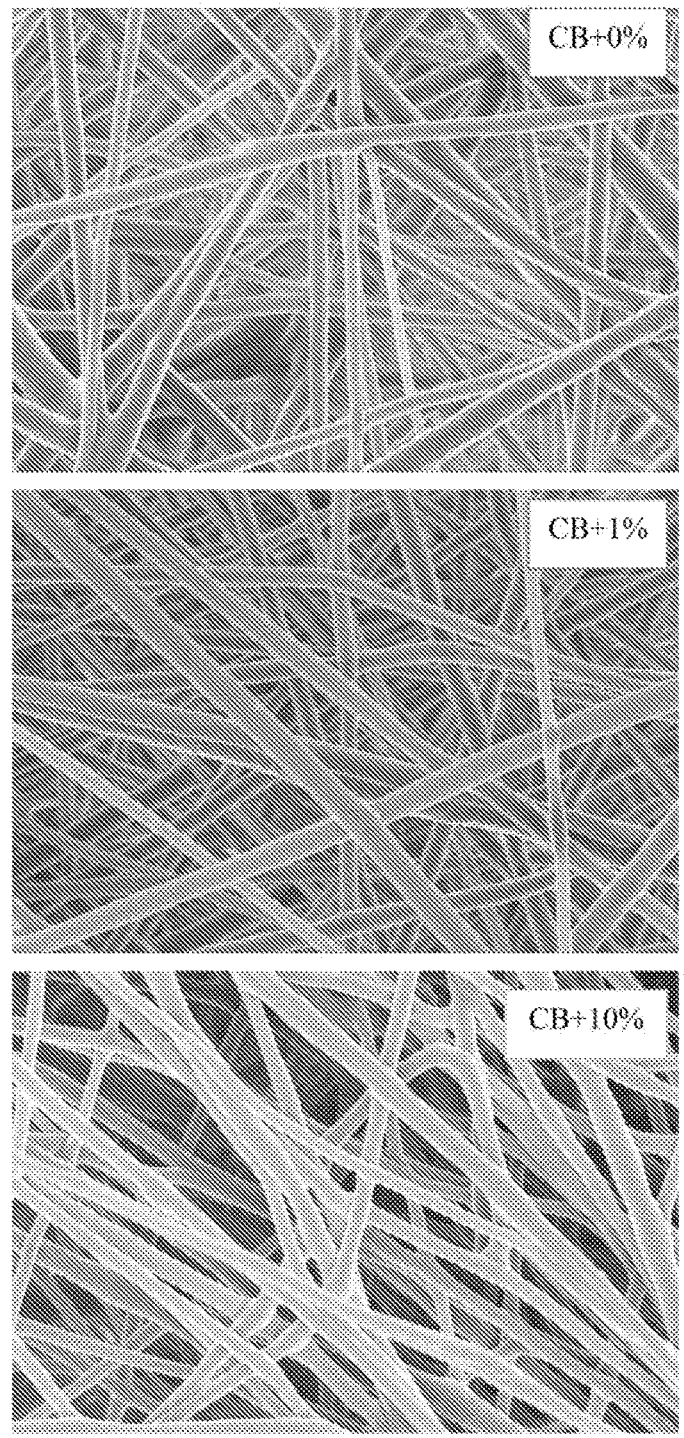
FIG. 8. FESEM images of electrospun PLA/cellulose nanocomposite fibers containing Columbia Blue after dye release measurement. Magnification 10,000×. See Section 6.3 for details.

Morphology of the Nanocomposite Fibers Electrospun from PLA/Cellulose Nanocrystals Containing Columbia Blue FIG. 8 shows the morphology of the nanocomposite fibers containing 50% (based on the weight of PLA) Columbia Blue electrospun from PLA with 0%, 1%, and 10% cellulose nanocrystals. The average fiber diameter of the electrospun PLA/cellulose nanocomposite fibers was determined. Fifty fibers were measured from the FESEM images to obtain the average fiber diameter. The average fiber diameter did not change significantly as the cellulose nanocrystal content changed increased from 0%, to 1%, and 10% w/w PLA. The mean pore size of the electrospun non-woven fabrics containing 50% Columbia Blue was also determined. Non-woven fabrics electrospun from PLA containing 10% cellulose nanocrystals had a larger mean pore sized than those from PLA with 0% and 1% cellulose nanocrystals.

Columbia Blue Release Measurement

This example demonstrates that the incorporation of cellulose nanocrystals into electrospun PLA nanocomposite fibers increased the crystallinity and mechanical properties of PLA (Xiang, C. J., Yong L; Frey Margaret W, Nanocomposite Fibers Electrospun from Poly(lactic acid)/Cellulose Nanocrystals. Journal of Biobased Materials and Bioenergy, 2009. 3(2): p. 147-155) and improved the hydrophilicity of PLA (Xiang, C. and M. W. Frey, Hydrolytic Degradation of Nanocomposite Fibers Electrospun from Poly(lactic acid)/Cellulose Nanocrystals. Submitted to Biomacromolecules). The influence of the incorporation of cellulose nanocrystals into the electrospun PLA nanocomposite fibers on pesticide release rate profiles was examined. The morphology of the Columbia-Blue-loaded nanocomposite fibers was examined with FESEM after the sixteen-week release experiments (data not shown). After the release study, the uniformity of the nanocomposite fibers changed. Agglomerates were observed on the surface of the fibers. These indicate the degradation of the nanocomposite fibers during the release experiments.

Figure 9:
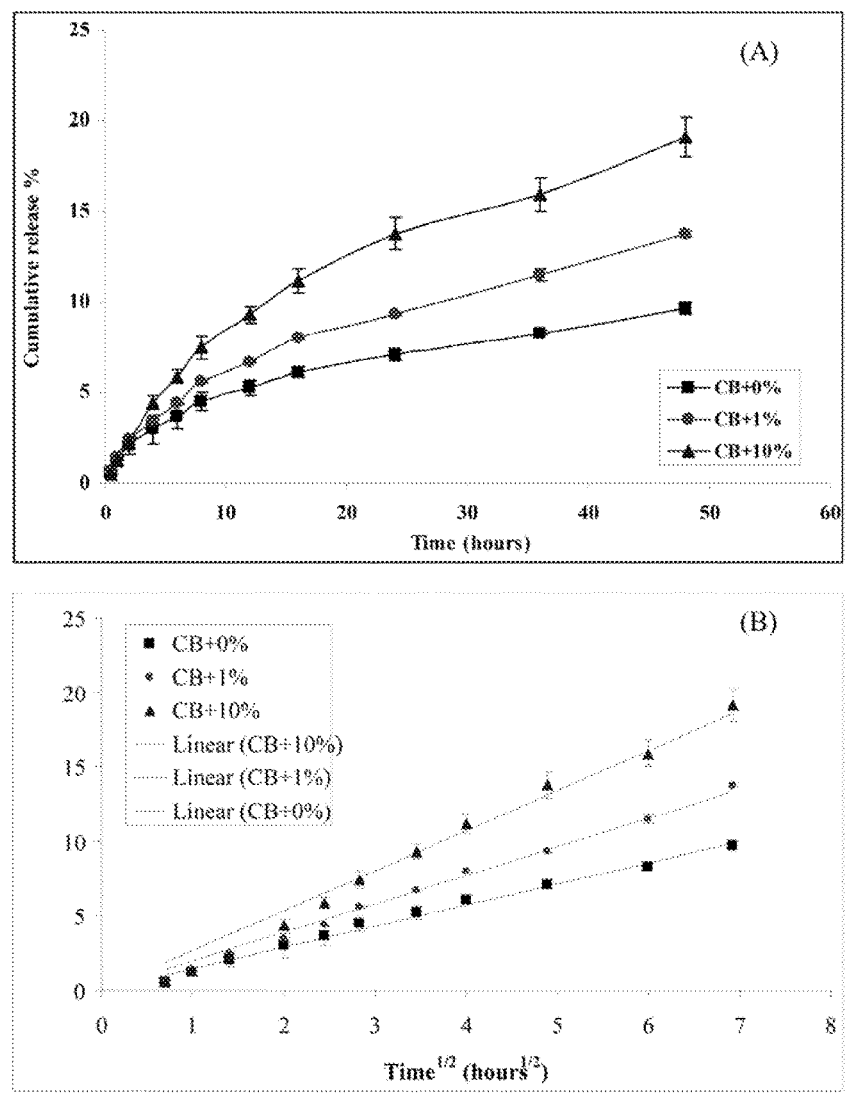
FIG. 9. Effect of time on the release of Columbia Blue from the nanocomposite fibers electrospun from PLA containing 0%, 1%, and 10% cellulose nanocrystals. (A) Time. (B) Square root of time. Solid lines in the square root of time plot (B) represent the linear regressions of the cumulative release. See Section 6.3 for details.

The release profiles of a model hydrophobic pesticide, Columbia Blue, from the nanocomposite fibers electrospun from PLA containing 0%, 1%, and 10% cellulose nanocrystals, are illustrated in FIG. 9. The dye-loaded electrospun non-woven fabrics were suspended in distilled and deionized water for 48 hours at room temperature. As shown in FIG. 9(A), less than 20% of Columbia Blue was released from the nanocomposite fiber after 48 hour diffusion-controlled release. The burst release of Columbia Blue from the electrospun nanocomposite fibers is not significant. Incorporation of cellulose nanocrystals into the PLA nanocomposite fibers increased the Columbia Blue release. The higher the cellulose nanocrystal content, the faster Columbia Blue released. The considerably higher hydrophilicity of the nanocomposite fibers containing 10% cellulose nanocrystals is believed to be the predominate factor for the much faster release of this hydrophobic model pesticide. These results are consistent with the results by other investigators. Cook et al. (Cook, T. J., G. L. Amidon, and V. C. Yang, Polypeptides for controlled release applications: Synthesis and preliminary characterization and release studies. International Journal of Pharmaceutics, 1997. 159(2): p. 197-206) and Markland et al. (Markland, P., G. L. Amidon, and V. C. Yang, Modified polypeptides containing [gamma]-benzyl glutamic acid as drug delivery platforms. International Journal of Pharmaceutics, 1999. 178(2): p. 183-192) demonstrated that increasing polypeptide hydrophobicity at either the monomeric level or at a bulk scale could enhance the release rate of low molecular weight drugs. To assess the mechanism of Columbia Blue release, a plot of cumulative release percentage versus the square root of time was completed (FIG. 9 (B)). This relationship, derived from Fick's Second Law, is indicative of diffusional release of a compound from the polymer matrix. As illustrated in FIG. 9 (B), the 50% loaded electrospun nanocomposite fibers released Columbia Blue in a linear mechanism as a function of the square root of time ($R^2$=0.99). Columbia Blue release from the nanocomposite fibers electrospun PLA containing 0%, 1%, and 10% cellulose nanocrystals was governed by a Fickian diffusion-controlled mechanism as reflected by the presence of a linear relationship between Columbia Blue release and the square root of time (FIG. 9 (B)). The different release rates of Columbia Blue have demonstrated both the feasibility of our concept of utilizing modified PLA to provide regulated and diffusion-controlled pesticide release rates.

The release profiles of Columbia Blue governed by a degradation-controlled mechanism within nine weeks were determined. In these studies, the dye-loaded electrospun non-woven fabrics were processed in PBS (pH 7.4) at 37° C.

The release experiments were conducted for sixteen weeks. Columbia Blue release from the electrospun nanocomposite fibers by degradation-controlled mechanism followed zero-order kinetics ($R^2$=0.98). Zeng et al. (Zeng, J., Yang, Lixin, Liang, Qizhi, Zhang, Xuefei, Guan, Huili, Xu, Xiuling, Chen, Xuesi, Jing, Xiabin, Influence of the drug compatibility with polymer solution on the release kinetics of electrospun fiber formulation. Journal of Controlled Release, 2005. 105(1-2): p. 43-51) also reported this almost idea release of paclitaxel in the buffer containing 0.01 mg/rill proteinase K from PLLA electrospun fibers. The release profile of Columbia Blue from the nanocomposite fibers had a higher release rate. The slope of the line is determined the release rate. Zero-order, time-independent Case II kinetics (n=1.0) is characterized by a linear mass uptake and/or release with time (Peppas, N. A. and A. R. Khare, Preparation, structure and diffusional behavior of hydrogels in controlled release. Advanced Drug Delivery Review's, 1993. 11(1-2): p. 1-35). In non-Fickian or anomalous transport, diffusion as well as macromolecular relaxation time scales are similar and both control the overall rate of penetrant absorption. Case II transport is the limit when relaxation predominates. The release profiles of Columbia Blue governed by a degradation-controlled mechanism from eleven weeks to sixteen weeks were also studied (data not shown). The linear relationship observed further confirmed the zero-order, time-independent Case II kinetics.

After sixteen weeks, 36%, 44%, and 56% Columbia Blue released from the PLA nanocomposite fibers containing 0%, 1%, and 10% cellulose nanocrystals respectively.

Figure 10:
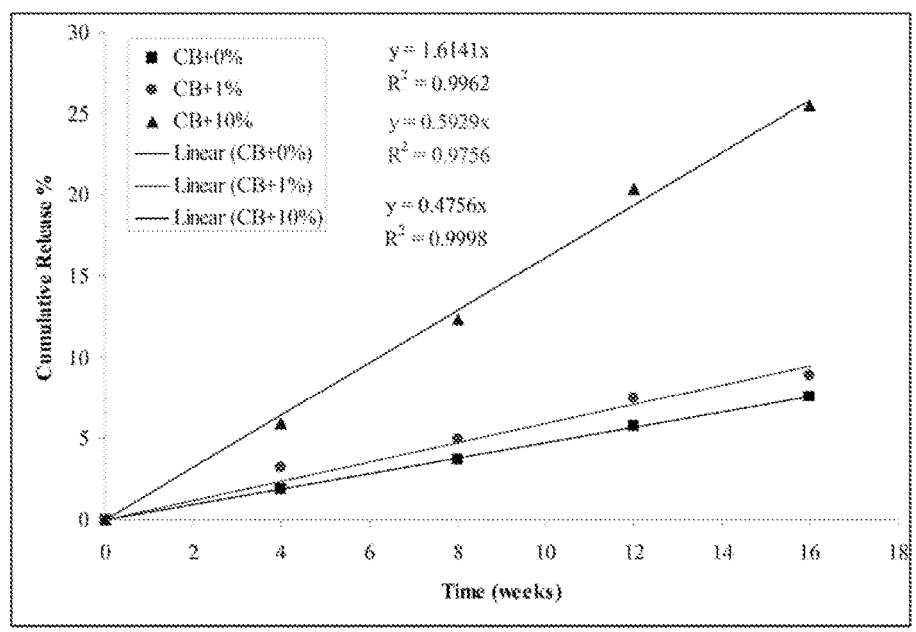
FIG. 10. Cumulative release percentage of Columbia Blue from the nanocomposite fibers electrospun from PLA containing 0%, 1%, and 10% cellulose nanocrystals by fiber degradation. See Section 6.3 for details.

FIG. 10 shows the release profiles of Columbia Blue from the electrospun nanocomposite fibers containing 0%, 1%, and 10% cellulose nanocrystals by fiber degradation without diffusion study. Zero-order, time-independent Case II kinetics (n=1.0) kinetics were further confirmed.

Molecular Weight Change of PLA During Columbia Blue Release Experiments

Cumulative release percentage of Columbia Blue from the nanocomposite fibers containing 0%, 1%, and 10% cellulose nanocrystals versus the molecular weight of PLA during the release study was determined (data not shown). The faster the fiber degraded, the more Columbia Blue released from the nanocomposite fibers.

Thermal Properties of PLA Before and after Columbia Blue Release Measurements

The thermal properties of PLA from the electrospun PLA/cellulose nanocomposite fibers containing Columbia Blue were determined before and after the Columbia Blue release study (data not shown). After the sixteen-week Columbia Blue Release study, the original bimodal melting peak disappeared and monomodal melting peak appeared.

The temperatures of the major peaks from DSC thermographs of PLA from various nanocomposite fibers are summarized in Table 8. The glass transition temperature of PLA in the nanocomposite fibers decreased after the sixteen-week release study. We reported that the glass transition temperature of the nanocomposite fibers containing 0%, 1%, and 10% cellulose nanocrystals were 58° C., 59° C., 59° C. respectively (Xiang, C. J., Yong L; Frey Margaret W, Nanocomposite Fibers Electrospun from Poly(lactic acid)/Cellulose Nanocrystals. Journal of Biobased Materials and Bioenergy, 2009. 3(2): p. 147-155). Before the release study, the incorporation of Columbia Blue occupied the free volume of the PLA molecules. Hence the glass transition temperature of PLA in the nanocomposite fibers increased. After the release study, the glass transition temperature of PLA in the nanocomposite fibers decreased, which indicated that Columbia Blue acted as plasticizer.

TABLE 8

DSC summary of PLA from the electrospun PLA/cellulose nanocomposite fibers before and after the Columbia Blue release study.

| | $T_g$ (° C.) | $T_m$ (° C.) |
|---|---|---|
| CB + 0% Cellulose PLA-Before | 66 | 71, 123, 133 |
| CB + 1% Cellulose PLA-Before | 65 | 71, 123, 133 |
| CB + 10% Cellulose PLA-Before | 66 | 71, 124, 134 |
| CB + 0% Cellulose PLA-After | 56 | 69, 137 |
| CB + 1% Cellulose PLA-After | 55 | 68, 138 |
| CB + 10% Cellulose PLA-After | 53 | 66, 140 |

Conclusions

Fifty percent of Columbia Blue (on the weight of PLA) was successfully incorporated into the nanocomposite fibers electrospun from PLA containing 0%, 1%, and 10% cellulose nanocrystals. The average fiber diameters did not change significantly with the incorporation of Columbia Blue. During the release experiments, Columbia Blue did not degrade in the release media. Columbia Blue release by diffusion-controlled mechanism followed a Fickian diffusion mechanism. After sixteen weeks, 36%, 44%, and 56% Columbia Blue released from the PLA nanocomposite fibers containing 0%, 1%, and 10% cellulose nanocrystals respectively by both diffusion-controlled mechanism and fiber-degradation controlled mechanism. The release rate profiles of Columbia Blue by degradation-controlled mechanism followed zero-order, time-independent Case II kinetics (n=1.0). The burst release of Columbia Blue from the electrospun nanocomposite fibers was not obvious. The faster the nanocomposite fiber degraded, the higher Columbia Blue released from the fibers. The molecular weight of PLA decreased and the crystallinity of PLA from the electrospun PLA/cellulose nanocomposite fibers containing Columbia Blue confirmed that the hydrolytic degradation of the nanocomposite fibers occurred. The addition of Columbia Blue increased the glass transition temperature of PLA. After the release study, the glass transition temperature of PLA in the nanocomposite fibers decreased, which indicated that Columbia Blue acted as plasticizer.

6.4 Example 4: Use of PLA with Imidacloprid Included to Control Leaf Feeding Beetles This example describes trials in which a PLA polymeric material was tested, with and without a pesticidal compound of interest, imidacloprid, included, for controlling leaf feeding beetles. The example demonstrates that a toxic dose of imidacloprid can be delivered in a PLA polymeric carrier.

Trials 1-3. Seed Coating with a PLA Film.

Figure 11:
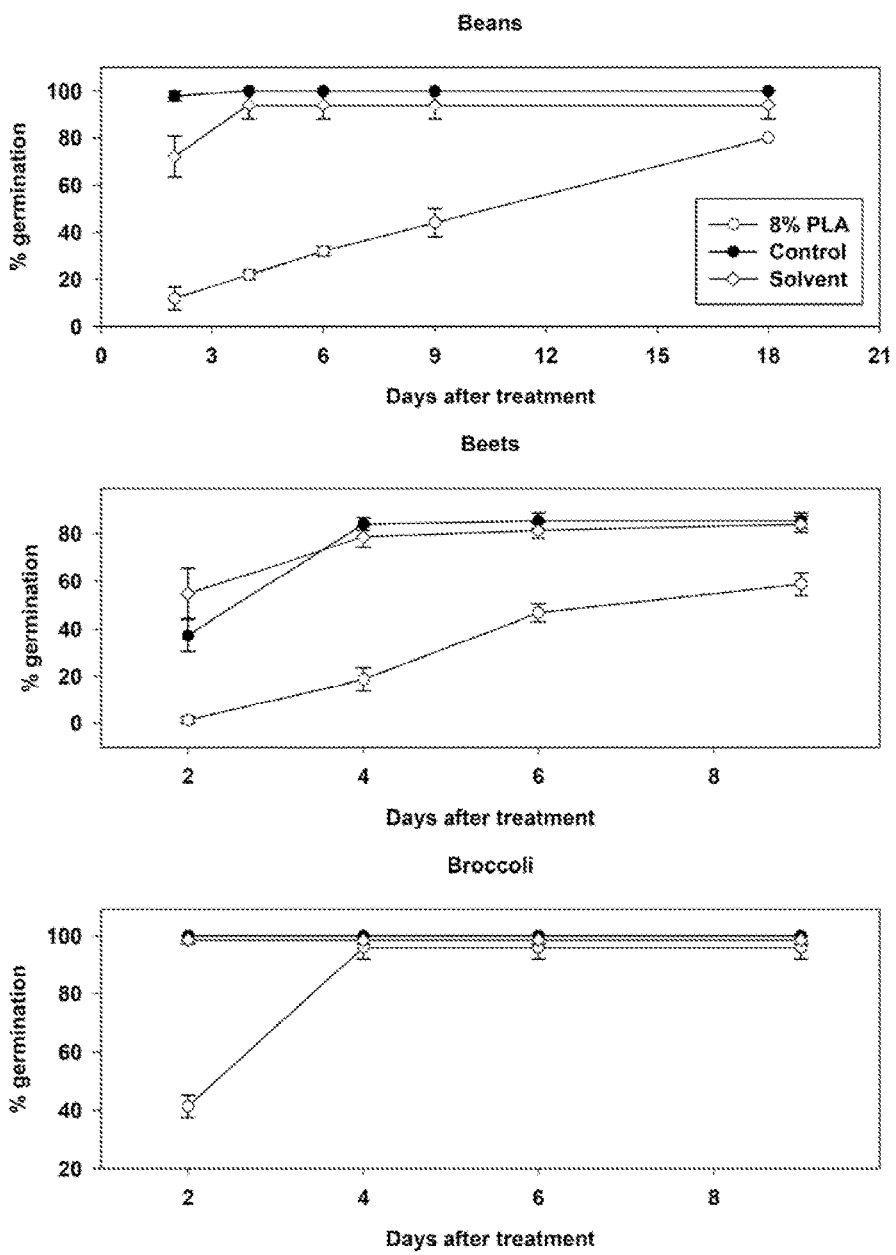
FIG. 11. Seed germination after coating seeds with PLA films. See Section 6.4 for details.

Trial 1:

Seeds of bean, broccoli, and beet were dipped in 8% PLA in 3:1 chloroform:acetone solvent. Controls were seeds dipped in the solvent without PLA. Dipped seeds were air dried to remove residual solvent and then placed in Petri dishes with moistened filter paper above and below the seed. Moisture was applied as needed over the duration of the experiment. Germination was evaluated at regular intervals. Controls and solvent-dipped seeds showed good germination over time, but a PLA film coating the seed inhibited germination (FIG. 11).

Trial 2:

Bean seeds (Roma II) were weighed, dipped in 4% PLA in 4:3 chloroform:acetone solvent, and then weighed again. Average mass of PLA/seed was 0.00145±0.0001 g/seed. PLA treated and untreated seeds (n=10/treatment) were placed between moistened filter papers within a food storage container that was sealed with a lid and placed in an incubator held at 28 C. Germination was recorded 5 days post treatment. At that time, Controls had 100% germination and PLA treated seeds had 40% germination.

Figure 12:
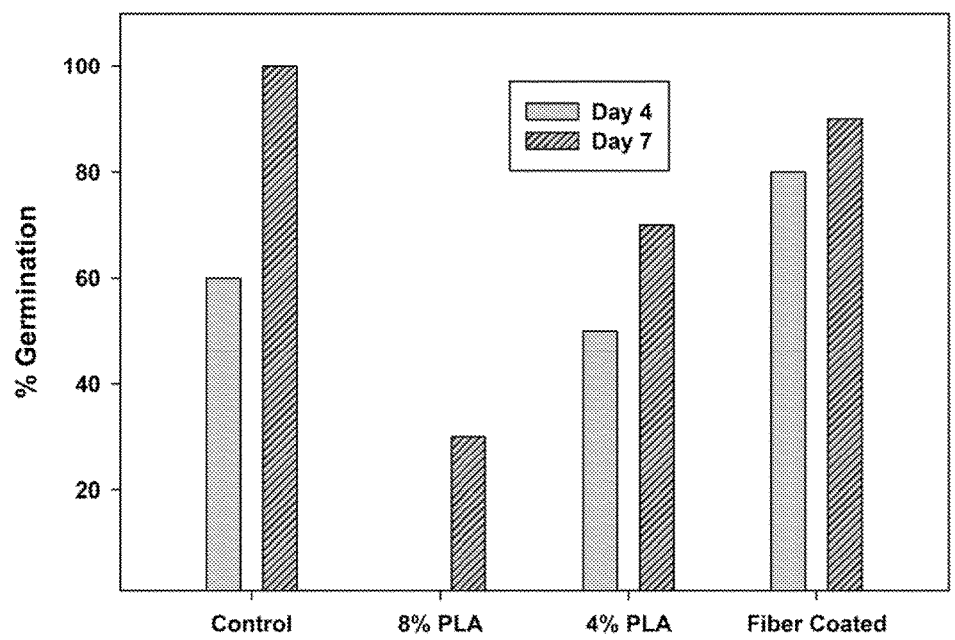
FIG. 12. Bean seed germination after coating seeds with a film of PLA. See Section 6.4 for details.

Trial 3:

Bean seeds (Roma II) were subjected to 4 treatments: untreated, dipped in 8% PLA; dipped in 4% PLA, and electrospun with PLA fibers generated from 8% PLA. Ten seeds of each treatment were placed in Petri dishes with moistened filter paper. Germination was recorded 4 d and 7 d post treatment. Germination was inhibited by dipping in PLA but it was not appreciably affected by coating with PLA fibers (FIG. 12).

Trials 4-5. Foliar Electrosprayed PLA with Imidacloprid.

Figure 13:
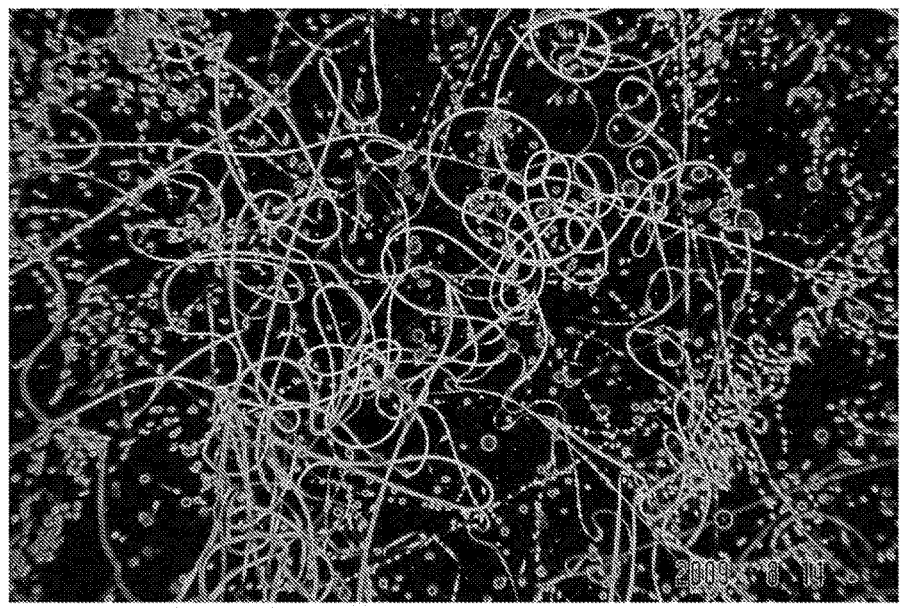
FIG. 13. Photomicrograph showing the physical shapes of PLA applied to a microscope slide. See Section 6.4 for details.
Figure 14:
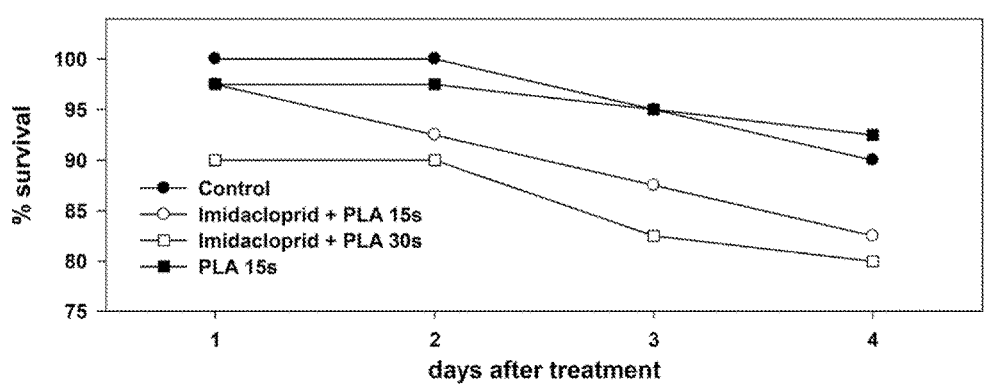
FIG. 14. Striped cucumber beetle survival after presentation of squash cotyledons treated with PLA+imidacloprid at low rate. See Section 6.4 for details.
Figure 15:
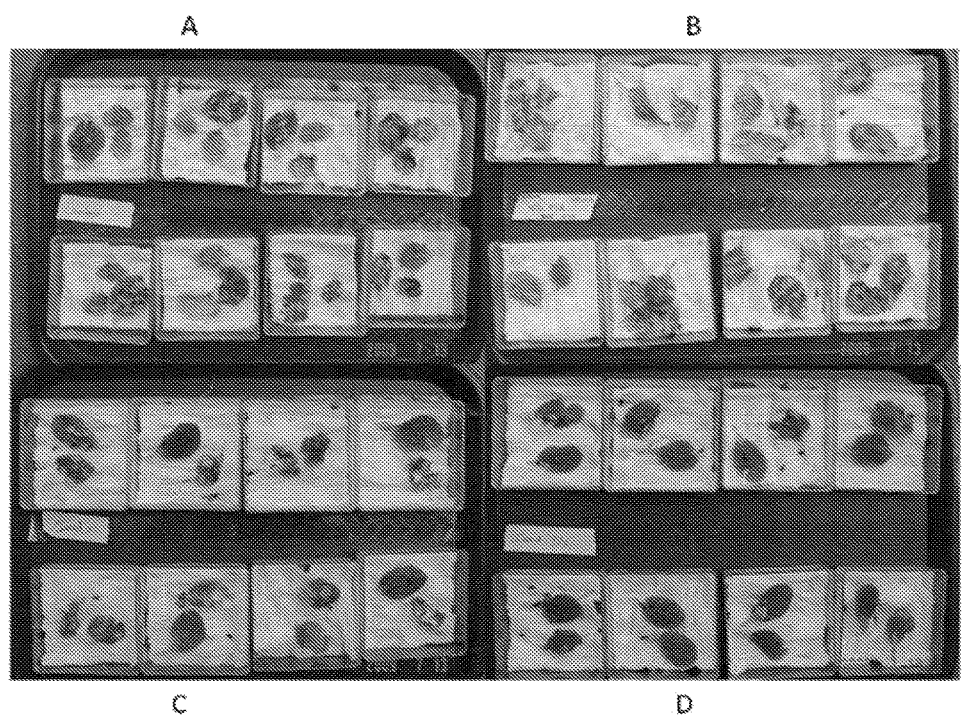
FIG. 15. Photographs of feeding damage by striped cucumber beetles after presentation with squash cotyledons treated with A—nothing, B—PLA alone 15s spray, C—PLA+imidacloprid (15 s spray) and D—PLA+imidacloprid (30 s spray). See Section 6.4 for details.

Trial 4:

Imidacloprid 98% technical was used at a rate of 0.0035 g per 25 ml of approx. 4% PLA in 4:3 chloroform:acetone solvent. The upper surface of grounded single cotyledons of acorn squash 'Table Gold' were electrosprayed at 30 kV with for 15 s and 30 s. Controls were cotyledons sprayed with PLA alone for 15 s and untreated cotyledons. Unsexed adult field-caught striped cucumber beetles (*Acalymma vittatum*) were presented with 2 cotyledons in an enclosed arena containing moistened absorbent pad. There were 8 replicates of each treatment that were exposed to 5 beetles. Beetle survival was evaluated daily for 5 days. In controls, cotyledon consumption was sufficiently high that an additional cotyledon was inserted into the arena after 3 days so that the beetles did not die of starvation. Spray deposition was visualized by spraying onto microscope slides and showed that a mixture of fibers, spheres and lenticular particles were deposited (FIG. 13). Results indicated that PLA+imidacloprid caused substantially more beetle mortality than in the absence of imidacloprid (FIG. 14). Feeding damage was visually assessed and showed that the presence of imidacloprid in PLA caused virtual cessation of beetle feeding at the 30 s treatment level (FIG. 15).

Figure 16:
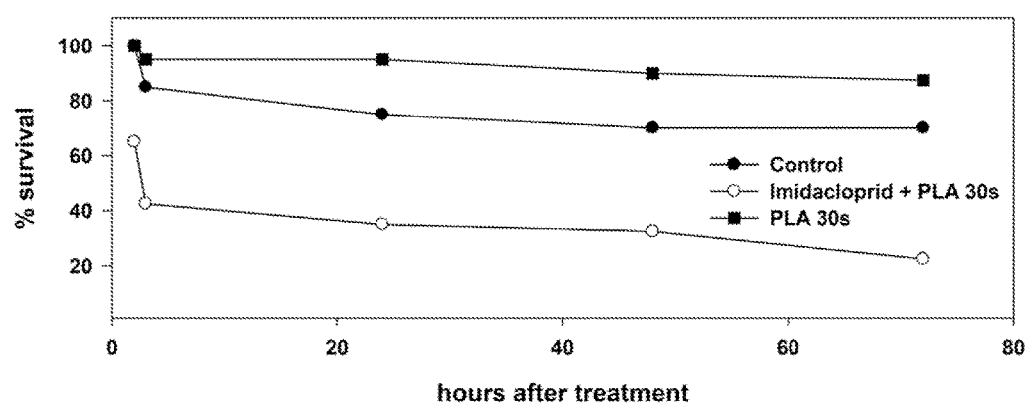
FIG. 16. Striped cucumber beetle survival after presentation of squash cotyledons treated with PLA+imidacloprid at high rate. See Section 6.4 for details.

Trial 5:

A second trial was conducted using the same methods but with an imidacloprid concentration of 0.0069 g of imidacloprid/ml solution and a spray duration of 30 s. Beetle mortality was greater for imidacloprid treated cotyledons and results confirmed that we could deliver a toxic dose of imidacloprid in a PLA carrier (FIG. 16).

Trial 6: PLA+Imidacloprid Electrosprayed onto Seed.

Figure 17:
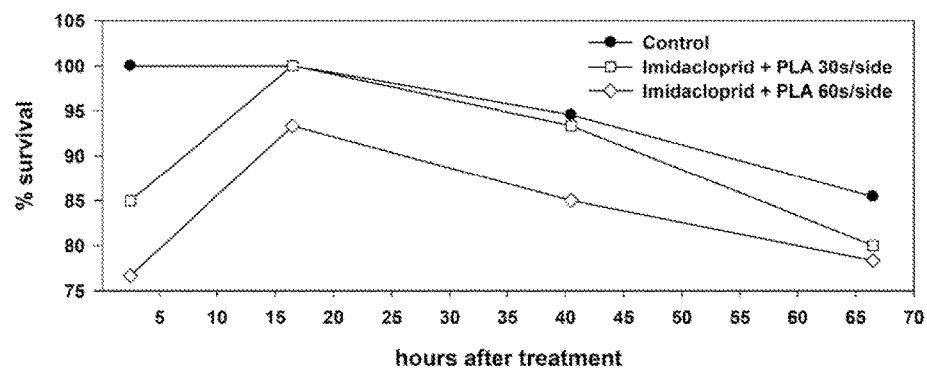
FIG. 17. Striped cucumber beetle survival after presentation of squash cotyledons from seeds treated with PLA+imidacloprid. See Section 6.4 for details.

Another trial was conducted to simulate conventional seed treatment. The methods were the same as for cotyledons except that grounded squash seeds were electrosprayed on each side of the seed for 30 s and 60 s and the concentration of spray material was 0.0219 g/ml solution. Controls were untreated seeds. The seeds were then planted in potting soil and after 6 days cotyledons were removed for presentation to beetles as described above. There were 12 replicates of each treatment. Results indicated that beetle survival was affected by the presence and dose of imidacloprid carried in PLA (FIG. 17). The results also indicated that the 30 s/side dose was insufficient to cause mortality and the apparent mortality in the initial observation was transient narcosis.

Conclusion

The above trials were a model system that showed the feasibility of including a toxic dose of insecticide within the PLA matrix, thus demonstrating the potential for inclusion of a similar toxicant in a polymeric mixture with varying hydrophilicity/hydrophobicity.

6.5 Example 5: Controlled Release of Thiamethoxan from Nanospun PLA Fabric

This example demonstrates controlled release of an exemplary pesticide, thiamethoxan, from nanospun PLA fabric (matting).

50% by weight thiamethoxan was incorporated into polylactic acid (PLA) fibers during electrospinning by co-dissolving/suspending thiamethoxan with PLA in chloroform/acetone as described in the methods above in Sections 6.1 and 6.2. The resulting nanofiber fabrics were used to deliver thiamethoxan to pole beans as described below.

The effect of a controlled-release, systemic thiamethoxan treatment on greenhouse whiteflies was tested. Four treatments were used and each treatment was replicated 5 times. In all the treatments, the PLA fabric was placed alongside Kentucky Wonder pole bean seeds during planting. The controls consisted of 3.954 $cm^2$ pieces of unloaded PLA fabric, while the 3 experimental treatments included 3 varying sizes of thiamethoxan loaded PLA which in turn equated to 3 different dosages (low, medium, and high dosage rates). Given that the recommended dosage for a given seed is 140 μg, low rate treatments were established in which the plants received pieces of PLA equivalent to 50% of the recommended dosage. The medium rate treatments were treated with the 100% of the recommended dosage and the high rate treatments were treated with 200%. Since the density of thiamethoxan in the PLA fabric was assumed to be a uniformly distributed 834.926 $\mu g/cm^2$, these differing rates were achieved by varying the size of the PLA fabric that was placed with the bean seed.

To ensure that 100% germination would occur among the planted bean seeds, all the seeds were primed and only seeds that had shown the emergence of a radical were planted. Upon emergence, each of the 20 bean plants was watered daily with an appropriate amount of water and once the plants were all deemed suitably large, 20 adult greenhouse whiteflies were caged to a single leaf on each plant. In order to measure the efficacy of the thiamethoxan release, whitefly mortality was recorded daily for 9 days.

Figure 18:
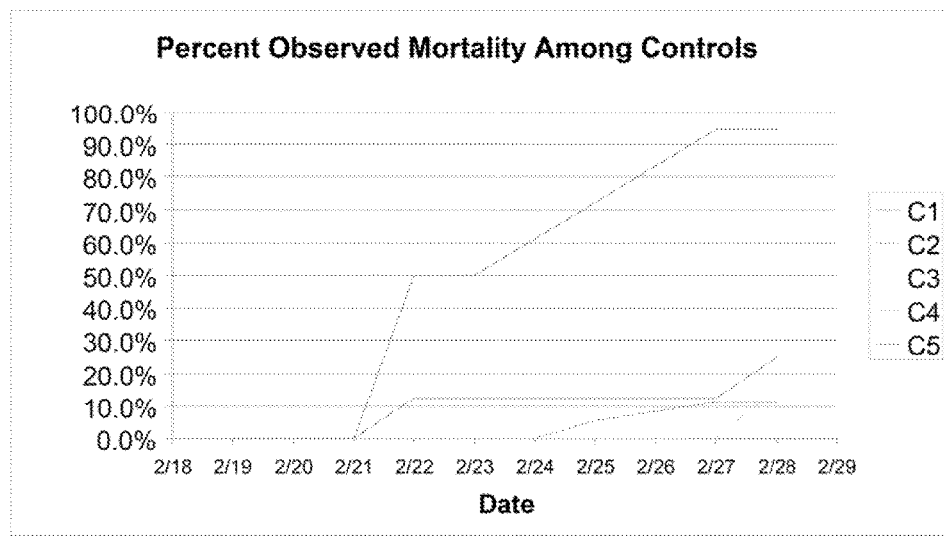
FIG. 18. Percent observed mortality of whiteflies among controls. See Section 6.5 for details.

FIG. 18 shows percent observed mortality of whiteflies among controls.

Figure 19:
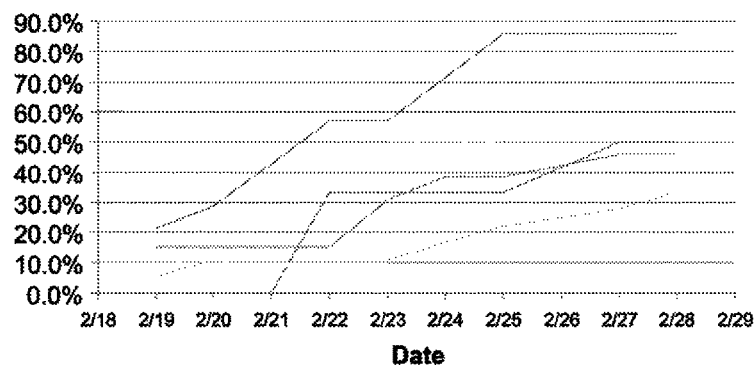
FIG. 19. Percent observed mortality of whiteflies among low rate replicates. See Section 6.5 for details.

FIG. 19 shows percent observed mortality of whiteflies among low rate replicates.

Figure 20:
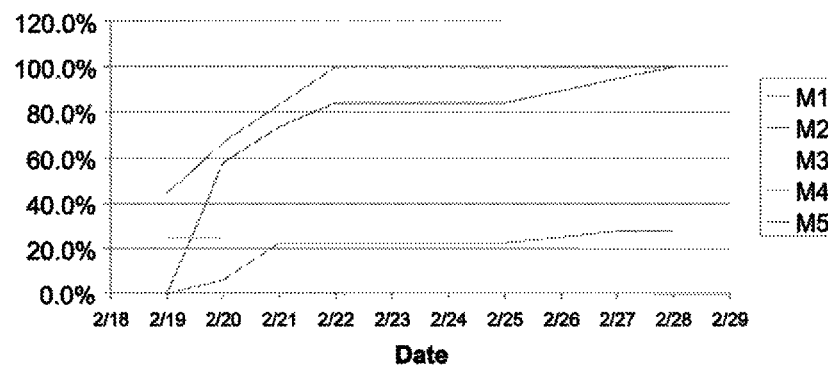
FIG. 20. Percent observed mortality of whiteflies among medium rate replicates. See Section 6.5 for details.

FIG. 20 shows percent observed mortality of whiteflies among medium rate replicates.

Figure 21:
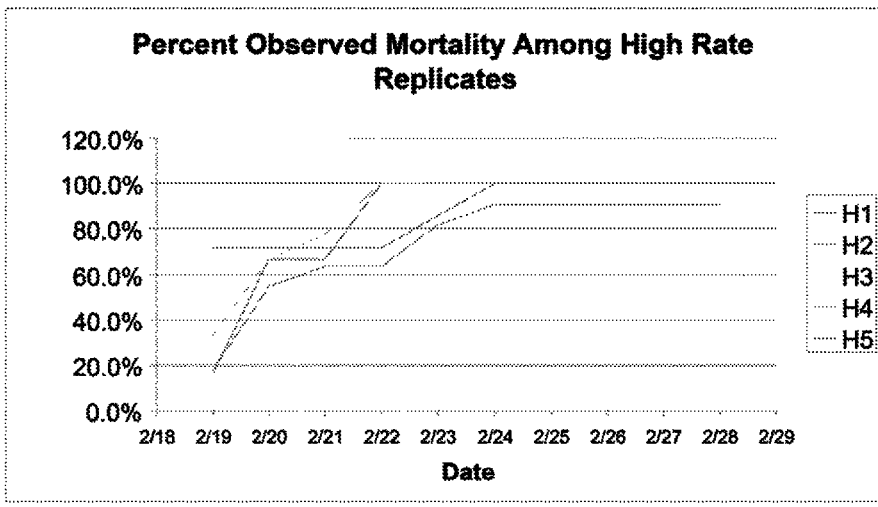
FIG. 21. Percent observed mortality of whiteflies among high rate replicates. See Section 6.5 for details.

FIG. 21 shows percent observed mortality of whiteflies among high rate replicates.

Figure 22:
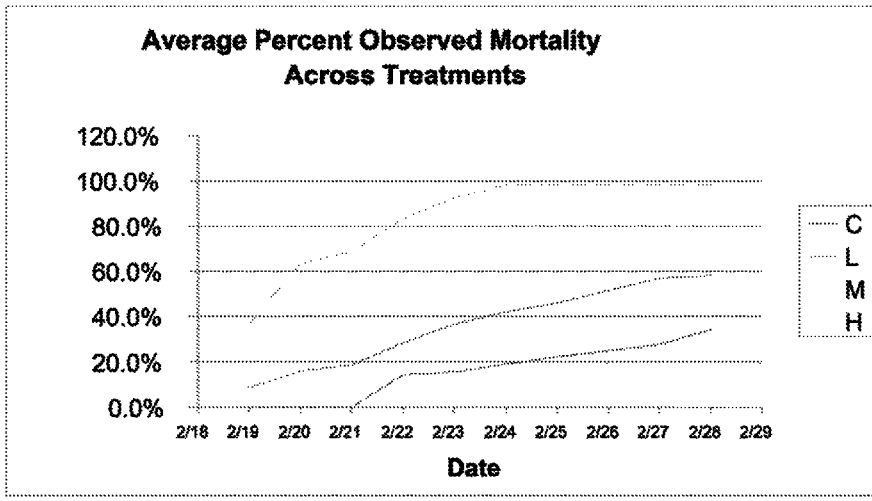
FIG. 22. Composite graph showing mean percent observed mortality of whiteflies among the treatments shown in FIGS. 18-21. See Section 6.5 for details.

FIG. 22 shows mean percent observed mortality of whiteflies among treatments.

Upon conclusion of the experiment, the anticipated trends were observable where the low rate treatments showed higher mortality than the controls, the medium treatments showed higher mortality than the low rate treatments, and finally high rate treatments exhibited the most significant mortality rates. Within the data, there appears to be little variance up through the third day of sampling however beyond that some statistical outliers emerged.

6.6 Example 6: Encapsulation of a Model Pesticide Compound in Electrospun Nanofibers Introduction Controlled release pesticide formulations have the potential to reduce the environmental problems associated with the application of pesticides. There are many advantages of controlled release formulations including an increased safety to the user and non-target organisms, a reduction in the amount of pesticides applied, reduced leaching of pesticides, and increased persistence of the active ingredient (Cotterill, J. V. and R. M. Wilkins, Controlled release of phenylurea herbicides from a lignin matrix: Release kinetics and modification with urea. Journal Of Agricultural And Food Chemistry, 1996. 44(9): p. 2908-2912). Microencapsulation technology has significant commercial value for improved resistance of pesticides to photolytic degradation and runoff. It is broadly defined here as the coating of pesticides using a polymer. The coating can be a single polymer film completely entrapping the pesticide (such as single-core microcapsule), or it could be blended with the pesticide such that the pesticide is homogeneously distributed as a distinct second phase throughout the polymer continuous phase (commonly described as microsphere or multicore particle). If the polymer and pesticide are miscible and solidification occurs above ambient temperature, then films can be prepared. Even though microencapsulation has produced several successful applications for pesticide formulations, it is not widely used because of the perceived hurdles associated with the cost. Low-cost biodegradable polymers with possible agricultural utility have been developed and commercialized. The range of physical properties of the polymers and their varied degradation rates permit the selection of a polymer to match a customized release rate. Six principal materials are employed in biodegradable agricultural formulations. Wilkins categorizes these as amylase-based (i.e. starch), polysaccharides (e.g., cellulose, chitosan, carrageenan, agarose), proteins (e.g., casein, gelatin), lignins, lipophilics (i.e., rubber and waxes), and synthetics (e.g., polyvinyl alcohol, polyesters, polyacrylamide) (Mary Marshall, S. W., Christopher Brazel, Matthew Alexander, Susumu Akatagawa, Controlled Delivery of Pesticides Through Synthetic Biodegradable Polymer Composites. Controlled-Release Delivery Systems for Pesticides, ed. H. B. Scheer. 1999: Marcel Dekker, Inc. 263-295). In the proposed research, the biodegradable electrospun PLA/cellulose non-woven fabrics will offer a $7^{th}$ category with both hydrophilic and hydrophobic properties.

Polylactic acid (PLA) is a highly versatile, biodegradable, aliphatic polyester derived from 100% renewable resources, such as corn and sugar beets. Cargill Dow LLC has developed a patented, low-cost continuous process for the production of lactic acid-based polymers (Drumright, R. E., P. R. Gruber, and D. E. Henton, Polylactic acid technology. Advanced Materials, 2000. 12(23): p. 1841-1846). This low-cost biodegradable PLA increases the range of controlled-release options for agricultural utility.

PLA is well-known as a biodegradable polymer in nature or compost. However, PLA is not easily biodegraded by microorganisms or enzymes in soil or water in nature, unless the period exceeds two years. This degradation rate is not sufficiently fast for applications where degradation times of a few months are desired (Funabashi, M. and M. Kunioka, Biodegradable composites of poly(lactic acid) with cellulose fibers polymerized by aluminum triflate. Macromolecular Symposia, 2005. 224: p. 309-321).

The environmental degradation of PLA occurs by a two-step process. During the initial phase of degradation, the high molecular weight polyester chains hydrolyze to lower molecular weight oligomers. This reaction can be accelerated by acids or bases and is affected by both temperature and moisture levels. Embrittlement of the plastic occurs during this step at a point where the Mn decreases to less than about 40000. At about this same Mn, microorganisms in the environment continue the degradation process by converting these lower molecular weight components to carbon dioxide, water, and humus. The structural integrity of molded PLA particles decreases as the molecular weight drops and eventually the particle disintegrates. A microstructure or morphology related to the hydrophilicity of PLA is very important for controlling the hydrodegradation rate. Funabashi et al. (Masahiro Funabashi, M. K., Biodegradable Composites of Poly(lactic acid) with Cellulose Fibers Polymerized by Aluminum Triflate. Macromolecular Symposia, 2005. 224(1): p. 309-321) reported that the biodegradability of PLA composites was accelerated by the existence of paper fibers or cotton fibers. In the proposed research, cellulose nanofibrils will be added to PLA fibers to vary the surface chemistry of the electrospun non-woven fabrics and hence improve the biodegradation rate.

Cellulose in the form of nanofibrils is the load-bearing constituent in plants. Cellulose nanofibrils are arranged in bundles of 10-50 nm width, and have fine diameter, large aspect ratio (fiber length divided by diameter), biocompatibility, high strength and modulus as well as other favorable physical properties associated with the highly crystalline extended chain conformation. Advanced materials based on this constituent are therefore likely to be developed in the near future (W. J. Orts, R. H. Marchessault, J. F. Revol, Enhanced Ordering of Liquid Crystalline Suspensions of Cellulose Microfibrils: A Small Angle Neutron Scattering Study. Macromolecules, 1998. 31: p. 5717-5725).

Electrospinning generates nanofibers with large surface area to volume ratio, which is beneficial to diffusion. PLA has been investigated widely via electrospinning techniques (Fong, H. D. H. R., Electrospinning and the Formation of Nanofibers, in Structure Formation in Polymeric Fibers, D. R. Salem, Editor. 2000, Hanser Gardner Publications, Inc: Cincinnati. p. 225-246; Kim, K. W., Y. L. Joo, and E. P. Giannelis, Effects of Nanoclay on Molecular Structures of Poly(L-lactic) Acid in Electrospinning. Symposium on Polymeric Nanofibers, ACS Fall Meeting, 2003; Zeng, J., et al, Ultraline Fibers Electrospun from Biodegradable Polymers. Journal of Applied Polymer Science, 2003. 89(4): p. 8). Frey et al. reported that the average diameter of PLA electrospun from 22 wt. % PLA/DMF solution at 70° C. was 281 nm (Margaret W. Frey, et al., Incorporation of biotin into PLA nanofibers via suspension and dissolution in the electrospinning dope. Journal of Biobased Materials and Bioenergy, 1, 219-227 (2007)). Additionally, a wide variety of materials have been incorporated in electrospun PLA fibers to tailor the fibers for particular end uses (Dapeng Li, M. W. F., Antje J. Baeumner, Electrospun Polylactic Acid Nanofiber Membranes as Substrates for Biosensor Assemblies. Journal of Membrane Science, 2006. 279: p. 354-363).

Researchers have successfully produced cellulose micro/nano fibrils with an average length smaller than 200 nm (Dong, X. M., J. F. Revol, and D. G. Gray, Effect of microcrystallite preparation conditions on the formation of colloid crystals of cellulose. Cellulose, 1998. 5(1): p. 19-32). A problem is that once the micro/nano fibrillated cellulose is dried, it is very difficult to re-disperse into water since hydrogen bonds cause strong adhesion between the individual micro/nano fibrils. Marcovich et al. (Marcovich, N. E., et al., Cellulose micro/nanocrystals reinforced polyurethane. Journal of Materials Research, 2006. 21(4): p. 870-881) reported that a stable suspension of cellulose nanocrystals was obtained in DMF. After the hydrolysis treatment, the cellulose nanocrystals were freeze-dried and re-dispersed by ultrasonic agitation in DMF. In the proposed research, cellulose nanofibrils (average length will be smaller than 200 nm) will be produced and incorporated into PLA/DMF solution before electrospinning. Nanocomposite fibers will be electrospun from PLA-cellulose/DMF suspension.

The simplicity of the electrospinning process itself and the ability to vary the fiber diameter by changing the solution concentration make this a promising technology for preparing useful polymer systems for controlled release delivery of chemicals (Deitzel, J. M., The Effect of Processing Variables in the Morphology of Electrospun Nanofibers and Textiles. Polymer, 2001. 42: p. 261-272; Kenawy, E. R., Release of Tetracycline Hydrochloride from Electrospun Poly(ethylene-co-vinylacetate), Poly(lactic acid), and a Blend. Journal of Controlled release, 2002. 81: p. 57-64). Moreover, a significant implication of the mechanism of electrospinning is that it allows a bicomponent system that will have properties from each of the polymeric components, e.g., one of the polymers could contribute to hydrophilicity while the other could enhance the hydrophobicity of the resulting non-woven fabrics, in principle offering another and quite unique means of controlling release rates. Controlled release technologies are used to deliver compounds like drugs, pesticides or fragrances at prescribed rates, together with improved efficacy, safety and convenience. The principal requirement of controlled release systems is that the release profile and rate are controlled. The release can be controlled by a variety of parameters, for example, the chemical/polymer ratio, the diameters of the fibers and the non-woven fabric structure (pore size). This process constitutes the foundation of the drug delivery technology, which also has been an active area of research in the recent past. The aims of controlled release formulations are to protect the supply of the agent, to allow the automatic release of the agent to the target at a controlled rate, and to maintain its concentration in the system within the optimum limits over a specified period of time, thereby providing great specificity and persistence.

Zeng et al. (Jing, Z., et al., Biodegradable electrospun fibers for drug delivery. Journal Of Controlled Release, 2003. 92(3): p. 227-231) reported that drug encapsulated inside the electrospun PLA fibers was released constantly along with the degradation of fibers. In the proposed research, a dye (Rhodamine B (basic violet 10)) as a model pesticide compound will be encapsulated inside the electrospun nanofibers and the release profile of the dye will be explored by diffusion and the degradation of nanofibers.

Tarvainen et al. (Tarvainen, T., Degradation of and drug release from a novel 2,2-bis(2-oxazoline) linked poly(lactic acid) polymer. Journal of Controlled Release, 2002. 81: p. 251-261) suggested that the degradation rate of a biodegradable polymer was related to the drug release rate from the polymer. The increased hydrophilicity and the absence of a crystalline phase of PLGA resulted in a faster swelling of the polymeric matrix, which promoted both drug diffusion and polymer erosion. Breitenbach et al. (Armin Breitenbach, Y. X. L., Thomas Kissel, Branched biodegradable polyesters for parenteral drug delivery systems. Journal of Controlled Release, 2000. 64: p. 167-178) reported that drug release from polyesters, such as PLA and PLG, was generally controlled by both drug diffusion and polymer erosion. In an initial phase, release occurred predominantly by pore diffusion through an interconnecting network formed by the dissolving drug substance itself. The second release phase was governed by polymer degradation. Increasing the hydrophilicity of PLA led to an acceleration of polymer degradation rates. Increased hydrophilicity of PLA caused a faster swelling of the polymeric matrix and, thereby, promoted both drug diffusion and polymer erosion. In this study, cellulose nanofibrils will be incorporated into the electrospun nanofibers to improve the biodegradation of PLA and control the release of the dye.

The most common mathematical model for controlled release is Fickian diffusion (the dynamic dispersion of a concentrated material in a larger medium in which a concentration gradient is the primary driving force). A simplified model for fractional release was developed by Franson and Peppas: (Mary Marshall, S. W., Christopher Brazel, Matthew Alexander, Susumu Akatagawa, Controlled Delivery of Pesticides Through Synthetic Biodegradable Polymer Composites. Controlled-Release Delivery Systems for Pesticides, ed. H. B. Scheer. 1999: Marcel Dekker, Inc. 263-295)

$$M_t/M_\infty = kt^n + C \qquad (1)$$

where $M_t$ is the mass of active ingredient released from a controlled-release device at any time t, $M_\infty$ is the corresponding mass released at infinite time, and k and n are empirical parameters indicative of the release kinetics. The constant C represents the burst release, or the amount of active ingredient released immediately at time zero. The four assumptions for this model are: (1) the diffusion medium does not swell or interact with the active ingredient, (2) release occurs when the active ingredient dissolves in a solvent that penetrates the diffusion medium, (3) there is a perfect sink condition at the surface of the controlled-release device (i.e., the concentration of the active ingredient outside the controlled-release device is zero), (4) all diffusion occurs away from the center of the device (symmetry condition). The value of n for Fickian diffusion depends upon the geometry of the system. In planar devices, where one-dimensional diffusion occurs, n=0.50 (generally, when the aspect ratio is greater than 10, one-dimensional diffusion is assumed). For cylindrical samples with one-dimensional radial diffusion, n=0.43; for spherical geometries, the exponent is 0.45. Release rates for polymer that swell will be greater than those with Fickian diffusion, and n as great as 1.2 has been observed.

In degradable systems, the protective polymer coating can release the active ingredient by either surface erosion or bulk erosion (especially common in systems that undergo large internal stresses when exposed to the release medium).

When the rate of degradation is extremely small compared to solute diffusion rates, the release of embedded active ingredient will be controlled by molecular pore volumes and diffusional distances; for spherical systems, n=0.45 is thus expected. Bulk erosion release cannot be modeled using Eq. (1). In this case, release rates often increase dramatically during experiments, due to the increase in surface area after large sections of the controlled-release device break apart. Alternately, when surface degradation happens very rapidly compared to diffusion, the release mechanism will be controlled largely by the geometry of the device. In planar systems, the solute release rate should be fairly constant (Case II diffusion with n=1.0), because each successive layer of carrier liberated contains the same concentration of the active ingredient. In spherical systems, the release rate will decrease with time, since the surface area of each successive layer is smaller (e.g., peeling an onion); so near time zero, n=1.0, it will eventually fall below 0.5. In analyzing surface erosion release from biodegradable systems, using Eq. (1) to fit experimental data and determine an "n" value, deviations of n of ~0.05 (assuming a correlation coefficient of 0.99) from the typical Fickian behavior are sufficient to indicate that the degradation process is affecting the release profile.

This example demonstrates the development of nanofibers from biodegradable polymers for controlled release delivery of chemicals. In particular, this example describes how PLA/cellulose nanocomposite fibers can be produced by incorporating cellulose nanofibrils in the PLA electrospinning dope. Hydrolytic degradation rate of electrospun PLA/cellulose nanocomposite fibers can increase with increasing cellulose nanofibril loading. Pesticides, represented in this example by a dye (Rhodamine B (basic violet 10)) can be incorporated into electrospun PLA/cellulose nanocomposite fibers by incorporating the dye in the spinning dope. Pesticide, represented in this study by a dye (Rhodamine B (basic violet 10), can diffuse out of electrospun PLA/cellulose nanocomposite into aqueous buffer solutions representing soil conditions. Diffusion rate of Rhodamine B can increase with increasing cellulose nanofiber loading. Pesticide, represented in this study by Rhodamine B, can be released from the fibers during the hydrolytic degradation process at a rate proportional to the degradation rate.

A mathematical model for pesticide release rate from electrospun PLA/cellulose nanocomposite fibers as a function of cellulose content of the nanofibers can be developed based on a combination (summation) of the release rate due to diffusion and the release rate due to biodegradation of the fibers.

Methods and Procedures

Formation of Non-Woven Fabrics of PLA/Cellulose Nanofibrils

The starting material to produce cellulose nanofibrils is cellulose microcrystalline powder (MCC) (extra pure, average particle size 90 μm) from ACROS Organics. The chemical treatment used to produce cellulose nanofibrils is described by Dinand et al. (E. Dinand, H. C., M. R. Vignon, Parenchymal cell cellulose from sugar beet pulp: preparation and properties. Cellulose, 1996. 3: p. 183-188) and Roman et al. (Roman, M. and W. T. Winter, Effect of sulfate groups from sulfuric acid hydrolysis on the thermal degradation behavior of bacterial cellulose. Biomacromolecules, 2004). The size of the cellulose nanofibrils is determined by a transmission electron microscopy (TEM). The crystallinity of the cellulose nanofibrils is determined by a wide angle X-ray diffraction (WAXD). 0 wt. %, 10 wt. %, and 20 wt. % of cellulose nanofibrils (on the weight of PLA) will be incorporated into 22 wt. % PLA/DMF solution and the suspension will be electrospun at 70° C. PLA (Mw=211,332, Mn=109,337) is supplied by Cargill-Dow (Minnetonka, Minn.). The distribution of cellulose nanofibrils inside the PLA nanofibers will be determined by TEM. The crystallinity of the electrospun nanofibers will be determined by WAXD. The contact angle of the electrospun non-woven fabrics will be tested to study the influence of cellulose nanofibrils on the surface chemistry of the non-woven fabrics.

Biodegradation of Fibers as a Function of Cellulose Content

The hydrolytic degradation of dye-free electrospun non-woven fabrics is conducted based on the method by Tarvainen et al. (Tarvainen, T., Degradation of and drug release from a novel 2,2-bis(2-oxazoline) linked poly(lactic acid) polymer. Journal of Controlled Release, 2002. 81: p. 251-261). The dye-free electrospun non-woven fabrics (40×40 $mm^2$) is studied by shaking the non-woven fabrics in closed bottles with 40 ml of PBS (ph 7.4, 50 mM $KH_2PO_4$ and 39.1 mM NaOH, USPIV, at 30° C.). The weight of the electrospun non-woven fabrics is measured before and after the degradation process. The dried non-woven fabric is dissolved in chloroform and cellulose nanofibrils are filtered out. The molecular weight (Mn, Mw) of PLA is determined by SEC. The percent of molecular weight remaining (Mw %, Mn %) and the percent of weight remaining (m %) is calculated. After the biodegradation process, the PBS solution for PLA and/or PLA/cellulose is analyzed by LC-MS to measure any cellulose is biodegradation products.

Incorporation of Rhodamine B into Fibers

Rhodamine B ($C_{28}H_{31}ClN_2O_3$, F.W.=479.02, Log $K_{ow}$=1.85, melting point=210-211° C.) is incorporated into fibers before electrospinning. The maximum amount of dye which can be incorporated into the PLA-Cellulose/DMF system is explored as a function of the cellulose nanofibrils concentration. The dye distribution in the electrospun non-woven fabrics is determined by Cl-mapping with an electron microprobe.

Diffusion of Rhodamine B from Fibers

Dye release from the electrospun non-woven fabrics (40×40 $mm^2$) is examined by shaking the non-woven fabrics containing the dye in distilled and deionized water at 30° C. for 24 hrs. Surfactant is added into the release bath to improve the water penetration into the electrospun non-woven fabrics. At predetermined time intervals, samples are collected. The dye concentration is determined by HPLC. The release profile of the dye from the electrospun non-woven fabrics is explored.

Rhodamine B Release from Fibers During the Biodegradation of Fibers

The electrospun non-woven fabrics containing Rhodamine B, is subjected to hydrolytic degradation in PBS (ph 7.4, 50 mM $KH_2PO_4$ and 39.1 mM NaOH, USPIV, at 30° C.). The dye released from the non-woven fabrics is extracted from the PBS buffer with EtOH (the solubility of Rhodamine B in EtOH is 50 mg/ml) and the dye concentration will determined by HPLC. The degradation of the non-woven fabrics is studied by measuring the molecular weight changing of the PLA. The PBS solution after the hydrolytic degradation is analyzed by LC-MS to check for any byproducts of dye degradation. The relationship between the release rate of the dye from the electrospun non-woven fabrics and the PLA hydrolytic degradation rate is correlated.

Statistical Analysis All treatments are performed in triplicate. Statistical analysis is used to investigate the correlation between of cellulose nanofibril concentration to the biodegradation rate of the electrospun non-woven fabrics, the correlation between release rate and the diffusion rate and the degradation rate of the electrospun non-woven fabrics.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A polymeric material comprising:
   a polymeric matrix material comprising poly(lactic acid);
   a hydrophilic polymeric material cellulose incorporated as nanofibrils or nanocrystals within the polymeric matrix material, wherein said cellulose is in the range of between 1% and 10% of the weight of the matrix material; and
   one or more compounds selected from a fertilizer, a plant growth hormone, a pheromone, a kairomone, an allomone, a pest repellent, or a pesticide, said one or more compounds incorporated in the polymeric matrix material,
   wherein said polymeric material is formed by preparing a solution of said poly(lactic acid) comprising a suspension of said nanofibrils or nanocrystals and subjecting said solution to electrospinning, wet spinning, dry spinning, dry-jet wet spinning, melt spinning, or gel spinning; and
   wherein the polymeric material provides for controlled release of the one or more compounds.

2. The polymeric material of claim 1 wherein release rate of the one or more compounds is controlled by varying the composition of hydrophilic polymeric material to poly(lactic acid).

3. The polymeric material of claim 1, wherein said one or more compounds is a pesticide selected from the group consisting of acaricide, algicide, avicide, bactericide, fungicide, herbicide, insecticide, mating disrupter, molluscicide, nematicide, rodenticide and virucide.

4. The polymeric material of claim 1 that is in the form of a fiber, filament, nonwoven fabric, film, coating, pellet, capsule, plastic shape, powder, granule, or gel.

5. The polymeric material of claim 1, wherein said one or more compounds is dispersed throughout said polymeric material.

6. The polymeric material of claim 1, wherein said polymeric matrix material is electrospun poly(lactic acid).

7. The polymeric material of claim 6, wherein said one or more compounds includes a pesticide and said pesticide is dispersed throughout said polymeric material.

8. The polymeric material of claim 6, wherein said one or more compounds includes a fertilizer and said fertilizer is dispersed throughout said polymeric material.

9. A plant or portion thereof comprising the polymeric material of claim 1 or 4.

10. The plant of claim 9, wherein said portion thereof is a seed.

11. A soil comprising a polymeric material comprising:
    a polymeric matrix material comprising poly(lactic acid);
    a hydrophilic polymeric material selected from cellulose incorporated as nanofibrils or nanocrystals within the polymeric matrix material, wherein said cellulose is in the range of between 1% and 10% of the weight of the matrix material; and
    a soil amendment incorporated in the polymeric matrix material,
    wherein said polymeric material is formed by preparing a solution of said poly(lactic acid) comprising a suspension of said nanofibrils or nanocrystals and subjecting said solution to electrospinning, wet spinning, dry spinning, dry-jet wet spinning, melt spinning, or gel spinning; and
    wherein the polymeric material provides for controlled release of the soil amendment.

12. A plant or portion thereof comprising a polymeric material, said polymeric material comprising:
    a polymeric matrix material comprising poly(lactic acid);
    a hydrophilic polymeric material selected from cellulose incorporated as nanofibrils or nanocrystals within in the polymeric matrix material, wherein said cellulose is in the range of between 1% and 10% of the weight of the matrix material: and
    one or more compounds selected from a fertilizer, a plant growth hormone, a pheromone, a kairomone, an allomone, a pest repellent, or a pesticide, said one or more compounds incorporated in the polymeric matrix material,
    wherein said polymeric material is formed by preparing a solution of said poly(lactic acid) comprising a suspension of said nanofibrils or nanocrystals and subjecting said solution to electrospinning, wet spinning, dry spinning, dry-jet wet spinning, melt spinning, or gel spinning;
    and
    wherein the polymeric material provides for controlled release of the one or more compounds.

13. The plant of claim 12, wherein said polymeric material is in the form of an electrospun non-woven fabric having a water contact angle of from $127\pm2$ to $115\pm3$.

14. The plant of claim 12, wherein said polymeric material is in the form of a spin-coated film having a water contact angle of from $91\pm2$ to $77\pm1$.

15. The polymeric material of claim 11, wherein said polymeric material is in the form of an electrospun non-woven fabric having a water contact angle of from $127\pm2$ to $115\pm3$.

16. The polymeric material of claim 11, wherein said polymeric material is in the form of a spin-coated film having a water contact angle of from $91\pm2$ to $77\pm1$.

17. A method for protecting a plant or a portion thereof from infestation by a pest or disease species comprising the step of adhering the polymeric material of claim 1 to the plant or portion thereof, or applying the polymeric material of claim 1 directly onto or into a substrate in which the plant or portion thereof is disposed, wherein the polymeric material comprises one or more compounds selected from the group consisting of pheromone, allomone, kairomone, pest repellent and pesticide.

18. The method of claim 17 wherein the pesticide is selected from the group consisting of acaricide, algicide, avicide, bactericide, fungicide, insecticide, mating disrupter, molluscicide, nematicide, rodenticide and virucide.

19. The method of claim 17 wherein the portion of the plant is selected from the group consisting of root, seed, bulb, corm, rhizome, tuber, leaf, flower, fruit, reproductive structures, bud, stem, bark and foliage.

20. The method of claim 17 wherein the protection has the purpose of remediating existing infestation of the plant or a portion thereof.

21. The method of claim 19 wherein the portion of the plant is a seed.

22. The method of claim 17 wherein the substrate is a substrate for growing a plant.

23. A method for regulating plant growth comprising the step of applying the polymeric material of claim 1 onto the plant or a portion thereof, or the step of applying the polymeric material of claim 1 directly onto or into a substrate in which the plant or a portion thereof is disposed, wherein the polymeric material comprises a compound that is a plant growth hormone.

24. The method of claim 23 wherein the portion of the plant is selected from the group consisting of root, seed, bulb, corm, rhizome, tuber, leaf, flower, fruit, reproductive structures, bud, stem, bark and foliage.

25. The method of claim 23 wherein the polymeric material is applied directly to the surface of the plant or portion thereof.

26. The method of claim 25 wherein the regulating of plant growth is promoting rate of growth, reducing the rate of growth, enhancing competition against weeds, destroying a plant or stimulating germination.

27. The method of claim 24 wherein the portion of the plant is a seed.

* * * * *